US012220604B2

(12) United States Patent
Sugihara et al.

(10) Patent No.: US 12,220,604 B2
(45) Date of Patent: Feb. 11, 2025

(54) TREATMENT OF METASTATIC BRAIN TUMOR BY ADMINISTRATION OF AN ANTIBODY-DRUG CONJUGATE

(71) Applicant: DAIICHI SANKYO COMPANY, LIMITED, Tokyo (JP)

(72) Inventors: Kiyoshi Sugihara, Tokyo (JP); Chiaki Ishii, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 963 days.

(21) Appl. No.: 17/264,250

(22) PCT Filed: Jul. 30, 2019

(86) PCT No.: PCT/JP2019/029765
§ 371 (c)(1),
(2) Date: Jan. 28, 2021

(87) PCT Pub. No.: WO2020/027100
PCT Pub. Date: Feb. 6, 2020

(65) Prior Publication Data
US 2021/0290777 A1 Sep. 23, 2021

(30) Foreign Application Priority Data
Jul. 31, 2018 (JP) ................... 2018-143372

(51) Int. Cl.
*A61K 47/68* (2017.01)
*A61K 31/4745* (2006.01)
*A61K 47/54* (2017.01)
*A61P 35/00* (2006.01)
*A61P 35/04* (2006.01)
(Continued)

(52) U.S. Cl.
CPC ...... *A61K 47/6843* (2017.08); *A61K 31/4745* (2013.01); *A61K 47/545* (2017.08); *A61K 47/68037* (2023.08); *A61K 47/6849* (2017.08); *A61K 47/6851* (2017.08); *A61K 47/6855* (2017.08); *A61K 47/6889* (2017.08); *A61P 35/00* (2018.01); *A61P 35/04* (2018.01); *C07K 16/18* (2013.01); *C07K 16/28* (2013.01); *C07K 16/2827* (2013.01); *C07K 16/30* (2013.01); *C07K 16/32* (2013.01)

(58) Field of Classification Search
CPC ............. A61K 47/6889; A61K 47/545; A61K 47/6803; A61K 47/6843; A61K 47/6849; A61K 47/6851; A61K 47/6855; A61K 31/4745; A61P 35/00; A61P 35/04; C07K 16/18; C07K 16/28; C07K 16/2827; C07K 16/30; C07K 16/32
See application file for complete search history.

(56) References Cited

U.S. PATENT DOCUMENTS 5,480,968 A    1/1996  Kraus et al.
5,677,171 A   10/1997  Hudziak et al.
(Continued)

FOREIGN PATENT DOCUMENTS

CA    2927832 A1    11/2011
CA    2815154 A1    2/2012
(Continued)

OTHER PUBLICATIONS

Krop IE, et al. (2015) Annals of Oncology 26:113-119. (doi: :10.1093/annonc/mdu486. Published online Oct. 29, 2014).*
(Continued)

*Primary Examiner* — Robert S Landsman
(74) *Attorney, Agent, or Firm* — Foley & Lardner LLP

(57) ABSTRACT

A therapeutic agent for a metastatic brain tumor comprising, as an active component, an antibody-drug conjugate in which a drug-linker represented by the following formula (wherein A represents a connecting position to an antibody) is conjugated to the antibody via a thioether bond and/or a method of treatment for a metastatic brain tumor, comprising administering the antibody-drug conjugate to a subject in need of the treatment for a metastatic brain tumor.

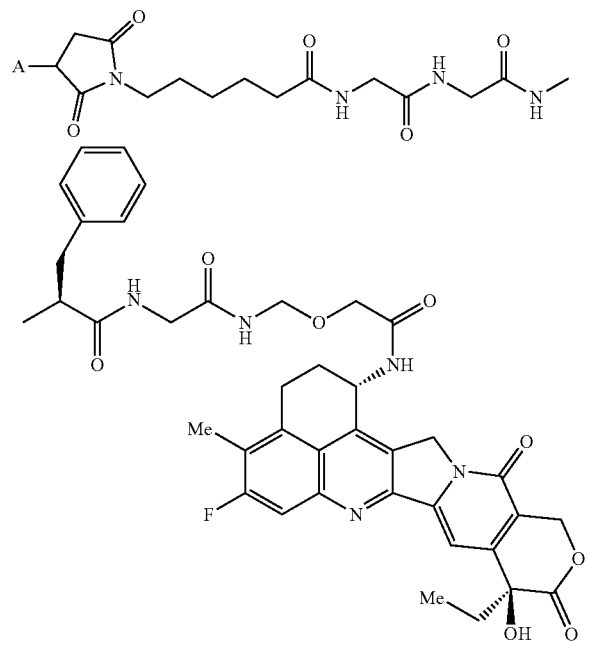

57 Claims, 8 Drawing Sheets
Specification includes a Sequence Listing.

(51) Int. Cl.
*C07K 16/18* (2006.01)
*C07K 16/28* (2006.01)
*C07K 16/30* (2006.01)
*C07K 16/32* (2006.01)

(56) References Cited

U.S. PATENT DOCUMENTS

| | | |
|---|---|---|
| 5,821,337 A | 10/1998 | Carter et al. |
| 5,834,476 A | 11/1998 | Terasawa et al. |
| 5,837,673 A | 11/1998 | Tsujihara et al. |
| 5,892,043 A | 4/1999 | Tsujihara et al. |
| 5,968,511 A | 10/1999 | Akita et al. |
| 6,071,719 A | 6/2000 | Halsey et al. |
| 6,096,868 A | 8/2000 | Halsey et al. |
| 6,214,345 B1 | 4/2001 | Firestone et al. |
| 6,291,671 B1 | 9/2001 | Inoue et al. |
| 6,835,807 B1 | 12/2004 | Susaki et al. |
| 7,041,818 B2 | 5/2006 | Susaki et al. |
| 7,449,184 B2 | 11/2008 | Allison et al. |
| 7,585,491 B2 | 9/2009 | Govindan |
| 7,833,979 B2 | 11/2010 | Sullivan et al. |
| 7,837,980 B2 | 11/2010 | Alley et al. |
| 7,999,083 B2 | 8/2011 | Govindan et al. |
| 8,226,945 B2 | 7/2012 | Ebens et al. |
| 8,268,319 B2 | 9/2012 | Govindan |
| 8,394,607 B2 | 3/2013 | Ebens et al. |
| 8,425,912 B2 | 4/2013 | Govindan |
| 8,524,865 B2 | 9/2013 | Ebens et al. |
| 8,741,291 B2 | 6/2014 | Bhat et al. |
| 8,802,820 B2 | 8/2014 | Chamberlain et al. |
| 8,907,071 B2 | 12/2014 | Sullivan et al. |
| 8,968,741 B2 | 3/2015 | Ebens et al. |
| 9,808,537 B2 | 11/2017 | Masuda et al. |
| 9,850,312 B2 | 12/2017 | Agatsuma et al. |
| 9,872,924 B2 | 1/2018 | Naito et al. |
| 10,195,288 B2 | 2/2019 | Masuda et al. |
| 10,227,417 B2 | 3/2019 | Agatsuma et al. |
| 10,383,878 B2 | 8/2019 | Hettmann et al. |
| 2003/0018989 A1 | 1/2003 | Brennan et al. |
| 2003/0148931 A1 | 8/2003 | Takahashi et al. |
| 2003/0166513 A1 | 9/2003 | Imura et al. |
| 2004/0185053 A1 | 9/2004 | Govindan |
| 2005/0123536 A1 | 6/2005 | Law et al. |
| 2005/0228007 A1 | 10/2005 | Jagtap et al. |
| 2005/0271671 A1 | 12/2005 | Griffiths |
| 2005/0276812 A1 | 12/2005 | Ebens, Jr. et al. |
| 2006/0018899 A1 | 1/2006 | Kao et al. |
| 2006/0134109 A1 | 6/2006 | Gaitanaris et al. |
| 2006/0193865 A1 | 8/2006 | Govindan |
| 2007/0071764 A1 | 3/2007 | Sullivan et al. |
| 2008/0050310 A1 | 2/2008 | Ebens et al. |
| 2008/0131363 A1 | 6/2008 | Govindan et al. |
| 2008/0161245 A1 | 7/2008 | Kratz et al. |
| 2008/0260744 A1 | 10/2008 | Gaitanaris et al. |
| 2008/0305044 A1 | 12/2008 | McDonagh et al. |
| 2009/0178153 A1 | 7/2009 | Gaitanaris et al. |
| 2009/0274713 A1 | 11/2009 | Chari et al. |
| 2009/0286258 A1 | 11/2009 | Kaur et al. |
| 2009/0291093 A1 | 11/2009 | Govindan |
| 2010/0068181 A1 | 3/2010 | Paliwal et al. |
| 2010/0120816 A1 | 5/2010 | Fontana et al. |
| 2010/0303802 A1 | 12/2010 | Zoffmann Jensen et al. |
| 2011/0045587 A1 | 2/2011 | Sullivan et al. |
| 2011/0059076 A1 | 3/2011 | McDonagh et al. |
| 2011/0070248 A1 | 3/2011 | Ichikawa et al. |
| 2011/0185439 A1 | 7/2011 | Gaitanaris et al. |
| 2011/0229406 A1 | 9/2011 | Hettmann et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2012/0328634 A1 | 12/2012 | Govindan |
| 2013/0089872 A1 | 4/2013 | Nakamura et al. |
| 2013/0123178 A1 | 5/2013 | Dimarchi et al. |
| 2013/0216561 A1 | 8/2013 | Govindan |
| 2013/0247233 A1 | 9/2013 | Gaitanaris et al. |
| 2014/0004078 A1 | 1/2014 | Govindan |
| 2015/0297748 A1 | 10/2015 | Masuda et al. |
| 2015/0352224 A1 | 12/2015 | Naito et al. |
| 2016/0219845 A1 | 8/2016 | Gaitanaris et al. |
| 2016/0279259 A1 | 9/2016 | Masuda et al. |
| 2016/0282365 A1 | 9/2016 | Gaitanaris et al. |
| 2016/0287722 A1 | 10/2016 | Immunomedics |
| 2016/0297890 A1 | 10/2016 | Agatsuma et al. |
| 2017/0021031 A1 | 1/2017 | Hettmann et al. |
| 2017/0188555 A1 | 7/2017 | Gaitanaris et al. |
| 2019/0091345 A1 | 3/2019 | Miao et al. |
| 2019/0151328 A1 | 5/2019 | Hettmann et al. |

FOREIGN PATENT DOCUMENTS

| | | |
|---|---|---|
| CA | 2859255 A1 | 6/2013 |
| CA | 2928794 A1 | 8/2015 |
| CN | 1227499 A | 9/1999 |
| CN | 1764478 A | 4/2006 |
| CN | 101023100 A | 8/2007 |
| CN | 101490087 A | 7/2009 |
| CN | 102481364 A | 5/2012 |
| EA | 201790334 A1 | 6/2017 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | H05-059061 A | 3/1993 |
| JP | H06-087746 A | 3/1994 |
| JP | H08-337584 A | 12/1996 |
| JP | H10-095802 A | 4/1998 |
| JP | H11-071280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2007-527872 A | 10/2007 |
| JP | 2008-521828 A | 6/2008 |
| JP | 2009-538629 A | 11/2009 |
| JP | 2010-513524 A | 4/2010 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| JP | 2015-509948 A | 4/2015 |
| JP | 2017-503784 A | 2/2017 |
| JP | 2017-105789 A | 6/2017 |
| JP | 2017-197523 A | 11/2017 |
| JP | 2017-222638 A | 12/2017 |
| JP | 2018-008982 A | 1/2018 |
| KR | 10-2001-0052385 A | 6/2001 |
| KR | 10-2011-0044808 A | 4/2011 |
| RU | 2404810 C2 | 7/2008 |
| RU | 2450008 C2 | 7/2010 |
| TW | 1232930 B | 5/2005 |
| TW | 200817434 A | 4/2008 |
| WO | WO-97/46260 A1 | 12/1997 |
| WO | WO-99/46296 A1 | 9/1999 |
| WO | WO-00/25825 A1 | 5/2000 |
| WO | WO-01/00244 A2 | 1/2001 |
| WO | WO-02/00734 A1 | 1/2002 |
| WO | WO-03/013602 A1 | 2/2003 |
| WO | WO-03/015826 A1 | 2/2003 |
| WO | WO-03/043583 A2 | 5/2003 |
| WO | WO-03/074566 A2 | 9/2003 |
| WO | WO-2004/040000 A2 | 5/2004 |
| WO | WO-2005/040825 A2 | 5/2005 |
| WO | WO-2005/112919 A2 | 12/2005 |
| WO | WO-2006/065533 A2 | 6/2006 |
| WO | WO-2006/092230 A2 | 9/2006 |
| WO | WO-2007/077028 A2 | 7/2007 |

(56) References Cited

FOREIGN PATENT DOCUMENTS

| | | |
|---|---|---|
| WO | WO-2008/100624 A2 | 8/2008 |
| WO | WO-2008/116219 A2 | 9/2008 |
| WO | WO-2008/144891 A1 | 12/2008 |
| WO | WO-2011/011474 A1 | 1/2011 |
| WO | WO-2011/021397 A1 | 2/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/126810 A1 | 8/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014/061277 A1 | 4/2014 |
| WO | WO-2014/107024 A1 | 7/2014 |
| WO | WO-2015/098099 A1 | 7/2015 |
| WO | WO-2015/115091 A1 | 8/2015 |
| WO | WO-2015/142675 A2 | 9/2015 |
| WO | WO-2015/155998 A1 | 10/2015 |
| WO | WO-2016/024195 A1 | 2/2016 |
| WO | WO-2017/133682 A1 | 8/2017 |
| WO | WO-2017/180813 A1 | 10/2017 |
| WO | WO-2018/066626 A1 | 4/2018 |
| WO | WO-2018/135501 A1 | 7/2018 |
| WO | WO-2018/185618 A1 | 10/2018 |
| WO | WO-2018/212136 A1 | 11/2018 |

OTHER PUBLICATIONS

Examination Report issued in corresponding Indian Patent Application No. 202117006725 dated Sep. 5, 2023 (9 pages).
Office Action issued in corresponding Japanese Patent Application No. 2020-534654 dated Aug. 29, 2023 (6 pages).
Tamura et al., "64Cu-DOTA-Trastuzumab PET Imaging in Patients with HER2-Positive Breast Cancer", The Journal of Nuclear Medicine, vol. 54, No. 11, Sep. 12, 2013, pp. 1869-1875.
International Searching Authority, "International Search Report," issued in connection with International Patent Application No. PCT/JP2019/029765, dated Oct. 29, 2019.
International Searching Authority, "Written Opinion," issued in connection with International Patent Application No. PCT/JP2019/029765, dated Oct. 29, 2019.
Ahn et al., "3083 AZD9291 activity in patients with EGFR-mutant advanced non-small cell lung cancer (NSCLC) and brain metastases: Data from Phase II studies," European Journal of Cancer, vol. 51, Sep. 2015, pp. S625-S626.
Alley et al., "Antibody-drug conjugates: targeted drug delivery for cancer," Current Opinion in Chemical Biology, vol. 14, 2010, pp. 529-537.
Askoxylakis et al., "Abstract P6-17-02: Ado-trastuzumab emtansine (T-DM1) is effective against established HER2-positive breast cancer brain metastases in mice," Cancer Research, vol. 76, Issue 4, 2016.
Askoxylaks et al., "Preclinical Efficacy of Ado-trastuzumab Emtansine in the Brain Microenvironment," Journal of the National Cancer Institute, vol. 108, Issue 2, Feb. 2016, 10 pages.
Bartsch et al., "Activity of T-DM1 in Her2-positive breast cancer brain metastases," Clinical & Experimental Metastasis, vol. 32, 2015, pp. 729-737.
Bartsch et al., "Trastuzumab prolongs overall survival in patients with brain metastases from Her2 positive breast cancer," Journal of Neuro-Oncology, vol. 85, 2007, pp. 311-317.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," Journal of Clinical Oncology, vol. 29, No. 4, Feb. 1, 2011, pp. 398-405.

Costa et al., "Clinical Experience With Crizotinib in Patients With Advanced ALK-Rearranged Non-Small-Cell Lung Cancer and Brain Metastases," Journal of Clinical Oncology, vol. 33, No. 17, Jun. 2015, pp. 1881-1888.
Damle, Nitin K., "Tumour-targeted chemotherapy with immunoconjugates of calicheamicin," Expert Opin. Biol. Ther., vol. 4, No. 9, 2004, pp. 1445-1452.
Di Lorenzo et al., "Targeted therapy of brain metastases: latest evidence and clinical implications," Therapeutic Advances in Medical Oncology, vol. 9, No. 12, Dec. 2017, pp. 781-796.
Doi et al., "Safety, pharmacokinetics, and antitumour activity of trastuzumab deruxtecan (DS-8201), a HER2-targeting antibody-drug conjugate, in patients with advanced breast and gastric or gastro-oesophageal tumours: a phase 1 dose-escalation study," The Lancet Oncology, vol. 18, Issue 11, Nov. 1, 2017, pp. 1512-1522.
Ducry et al., "Antibody—Drug Conjugates: Linking Cytotoxic Payloads to Monoclonal Antibodies," Bioconjugate Chem, vol. 21, 2010, pp. 5-13.
Dummer et al., "Vemurafenib in patients with BRAFV600 mutation-positive melanoma with symptomatic brain metastases: Final results of an open-label pilot study," European Journal of Cancer, vol. 50, Issue 3, Feb. 2014, pp. 611-621.
Hoffknecht et al., "Efficacy of the irreversible ErbB family blocker afatinib in epidermal growth factor receptor (EGFR) tyrosine kinase inhibitor (TKI)-pretreated non-small-cell lung cancer patients with brain metastases or leptomeningeal disease," Journal of Thoracic Oncology, vol. 10, No. 1, 2015, pp. 156-163.
Luchi et al., "Phase II trial of gefitinib alone without radiation therapy for Japanese patients with brain metastases from EGFR-mutant lung adenocarcinoma," Lung Cancer, vol. 82, Issue 2, Nov. 2013, pp. 282-287.
Kim et al., "Epidermal growth factor receptor tyrosine kinase inhibitors as a first-line therapy for never-smokers with adenocarcinoma of the lung having asymptomatic synchronous brain metastasis," Lung Cancer, vol. 65, Issue 3, Sep. 2009, pp. 351-354.
Lin et al., "Multicenter Phase II Study of Lapatinib in Patients with Brain Metastases from HER2-Positive Breast Cancer," Clinical Cancer Research, vol. 15, Issue 4, 2009, pp. 1452-1459.
Ogitani et al., "Bystander killing effect of DS-8201a, a novel anti-human epidermal growth factor receptor 2 antibody-drug conjugate, in tumors with human epidermal growth factor receptor 2 heterogeneity," Cancer Science, vol. 107, 2016, pp. 1039-1046.
Ogitani et al., "DS-8201a, A Novel HER2-Targeting ADC with a Novel DNA Topoisomerase I Inhibitor, Demonstrates a Promising Antitumor Efficacy with Differentiation from T-DM1," Clinical Cancer Research, vol. 22, No. 20, Oct. 15, 2016, pp. 5097-5108.
Okines et al., "Development and responses of brain metastases during treatment with trastuzumab emtansine (T-DM1) for HER2 positive advanced breast cancer: A single institution experience," the Breast Journal, vol. 24, No. 3, May 2018, pp. 253-259.
Rahmatulla et al., "The Molecular Biology of Brain Metastasis," Journal of Oncology, vol. 2012, Article ID 723541, 16 pages.
Ricciardi et al., "Efficacy of T-DM1 for leptomeningeal and brain metastases in a HER2 positive metastatic breast cancer patient: new directions for systemic therapy—a case report and literature review," BMC Cancer, vol. 18, Article No. 97, 2018, 8 pages.
Senter et al., "The discovery and development of brentuximab vedotin for use in relapsed Hodgkin lymphoma and systemic anaplastic large cell lymphoma," Nature Biotechnology, vol. 30, No. 7, Jul. 2012, pp. 631-637.
Takegawa et al., "DS-8201a, a new HER2-targeting antibody-drug conjugate incorporating a novel DNA topoisomerase I inhibitor, overcomes HER2-positive gastric cancer T-DM1 resistance," International Journey of Cancer, vol. 141, 2017, pp. 1682-1689.
Terrell-Hall et al., "Trastuzumab distribution in an in-vivo and in-vitro model of brain metastases of breast cancer," Oncotarget, vol. 8, No. 48, Oct. 2017, pp. 83734-83744.
Office Action issued in corresponding Canadian Patent Application No. 3108044 dated Apr. 13, 2022.
Abstract of Davoli, et al., "Progression and treatment of HER2-positive breast cancer", Cancer Chemother Pharmacol. 65(4): 611-23 (2010).

(56) References Cited

OTHER PUBLICATIONS

Acchione et al., "Impact of linker and conjugation chemistry on antigen binding, Fc receptor binding and thermal stability of model antibody-drug conjugates," mAbs, vol. 4, No. 3, May/Jun. 2012, pp. 362-372.
Adams et al., "Humanization of a recombinant monoclonal antibody to produce a therapeutic HER dimerization inhibitor, pertuzumab," Cancer Immunol. Immunother. 55:717-727 (2006).
Alimandi et al., "Cooperative signaling of ErbB3 and ErbB2 in neoplastic transformation and human mammary carcinomas," Oncogene 10:1813-1821 (1995)—9 Pages.
Allander et al., "Gastrointestinal Stromal Tumors with KIT Mutations Exhibit a Remarkably Homogeneous Gene Expression Profile," Cancer Research, vol. 61, pp. 8624-8628, Dec. 15, 2001.
Allowance issued in connection with Taiwanese Patent Application No. 104103127, dated Apr. 11, 2018.
Australian Intellectual Property Office, "Examination Report No. 2 for Standard Patent Application," Australian Patent Application No. 2014371934, dated Sep. 13, 2019.
Barginear et al., "Trastuzumab-DM1: A Review of the Novel Immuno-Conjugate for HER2-Overexpressing Breast Cancer," The Open Breast Cancer Journal, vol. 1, 2009, pp. 25-30.
Barok et al., "Trastuzumab-DM1 is highly effective in preclinical models of HER2-positive gastric cancer," Cancer Letters, vol. 306, 2011, pp. 172-179.
Baselga et al., "Phase II Study of Weekly Intravenous Recombinant Humanized Anti-p185HER2 Monoclonal Antibody in Patients with HER2/neu-Overexpressing Metastatic Breast Cancer," J. Clin. Oncol. 14(3):737-744 (Mar. 1996).
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Bauer et al., "Emerging Agents for the Treatment of Advanced, Imatinib-Resistant Gastrointestinal Stromal Tumors: Current Status and Future Directions," Drugs, vol. 75, 2015, pp. 1323-1334.
Beck, Alain, "The Next Generation of Antibody-drug Conjugates Comes of Age," Discovery Medicine, vol. 10, No. 53, Oct. 16, 2010 (8 pages).
Behrens et al., "Methods for site-specific drug conjugation to antibodies," mAbs, vol. 6, No. 1, 2014, pp. 46-53.
Blok et al., "Cytoplasmic Overexpression of HER2: a Key Factor in Colorectal Cancer," Clinical Medicine Insights: Oncology, vol. 7, 2013, pp. 41-51.
Bouchard et al., "Antibody-drug conjugates—A new wave of cancer drugs," Bioorganic & Medicinal Chemistry Letters, vol. 24, 2014, pp. 5357-5363.
Burke et al., "Design, Synthesis, and Biological Evaluation of Antibody-Drug Conjugates Comprised of Potent Camptothecin Analogues", Bioconjugate Chemistry, vol. 20, No. 6, 2009, pp. 1242-1250.
Calabrese et al., "Assignment of TACSTD1 (alias TROP1, M4S1) to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Callahan and Hurvitz, "HER2-Positive Breast Cancer: Current Management of Early, Advanced, and Recurrent Disease", Curr Opin Obstet Gynecol. 23(1): 37-43 (2011).
Canadian Intellectual Property Office, "Interview Summary," issued in connection with Canadian Patent Application No. 2,885,800, dated Mar. 28, 2017.
Canadian Intellectual Property Office, "Office Action," issued in connection with Canadian Patent Application No. 2,939,802, dated Apr. 13, 2018.
Cardillo, T., "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Carl U. Bialucha et al: "Discovery and Optimization of HKT288, a Cadherin-6-Targeting ADC for the Treatment of Ovarian and Renal Cancers", Cancer Discovery, vol. 7, No. 9, Sep. 1, 2017 (Sep. 1, 2017), pp. 1030-1045, XP055484340.
Chi et al., "ETV1 is a lineage survival factor that cooperates with KIT in gastrointestinal stromal tumours," Nature, vol. 467, Oct. 14, 2010, pp. 849-855.
Chinese Office Action dated Nov. 1, 2016 in corresponding application No. 201380053256.2.
Chinese Office Action dated Nov. 8, 2019 for corresponding Application No. 201580019138.9—4 pages.
Chinese Search Report dated Jun. 24, 2020 for corresponding Application No. 108114649.
Cho et al., "Differential expression and function of cadherin-6 during renal epithelium development," Development, vol. 125, 1998, pp. 803-812.
Colombian Reconsideration Petition dated Mar. 15, 2018 in corresponding application No. NC2016/0000187.
Corada M et al: "Monoclonal antibodies directed to different regions of vascular endothelial cadherin extracellular domain affect adhesion and clustering of the protein and modulate endothelial permeability", Blood, the American Society of Hematology, US, vol. 97, No. 6, Mar. 15, 2001 (Mar. 15, 2001), pp. 1679-1684, XP002187985.
Corless et al., "Gastrointestinal stromal tumours: origin and molecular oncology," Nature Reviews, Cancer, vol. 11, Dec. 2011, pp. 865-878.
Coussens et al., "Tyrosine Kinase Receptor with Extensive Homology to EGF Receptor Shares Chromosomal Location with neu Oncogene," Science 230(4730):1132-1139 (Dec. 1985).
De Jager et al., "DX-8951f: Summary of Phase I Clinical Trials," Ann. N.Y. Acad. Sci., vol. 922, 2000, pp. 260-273.
Defazio et al., "Expression of c-erbB Receptors, Heregulin and Oestrogen Receptor in Human Breast Cell Lines," Int. J. Cancer 87:487-498 (2000)—12 Pages.
Demetri et al., "NCCN Task Force Report: Update on the Management of Patients with Gastrointestinal Stromal Tumors," Journal of the National Comprehensive Cancer Network, vol. 8, Supplement 2, Apr. 2010, pp. S-1-S-41.
Di Fiore et al., "erbB-2 Is a Potent Oncogene When Overexpressed in NIH/3T3 Cells," Science 237:178-182 (Jul. 1987).
Donaghy, Heather, "Effects of antibody, drug and linker on the preclinical and clinical toxicities of antibody-drug conjugates," mAbs, vol. 8, No. 4, 2016, pp. 659-671.
Dosio et al., "Antibody-targeted leucinostatin A", Journal of Controlled Release, No. 32, (1994), pp. 37-44.
El Sewedy et al., "Cloning of the Murine Trop2 Gene: Conservation of a PIP2-Binding Sequence in the Cytoplasmic Domain of Trop-2," Int. J. Cancer 75(2):324-330 (1998).
English-language translation of International Search Report issued in International Patent Application No. PCT/JP2015/002020 mailed Jul. 20, 2015.
Esteva et al., "A Phase II Study of Intravenous Exatecan Mesylate (DX-89511) Administered Daily for 5 Days Every 3 Weeks to Patients with Metastatic Breast Carcinoma", American Cancer Society,2003,900-907.
European Patent Office, "Extended European Search Report," issued in connection with European Patent Application No. 19206764.3., dated Feb. 4, 2020.
European Patent Office, "Communication with extended European Search Report," issued in connection with European Patent Application No. 13845596.9, dated May 6, 2016.
European Patent Office, "Communication with extended European Search Report," issued in connection with European Patent Application No. 13847461.4, dated May 13, 2016.
European Search Report issued in corresponding application No. 14874745.4 dated May 10, 2017.
Extended European Search Report dated Jan. 19, 2021 for corresponding European Patent Application No. 18802536.5.
Extended European Search Report dated Nov. 30, 2020 for corresponding European Patent Application No. 18742022.9.
Extended European Search Report issued in European Patent Application No. 15743738.5 dated Aug. 9, 2017.
Extended European Search Report issued in European Patent Application No. 15776810.2 dated Aug. 11, 2017.

(56) References Cited

OTHER PUBLICATIONS

Faulk et al., "Antigens of human trophoblasts: A working hypothesis for their role in normal and abnormal pregnancies," Proc. Natl. Acad. Sci. USA 75(4):1947-1951 (1978).
Fendly et al., "Characterization of Murine Monoclonal Antibodies Reactive to Either the Human Epidermal Growth Factor Receptor or HER2/neu Gene Product," Cancer Research 50:1550-1558 (1990).
Final Office Action issued in U.S. Appl. No. 15/221,851 mailed Nov. 13, 2017.
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Giridhar, "HER2-positive breast cancer: What is it?", Mayo Clinic, Mayo Foundation for Medical Education and Research (2020).
Goeppert et al., "Cadherin-6 is a putative tumor suppressor and target of epigenetically dysregulated miR-429 in cholangiocarcinoma," Epigenetics, vol. 11, No. 11, 2016, pp. 780-790.
Gomez-Monterrey et al., "Design, Synthesis, and Cytotoxic Evaluation of Acyl Derivatives of 3-Aminonaphtho[2,3-b]thiophene-4,9-dione, a Quinone-Based System," Journal of Medicinal Chemistry, 2011, 54(12):4077-4091, abstract.
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Gugnoni et al., "Cadherin-6 promotes EMT and cancer metastasis by restraining autophagy," Oncogene, vol. 36, 2017, pp. 667-677.
Haasen Dorothea et al: "G protein-coupled receptor internalization assays in the high-content screening format", Biomembranes: Transport Theory': Cells and Model Membranes; [Methods in Enzymology, ISSN 0076-6879], Elsevier, Academic Press, NL, vol. 414, Jan. 1, 2006 (Jan. 1, 2006), pp. 121-139.
Hardwick et al., "Immunohistochemical detection of p53 and c-erbB-2 in oesophageal carcinoma; no correlation with prognosis," Eur. J. Surg. Oncol. 23:30-35 (1997).
Hase et al., "Characterization of an Orphan G Protein-coupled Receptor, GPR20, That Constitutively Activates Gi Proteins*," the Journal of Biological Chemistry, vol. 283, No. 19, May 9, 2008, pp. 12747-12755.
Hinrichs et al., "Antibody Drug Conjugates: Nonclinical Safety Considerations," the AAPS Journal, vol. 17, No. 5, Sep. 2015, pp. 1055-1064.
Hirata T: "Producing monoclonal antibody of extracellular domain of metabotropic glutamate receptor 1, by hybridizing spleen cell of non-human animal immunized by olfactory tract, with myeloma cell, culturing hybridoma, screening culture supernatant", WPI/Thomson,, vol. 2004, No. 36, Apr. 22, 2004 (Apr. 22, 2004).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185HER2 causes transformation and tumorigenesis of NIH 3T3 cells," Proc. Natl. Acad. Sci. USA 84:7159-7163 (1987).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
IN Office Action issued in the corresponding Indian Patent Application Ser. No. 201647013640, dated Jul. 19, 2019.
Inoue et al., "Cadherin-6 Expression Transiently Delineates Specific Rhombomeres, Other Neural Tube Subdivisions, and Neural Crest Subpopulations in Mouse Embryos," Developmental Biology, vol. 183, 1997, pp. 183-194.
Inoue et al., "CM-Dextran-Polyalcohol-Camptothecin Conjugate: DE-310 with a Novel Carrier System and Its Preclinical Data," Polymer Drugs in the Clinical Stage, 2003, pp. 145-153.
Intellectual Property Office of Singapore, "Invitation to Respond to Written Opinion," Issued in connection with Singaporean Patent Application No. 11201502887W, dated Apr. 22, 2016.
International Search Report and Written Opinion for correspondence Application No. PCT/JP2018/007152 dated Apr. 24, 2018.
International Search Report for corresponding Application No. PCT/JP2014/006421 mailed Mar. 17, 2015.
International Search Report issued in International Patent Application No. PCT/JP2015/000355 mailed Apr. 21, 2015.
International Searching Authority, "International Search Report," issued in connection with International Patent Application No. PCT/JP2013/006069, dated Dec. 17, 2013.
International Searching Authority, "International Search Report," issued in connection with International Patent Application No. PCT/JP2013/006178, dated Dec. 17, 2013.
International Searching Authority, "International Search Report," issued in connection with International Patent Application No. PCT/JP2018/001065, dated Apr. 17, 2018.
International Searching Authority, "International Search Report," issued in connection with International Patent Application No. PCT/JP2018/018572, dated Aug. 7, 2018.
International Searching Authority, "Written Opinion," issued in connection with International Patent Application No. PCT/JP2018/001065, dated Apr. 17, 2018.
International Searching Authority, "Written Opinion," issued in connection with International Patent Application No. PCT/JP2018/018572, dated Aug. 7, 2018.
Janne, P., et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
Japanese Notice of Allowance dated Oct. 18, 2016 in corresponding application No. 2016-166850.
Japanese Office Action dated Dec. 6, 2016 in corresponding application No. 2016-540705.
Japanese Patent Office, "Decision to Grant a Patent," in connection with Japanese Patent Application No. 2016-166850, dated Oct. 18, 2016.
Japanese Patent Office, "Decision to Grant Patent," issued in connection with Japanese Patent Application No. 2016-117096, dated Jul. 4, 2017.
Japanese Patent Office, "Notification of Reasons for Refusal," in connection with Japanese Patent Application No. 2016-540705, dated Dec. 6, 2016.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer, vol. 72, 1997, pp. 680-686.
Kamath et al., "Challenges and advances in the assessment of the disposition of antibody-drug conjugates," Biopharmaceutics & Drug Disposition, 2015, 9 pages.
Kang et al, "Engineering multivalent antibodies to target heregulin-induced HER3 signaling in breast cancer cells, mAbs", Mar./Apr. 2014, vol. 6, No. 2, pp. 340-353.
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Kawakami et al—"The anti-HER3 antibody patritumab abrogates cetuximab resistance mediated by heregulin in colorectal cancer cells", Oncotarget, vol. 5, No. 23, Dec.-May 2014, 11847-11856—10 pages.

(56) References Cited

OTHER PUBLICATIONS

Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).

Koebel et al., "Ovarian Carcinoma Subtypes Are Different Diseases: Implications for Biomarker Studies," PLoS Medicine, vol. 5, Issue 12, e232, Dec. 2008, pp. 1749-1760.

Korkaya et al., "HER2 regulates the mammary stem/progenitor cell population driving tumorigenesis and invasion," Oncogene 27:6120-6130 (2008).

Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.

Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.

Kumazawa et al., "Antitumor activity of DX-8951f: a new camptothecin derivative," Exp. Opin. Invest. Drugs 7(4):625-632 (1998)—8 Pages.

Kumazawa et al., "DE-310, a novel macromolecular carrier system for the camptothecin analog DX-8951f: Potent antitumor activities in various murine tumor models," Cancer Sci., vol. 95, No. 2, Feb. 2004, pp. 168-175.

Kumazawa et al., "Potent and broad antitumor effects of DX-8951f, a water-soluble camptothecin derivative, against various human tumors xenografted in nude mice," Cancer Chemother. Pharmacol., vol. 42, 1998, pp. 210-220.

Linnenbach et al., "Sequence investigation of the major gastrointestinal tumor-associated antigen gene family, GA733," Proc. Natl. Acad. Sci. 86(1):27-31 (Jan. 1989).

Lipinski et al., "Human trophoblast cell-surface antigens defined by monoclonal antibodies," Proc. Natl. Acad. Sci. 78(8):5147-5150 (Aug. 1981).

Loo et al., "Development of an Fc-Enhanced Anti-B7-H3 Monoclonal Antibody with Potent Antitumor Activity," Clinical Cancer Research, vol. 18, No. 4, Jul. 15, 2012, pp. 3834-3845.

Mah et al., "Kidney Development in Cadherin-6 Mutants: Delayed Mesenchyme-to-Epithelial Conversion and Loss of Nephrons," Developmental Biology, vol. 223, 2000, pp. 38-53.

Martin et al., "Constitutive Activity among Orphan Class-A G Protein Coupled Receptors," PLOS One, Sep. 18, 2015, pp. 1-12.

Masubuchi, N., "Pharmacokinetics of DE-310, a novel macromolecular carrier system for the camptothecin analog DX-8951f, in tumor-bearing mice," Pharmazie, vol. 59, No. 5, 2004, pp. 374-377.

McDonagh et al., "Engineered antibody-drug conjugates with defined sites and stoichiometries of drug attachment," Protein Engineering, Design & Selection, 2006, 19(7):299-307.

Mitsui et al., "A New Water-soluble Camptothecin Derivative, DX-8951f, Exhibits Potent Antitumor Activity against Human Tumors in vitro and in vivo," Jpn. J. Cancer Res, vol. 86, Aug. 1995, pp. 776-782.

Moghaddas et al., "Whether HER2-positive non-breast cancers are candidates for treatment with Ado-trastuzumab emtansine?" Journal of Research in Pharmacy Practice, vol. 5, No. 4, Oct.-Dec. 2016, pp. 227-233.

Momoko Hase et al: Characterization of an Orphan G Protein-coupled Receptor, GPR20, That Constitutively Activates G i Proteins:, Journal of Biological Chemistry, vol. 283, No. 19, May 9, 2008 (May 9, 2008), pp. 12747-12755.

Mühlmann et al., "TROP2 expression as prognostic marker for gastric carcinoma," J. Clin. Pathol. 62(2):152-158 (2009).

Naidu et al., "Expression of c-erbB3 protein in primary breast carcinomas," British Journal of Cancer 78(10): 1385-1390 (1998)—6 Pages.

Nakada et al., "Novel antibody drug conjugates containing exatecan derivative-based cytotoxic payloads," Bioorganic & Medicinal Chemistry Letters, vol. 26, 2016, pp. 1542-1545.

Ning et al., "TROP2 expression and its correlation with tumor proliferation and angiogenesis in human gliomas," Neurol. Sci. 34(10):1745-1750 (2013).

Non-Final Office Action issued in U.S. Appl. No. 14/435,114 mailed Jul. 21, 2016.

Non-Final Office Action issued in U.S. Appl. No. 14/436,458 mailed Jul. 19, 2016.

Non-Final Office Action issued in U.S. Appl. No. 15/180,203 mailed Jul. 25, 2016.

Non-Final Office Action issued in U.S. Appl. No. 15/187,179 mailed Oct. 21, 2016.

Non-Final Office Action issued in U.S. Appl. No. 15/221,851 mailed Jul. 7, 2017.

Notice of Allowance issued in U.S. Appl. No. 15/221,851 mailed Jun. 13, 2018.

Notice of Allowance issued in U.S. Appl. No. 15/187,179 mailed Aug. 25, 2017.

Notice of Allowance issued in U.S. Appl. No. 15/187,179 mailed May 18, 2017.

Notice of Grounds for Rejection issued in connection with Korean Patent Application No. 10-2016-7015961, dated May 1, 2018.

O'Dowd et al., "Cloning and chromosomal mapping of four putative novel human G-protein-coupled receptor genes," Gene. vol. 187, 1997, pp. 75-81.

Ochi et al., "A possible mechanism for the long-lasting antitumor effect of the macromolecular conjugate DE-310: mediation by cellular uptake and drug release of its active camptothecin analog DX-8951," Cancer Chemother Pharmacol, vol. 55, 2005, pp. 323-332.

Office Action dated Apr. 16, 2021 for corresponding Brazilian Patent Application No. BR112015006521-0.

Office Action in corresponding application No. PCT/JP2017/036215 dated Nov. 21, 2017.

Office Action issued on Oct. 7, 2020 for corresponding Japanese Patent Application No. 2019-518773.

Office Action with Search Report dated Aug. 29, 2017, in RU 2015113767.

Ogitani et al., "Wide application of a novel topoisomerase I inhibitor-based drug conjugation technology," Bioorganic & Medicinal Chemistry Letters, vol. 26, 2016, 5069-5072.

Oguma et al., "Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry," Biomedical Chromatography, vol. 19, 2005, pp. 19-26.

Ohmachi et al., "Clinical Significance of TROP2 Expression in Colorectal Cancer," Clin. Cancer Res. 12(10):3057-3063 (May 15, 2006).

Opposition dated May 9, 2017, against CO NC2016/0000187, with partial English translation.

Osterhout et al., "Cadherin-6 Mediates Axon-Target Matching in a Non-Image-Forming Visual Circuit," Neuron Report, vol. 71, Aug. 25, 2011, pp. 632-639.

Paul et al., "Cadherin-6, a Cell Adhesion Molecule Specifically Expressed in the Proximal Renal Tubule and Renal Cell Carcinoma," Cancer Research, vol. 57, Jul. 1, 1997, pp. 2741-2748.

Perez et al., "Antibody-drug conjugates: current status and future directions," Drug Discovery Today, vol. 19, No. 7, Jul. 2014, pp. 869-881.

Peter's et al., "Antibody-drug conjugates as novel anti-cancer chemotherapeutics," Bioscience Reports, vol. 35, 2015, pp. 1-20.

Plowman et al., "Molecular cloning and expression of an additional epidermal growth factor receptor-related gene," Proc. Natl. Acad. Sci. USA 87:4905-4909 (Jul. 1990)—5 Pages.

Polakis, Paul, "Antibody Drug Conjugates for Cancer Therapy," Pharmacological Reviews, vol. 68, pp. 3-19, Jan. 2016.

Ripani et al., "Human Trop-2 is a Tumor-Associated Calcium Signal Transducer," Int. J. Cancer 76(5):671-676 (1998).

Rowinsky et al., "Preclinical and Clinical Development of Exatecan (DX-8951f), A Hexacyclic Camptothecin Analog," Camptothecins in Cancer Therapy, Chapter 14, 2005, pp. 317-341.

(56) References Cited

OTHER PUBLICATIONS

Russian Office Action dated Mar. 5, 2019 in corresponding application No. 2016143351.
Russian Office Action dated Oct. 11, 2018 in corresponding application No. 2016123597.
Scott et al., "Antibody therapy of cancer," Nature Reviews, vol. 12, Apr. 2012, pp. 278-287.
Search Report and Written Opinion dated Apr. 8, 2021 for corresponding Brazil Patent Application No. BR112016013482-6.
Search Report and Written Opinion dated Apr. 8, 2021 for corresponding Brazil Patent Application No. BR122020020973-9.
Sergina, N.V., et al. "Escape from HER-family tyrosine kinase inhibitor therapy by the kinase-inactive HER3", Nature, vol. 445, pp. 437-441, 2007 (6 pages).
Shen et al., "Conjugation site modulates the in vivo stability and therapeutic activity of antibody-drug conjugates," Nature Biotechnology, vol. 30, Jan. 22, 2012, pp. 184-189.
Shimazui et al., "The Level of Cadherin-6 mRNA in Peripheral Blood Is Associated with the Site of Metastasis and with the Subsequent Occurrence of Metastases in Renal Cell Carcinoma," Cancer, vol. 101, No. 5, Sep. 1, 2004, pp. 963-968.
Shimoyama et al., "Isolation and Sequence Analysis of Human Cadherin-6 Complementary DNA for the Full Coding Sequence and Its Expression in Human Carcinoma Cells," Cancer Research, vol. 55, May 15, 1995, pp. 2206-2211.
Shiose et al., "Systematic Research of Peptide Spacers Controlling Drug Release from Macromolecular Prodrug System, Carboxymethyldextran Polyalcohol-Peptide-Drug Conjugates," Bioconjugate Chem., vol. 20, 2009, pp. 60-70.
Shiose et al., "Relationship between Drug Release of DE-310, Macromolecular Prodrug of DX-8951f, and Cathepsins Activity in Several Tumors," Biol. Pharm. Bull., 2007, 30(12):2365-2370.
Sievers et al., "Antibody-Drug Conjugates in Cancer Therapy," Annual Review of Medicine, vol. 64, 2013, pp. 15-29.
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Nonclinical Studies Addressing the Mechanism of Action of Trastuzumab (Herceptin)," Semin. Oncol. 26(4) Suppl. 12: 60-70 (Aug. 1999).
Sliwkowski et al., "Coexpression of erbB2 and erbB3 Proteins Reconstitutes a High Affinity Receptor for Heregulin." J. Biol. Chem. 269(20):14661-14665 (1994).
Soepenberg et al., "Liquid chromatographic assays for DE-310, a novel camptothecin analog, and two major enzymatic products in human matrices," Journal of Chromatography B, vol. 799, 2004, pp. 15-22.
Soepenberg et al., "Phase I and Pharmacokinetic Study of DE-310 in Patients with Advanced Solid Tumors," Clin. Cancer Res. 11:703-711 (Jan. 15, 2005)—9 Pages.
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710. (Jul. 2011).
Taiwanese Office Action dated Jul. 30, 2018 in corresponding application No. 104111534.
Taiwanese Office Action dated May 15, 2017 in corresponding application No. 102136742.
Takiguchi et al., "Antitumor Effect of DX-8951, a Novel Camptothecin Analog, on Human Pancreatic Tumor Cells and Their CPT-11-resistant Variants Cultured in vitro and Xenografted in Nude Mice," Jpn. J. Cancer Res., vol. 88, Aug. 1997, pp. 760-769.
The State Intellectual Property Office of People's Republic of China, "The First Office Action," issued in connection with Chinese Patent Application No. 201380053256.2, dated Nov. 1, 2016.

The State Intellectual Property Office of People's Republic of China, "The First Office Action," issued in connection with Chinese Patent Application No. 201480071134.0, dated Aug. 20, 2019.
Tsuchikama et al., "Antibody-drug conjugates: recent advances in conjugation and linker chemistries," Protein & Cell, Oct. 14, 2016, 14 pages.
U.S. Patent and Trademark Office, "Non-Final Office Action", issued in connection with U.S. Appl. No. 15/821,662, dated Jan. 17, 2018.
United States Office Action dated Apr. 5, 2019 in U.S. Appl. No. 15/821,697.
US Patent and Trademark Office, "Notice of Allowance," issued in connection with U.S. Appl. No. 15/821,662, dated Nov. 2, 2018.
Velez et al., "APOE*E2 allele delays age of onset in PSEN1 E280A Alzheimer's disease," Molecular Psychiatry, 2015, pp. 1-9.
Vogel et al., "Efficacy and Safety of Trastuzumab as a Single Agent In First-Line Treatment of HER2-Overexpressing Metastatic Breast Cancer," J. Clin. Oncol. 20(3):719-726 (Feb. 2002).
Wang et al., "Identification of Trop-2 as an oncogene and an attractive therapeutic target in colon cancers," Mol. Cancer Ther. 7(2):280-285 (Feb. 2008).
Wente et al., "DE-310, a macromolecular prodrug of the topoisomerase-I-inhibitor exatecan (DX- 8951), in patients with operable solid tumors," Investigational New Drugs, vol. 23, 2005, pp. 339-347.
Yamaguchi, Teruhide, "Current situations and the future prospect of monoclonal antibody products," Report of the National Institute of Health, vol. 132, 2014, pp. 36-46.
Yano et al., "Comparison of HER2 gene amplification assessed by fluorescence in situ hybridization and HER2 protein expression assessed by immunohistochemistry in gastric cancer," Oncol. Rep. 15:65-71 (2006).
Yokoi et al., "A Novel Target Gene, SKP2, within the 5p13 Amplicon That Is Frequently Detected in Small Cell Lung Cancers," The American Journal of Pathology, vol. 161, Issue 1, Jul. 2002, pp. 207-216.
Yonesaka, K., et al., "Anti-HER3 monoclonal antibody patritumab sensitizes refractory non-small cell lung cancer to the epidermal growth factor receptor inhibitor erlotinib", Oncogene vol. 35, pp. 878-886, 2016 (10 pages).
Goldenberg et al., "Trop-2 is a novel target for solid cancer therapy with sacituzumab govitecan (IMMU-132), an antibody-drug conjugate (ADC)*", Oncotarget, Jun. 18, 2015, vol. 6, No. 26, pp. 22496-22512.
Office Action issued in corresponding Eurasian Patent Application No. 202490678 dated Aug. 15, 2024 (8 pages).
Office Action issued in corresponding Chinese Patent Application No. 201980064765.2 dated Jun. 1, 2024 (11 pages).
Office Action issued in corresponding Israeli Patent Application No. 280,510 dated May 12, 2024 (7 pages).
Office Action issued in corresponding Taiwanese Patent Application No. 112139757 dated May 17, 2024 (8 pages).
Search Report issued in connection with Eurasian Appl. No. 202490679 dated Jul. 2, 2024.
Search Report issued in connection with Eurasian Appl. No. 202490680 dated Jul. 2, 2024.
Search Report issued in connection with Eurasian Appl. No. 202490681 dated Jul. 2, 2024.
Hoon, Lee Seung, "[Internal Medicine] Diagnosis and Treatment of Brain Metastatic Cancer", MediForum, Jul. 31, 2009, pp. 1-11.
Nounou et al., "Anti-cancer antibody trastuzumab-melanotransferrin conjugate (BT2111) for the treatment of metastatic HER2 breast cancer tumors in the brain: An in-vivo study", Pharm Res., vol. 33, No. 12, Dec. 2016, pp. 2930-2942.
Office Action issued in corresponding Korean Patent Application No. 10-2021-7005657 dated Nov. 13, 2024.

* cited by examiner

[Figure 1]

SEQ ID NO: 1 - Amino acid sequence of a heavy chain of the anti-HER2 antibody

EVQLVESGGGLVQPGGSLRLSCAASGFNIKDTYIHWVR
QAPGKGLEWVARIYPTNGYTRYADSVKGRFTISADTSK
NTAYLQMNSLRAEDTAVYYCSRWGGDGFYAMDYWGQGT
LVTVSSASTKGPSVFPLAPSSKSTSGGTAALGCLVKDY
FPEPVTVSWNSGALTSGVHTFPAVLQSSGLYSLSSVVT
VPSSSLGTQTYICNVNHKPSNTKVDKKVEPKSCDKTHT
CPPCPAPELLGGPSVFLFPPKPKDTLMISRTPEVTCVV
VDVSHEDPEVKFNWYVDGVEVHNAKTKPREEQYNSTYR
VVSVLTVLHQDWLNGKEYKCKVSNKALPAPIEKTISKA
KGQPREPQVYTLPPSREEMTKNQVSLTCLVKGFYPSDI
AVEWESNGQPENNYKTTPPVLDSDGSFFLYSKLTVDKS
RWQQGNVFSCSVMHEALHNHYTQKSLSLSPGK

Variable region (1-120), Constant (121-450)

[Figure 2]

SEQ ID NO: 2 - Amino acid sequence of a light chain of the anti-HER2 antibody

DIQMTQSPSSLSASVGDRVTITCRASQDVNTAVAWYQQ
KPGKAPKLLIYSASFLYSGVPSRFSGSRSGTDFTLTIS
SLQPEDFATYYCQQHYTTPPTFGQGTKVEIKRTVAAPS
VFIFPPSDEQLKSGTASVVCLLNNFYPREAKVQWKVDN
ALQSGNSQESVTEQDSKDSTYSLSSTLTLSKADYEKHK
VYACEVTHQGLSSPVTKSFNRGEC

Variable region (1-107), Constant (108-214)

[Figure 3]

SEQ ID NO: 3 - Amino acid sequence of a heavy chain of the anti-HER3 antibody

QVQLQQWGAGLLKPSETLSLTCAVYGGSFSGYYWSWIR
QPPGKGLEWIGEINHSGSTNYNPSLKSRVTISVETSKN
QFSLKLSSVTAADTAVYYCARDKWTWYFDLWGRGTLVT
VSSASTKGPSVFPLAPSSKSTSGGTAALGCLVKDYFPE
PVTVSWNSGALTSGVHTFPAVLQSSGLYSLSSVVTVPS
SSLGTQTYICNVNHKPSNTKVDKRVEPKSCDKTHTCPP
CPAPELLGGPSVFLFPPKPKDTLMISRTPEVTCVVVDV
SHEDPEVKFNWYVDGVEVHNAKTKPREEQYNSTYRVVS
VLTVLHQDWLNGKEYKCKVSNKALPAPIEKTISKAKGQ
PREPQVYTLPPSREEMTKNQVSLTCLVKGFYPSDIAVE
WESNGQPENNYKTTPPVLDSDGSFFLYSKLTVDKSRWQ
QGNVFSCSVMHEALHNHYTQKSLSLSPGK

<u>Variable region (1-117), Constant (118-447)</u>

[Figure 4]

SEQ ID NO: 4 - Amino acid sequence of a light chain of the anti-HER3 antibody

DIEMTQSPDSLAVSLGERATINCRSSQSVLYSSSNRNY
LAWYQQNPGQPPKLLIYWASTRESGVPDRFSGSGSGTD
FTLTISSLQAEDVAVYYCQQYYSTPRTFGQGTKVEIKR
TVAAPSVFIFPPSDEQLKSGTASVVCLLNNFYPREAKV
QWKVDNALQSGNSQESVTEQDSKDSTYSLSSTLTLSKA
DYEKHKVYACEVTHQGLSSPVTKSFNRGEC

<u>Variable region (1-113), Constant (114-220)</u>

[Figure 5]

SEQ ID NO: 5 - Amino acid sequence of a heavy chain of the anti-TROP2 antibody

MKHLWFFLLLVAAPRWVLSQVQLVQSGAEVKKPGASVK
VSCKASGYTFTTAGMQWVRQAPGQGLEWMGWINTHSGV
PKYAEDFKGRVTISADTSTSTAYLQLSSLKSEDTAVYY
CARSGFGSSYWYFDVWGQGTLVTVSSASTKGPSVFPLA
PSSKSTSGGTAALGCLVKDYFPEPVTVSWNSGALTSGV
HTFPAVLQSSGLYSLSSVVTVPSSSLGTQTYICNVNHK
PSNTKVDKRVEPKSCDKTHTCPPCPAPELLGGPSVFLF
PPKPKDTLMISRTPEVTCVVVDVSHEDPEVKFNWYVDG
VEVHNAKTKPREEQYNSTYRVVSVLTVLHQDWLNGKEY
KCKVSNKALPAPIEKTISKAKGQPREPQVYTLPPSREE
MTKNQVSLTCLVKGFYPSDIAVEWESNGQPENNYKTTP
PVLDSDGSFFLYSKLTVDKSRWQQGNVFSCSVMHEALH
NHYTQKSLSLSPGK

Signal sequence (1-19), Variable region (20-140), Constant region (141-470)

[Figure 6]

SEQ ID NO: 6 - Amino acid sequence of a light chain of the anti-TROP2 antibody

MVLQTQVFISLLLWISGAYGDIQMTQSPSSLSASVGDR
VTITCKASQDVSTAVAWYQQKPGKAPKLLIYSASYRYT
GVPSRFSGSGSGTDFTLTISSLQPEDFAVYYCQQHYIT
PLTFGQGTKLEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), Variable region (21-129), Constant region (130-234)

[Figure 7]

SEQ ID NO: 7 - Amino acid sequence of a heavy chain of the anti-B7-H3 antibody

MKHLWFFLLLVAAPRWVLSQVQLVQSGAEVKKPGSSVK
VSCKASGYTFTNYVMHWVRQAPGQGLEWMGYINPYNDD
VKYNEKFKGRVTITADESTSTAYMELSSLRSEDTAVYY
CARWGYYGSPLYYFDYWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLSPGK

Signal sequence (1-19), Variable region (20-141), Constant region (142-471)

[Figure 8]

SEQ ID NO: 8 - Amino acid sequence of a light chain of the anti-B7-H3 antibody

MVLQTQVFISLLLWISGAYGEIVLTQSPATLSLSPGER
ATLSCRASSRLIYMHWYQQKPGQAPRPLIYATSNLASG
IPARFSGSGSGTDFTLTISSLEPEDFAVYYCQQWNSNP
PTFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), Variable region (21-128), Constant region (129-233)

[Figure 9]
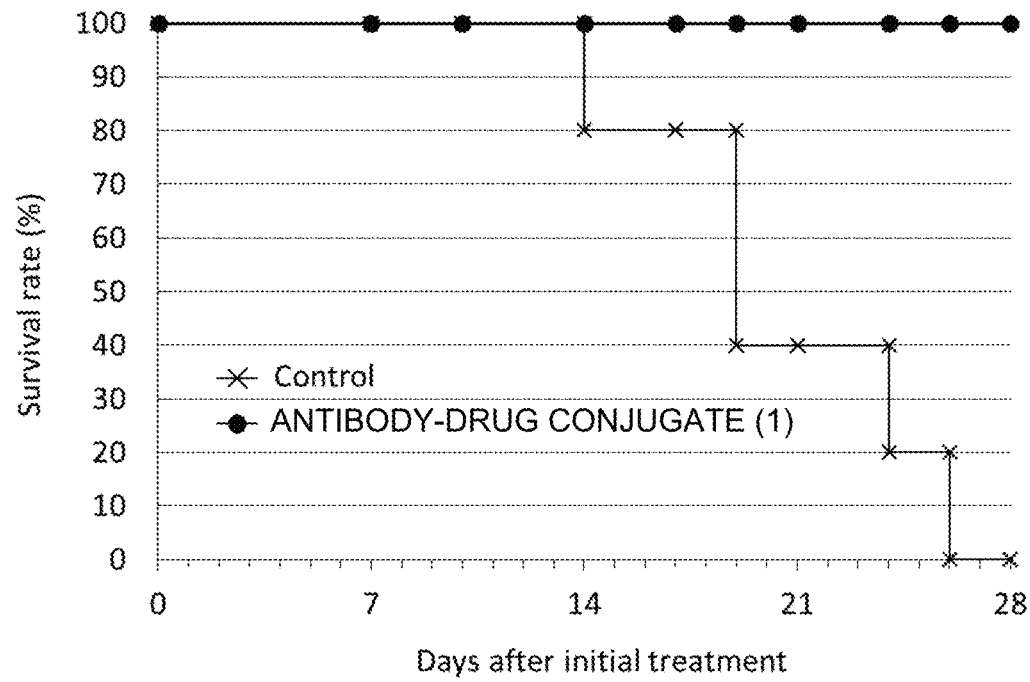
[Figure 10]
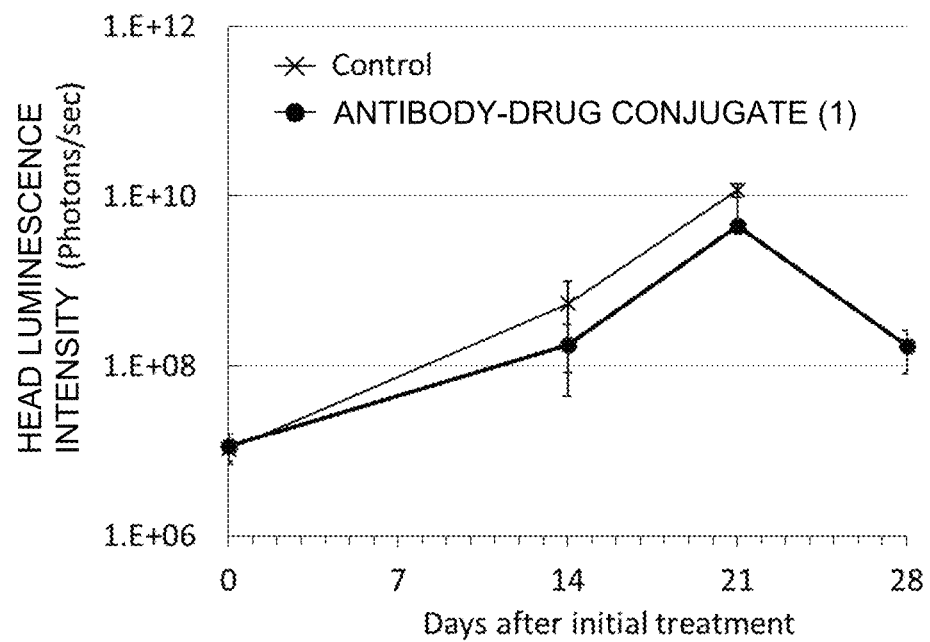

[Figure 11]
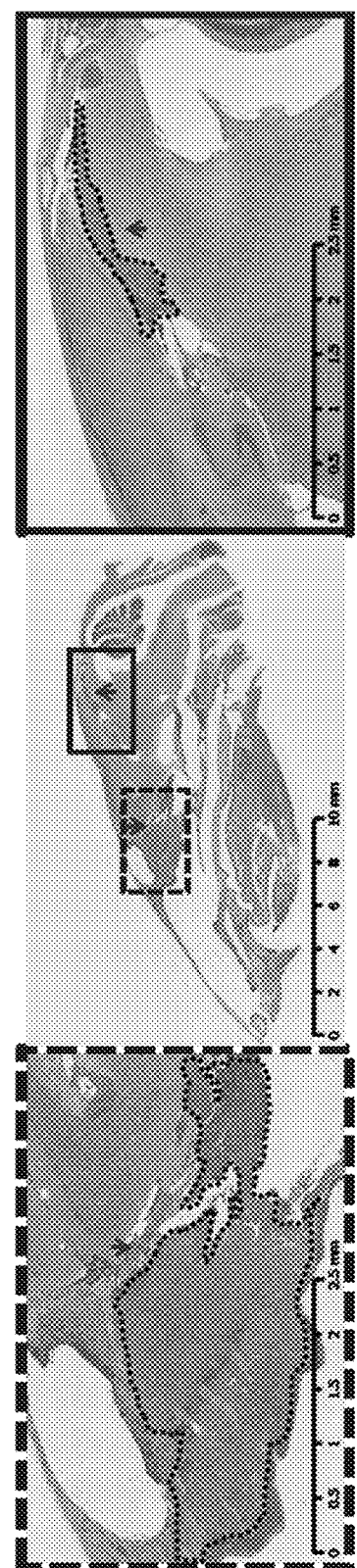
No. 1
No. 2

[Figure 12]

SEQ ID NO: 9 - Amino acid sequence of a heavy chain of the anti-GPR20 antibody

MKHLWFFLLLVAAPRWVLSEVQLVQSGAEVKKPGASVK
VSCKASGYTFTSYYISWIRQAPGQGLKYMGFINPGSGH
TNYNEKFKGRVTITADKSSTATMELSSLRSEDTAVYY
CARGAGGFLRIITKFDYWGQGTLVTVSSASTKGPSVFP
LAPSSKSTSGGTAALGCLVKDYFPEPVTVSWNSGALTS
GVHTFPAVLQSSGLYSLSSVVTVPSSSLGTQTYICNVN
HKPSNTKVDKRVEPKSCDKTHTCPPCPAPELLGGPSVF
LFPPKPKDTLMISRTPEVTCVVVDVSHEDPEVKFNWYV
DGVEVHNAKTKPREEQYNSTYRVVSVLTVLHQDWLNGK
EYKCKVSNKALPAPIEKTISKAKGQPREPQVYTLPPSR
EEMTKNQVSLTCLVKGFYPSDIAVEWESNGQPENNYKT
TPPVLDSDGSFFLYSKLTVDKSRWQQGNVFSCSVMHEA
LHNHYTQKSLSLSPGK

Signal sequence (1-19), Variable region (20-142), Constant region (143-472)

[Figure 13]

SEQ ID NO: 10 - Amino acid sequence of a light chain of the anti-GPR20 antibody

MVLQTQVFISLLLWISGAYGDTQLTQSPSSLSASVGDR
VTITCRASKSVSTYIHWYQQKPGKQPKLLIYSAGNLES
GVPSRFSGSGSGTDFTLTISSLQPEDFANYYCQQINEL
PYTFGQGTKVEIKRTVAAPSVFIFPPSDEQLKSGTASV
VCLLNNFYPREAKVQWKVDNALQSGNSQESVTEQDSKD
STYSLSSTLTLSKADYEKHKVYACEVTHQGLSSPVTKS
FNRGEC

Signal sequence (1-20), Variable region (21-129), Constant region (130-234)

[Figure 14]

SEQ ID NO: 11 - Amino acid sequence of a heavy chain of the anti-CDH6 antibody

MKHLWFFLLLVAAPRWVLSEVQLVQSGAEVKKPGASVK
VSCKASGYTFTRNFMHWVRQAPGQGLEWMGWIYPGDGE
TEYAQKFQGRVTITADTSTSTAYMELSSLRSEDTAVYY
CARGVYGGFAGGYFDFWGQGTLVTVSSASTKGPSVFPL
APSSKSTSGGTAALGCLVKDYFPEPVTVSWNSGALTSG
VHTFPAVLQSSGLYSLSSVVTVPSSSLGTQTYICNVNH
KPSNTKVDKRVEPKSCDKTHTCPPCPAPELLGGPSVFL
FPPKPKDTLMISRTPEVTCVVVDVSHEDPEVKFNWYVD
GVEVHNAKTKPREEQYNSTYRVVSVLTVLHQDWLNGKE
YKCKVSNKALPAPIEKTISKAKGQPREPQVYTLPPSRE
EMTKNQVSLTCLVKGFYPSDIAVEWESNGQPENNYKTT
PPVLDSDGSFFLYSKLTVDKSRWQQGNVFSCSVMHEAL
HNHYTQKSLSLSPGK

Signal sequence (1-19), Variable region (20-141), Constant region (142-471)

[Figure 15]

SEQ ID NO: 12 - Amino acid sequence of a light chain of the anti-CDH6 antibody

MVLQTQVFISLLLWISGAYGDIQMTQSPSSLSASVGDR
VTITCKASQNIYKNLAWYQQKPGKAPKLLIYDANTLQT
GVPSRFSGSGSGSDFTLTISSLQPEDFATYFCQQYYSG
WAFGQGTKVEIKRTVAAPSVFIFPPSDEQLKSGTASVV
CLLNNFYPREAKVQWKVDNALQSGNSQESVTEQDSKDS
TYSLSSTLTLSKADYEKHKVYACEVTHQGLSSPVTKSF
NRGEC

Signal sequence (1-20), Variable region (21-128), Constant region (129-233)

TREATMENT OF METASTATIC BRAIN TUMOR BY ADMINISTRATION OF AN ANTIBODY-DRUG CONJUGATE

CROSS-REFERENCE TO RELATED APPLICATIONS

The present application claims priority under 37 U.S.C. § 371 to International Patent Application No. PCT/JP2019/029765, filed Jul. 30, 2019, which claims priority to and the benefit of Japanese Patent Application No. 2018-143372, filed on Jul. 31, 2018. The contents of these applications are hereby incorporated by reference in their entireties.

SEQUENCE LISTING

The instant application contains a Sequence Listing which has been submitted in ASCII format via EFS-Web and is hereby incorporated by reference in its entirety. Said ASCII copy is named 122622-0130_SL.txt and is 37 kb in size.

TECHNICAL FIELD

The present invention relates to a therapeutic agent for a metastatic brain tumor comprising a specific antibody-drug conjugate, and/or a method of treatment for a metastatic brain tumor comprising administering a specific antibody-drug conjugate to a subject.

BACKGROUND ART

A metastatic brain tumor is a disease which develops when a primary cancer metastasizes to the brain and is known to occur in 20 to 40% of cancer patients. Cancer metastasis to the brain not only has a significant impact on prognosis but also leads to notable decline in QOL, and so the development of an effective method of treatment for a metastatic brain tumor is required (Non Patent References 1, 2).

As the primary cancer for metastatic brain tumors, lung cancer, breast cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma can be exemplified. Among these, it is known that particularly metastatic brain tumors originated from lung cancer, breast cancer and melanoma as primary cancers are present at high percentages (Non Patent References 1, 2).

For the treatment of metastatic brain tumors originated from lung cancer as a primary cancer, clinical studies using gefitinib (Non Patent Reference 3), erlotinib (Non Patent Reference 4), afatinib (Non Patent Reference 5) and osimertinib (Non Patent Reference 6), which are epidermal growth factor receptor (EGFR) tyrosine kinase inhibitors, and crizotinib (Non Patent Reference 7), which is an ALK inhibitor, or the like, are known.

For the treatment of metastatic brain tumors originated from breast cancer as a primary cancer, clinical studies using trastuzumab, which is an anti-HER2 antibody (Non Patent Reference 8), and lapatinib, which is a human epidermal growth factor receptor 2 (HER2) tyrosine kinase inhibitor (Non Patent Reference 9), or the like, are known.

For the treatment of metastatic brain tumors originated from melanoma as a primary cancer, clinical studies using vemurafenib, which is a BRAF inhibitor (Non Patent Reference 10), or the like, are known.

However, these drug therapies have not been established as the standard therapies, and radiotherapy and surgical therapy are considered as the first choice.

An antibody-drug conjugate (ADC) having a drug with cytotoxicity conjugated to an antibody capable of binding to an antigen expressed on the surface of cancer cells and cellular internalization, can deliver the drug selectively to cancer cells and can thus be expected to cause accumulation of the drug within cancer cells and to kill the cancer cells (Non-Patent References 11 to 15).

As one such antibody-drug conjugate, an antibody-drug conjugate comprising an antibody and a derivative of exatecan, which is a topoisomerase I inhibitor, as its components is known (Patent References 1 to 5, Non Patent References 16 to 19). These antibody-drug conjugates, which exert a superior antitumor effect and safety, are currently under clinical studies.

For the treatment of metastatic brain tumors using an antibody-drug conjugate, nonclinical and clinical studies of the treatment of metastatic brain tumors originated from breast cancer as a primary cancer using trastuzumab emtansine, which is an anti-HER2 antibody-drug conjugate having, as a component, DM1, which is a tubulin inhibitor, are known (Non Patent References 20 to 23).

CITATION LIST

Patent Literature

Patent Reference 1: International Publication No. WO 2014/057687
Patent Reference 2: International Publication No. WO 2015/098099
Patent Reference 3: International Publication No. WO 2015/115091
Patent Reference 4: International Publication No. WO 2015/155998
Patent Reference 5: International Publication No. WO 2018/066626

Non Patent Literature

Non Patent Reference 1: Lorenzo R., et al., Ther Adv Med Oncol. 2017 December; 9(12): 781-796.
Non Patent Reference 2: Rahmathulla G., et al., Journal of Oncology 2012, Article ID 723541.
Non Patent Reference 3: Kim J-E., et al., Lung Cancer 2009; 65: 351-354.
Non Patent Reference 4: Iuchi T., et al., Cancer 2013; 82: 282-287.
Non Patent Reference 5: Hoffknecht P., et al., J. Thorac. Oncol. 2015; 10: 156-163.
Non Patent Reference 6: Ahn M J., et al., Eur. J. Cancer 2015; 51: S625-S626.
Non Patent Reference 7: Costa D B., et al., J. Clin. Oncol. 2015; 33: 1881-1888.
Non Patent Reference 8: Bartsch R., et al., J. Neurooncol. 2007; 85: 311-317.
Non Patent Reference 9: Lin N U., et al., Clin. Cancer Res. 2009; 15: 1452-1459.
Non Patent Reference 10: Dummer R., et al., Eur. J. Cancer 2014; 50: 611-621.
Non Patent Reference 11: Ducry L., et al., Bioconjugate Chem. (2010) 21, 5-13.
Non Patent Reference 12: Alley S. C., et al., Current Opinion in Chemical Biology (2010) 14, 529-537.

Non Patent Reference 13: Damle N. K., Expert Opin. Biol. Ther. (2004) 4, 1445-1452.
Non Patent Reference 14: Senter P. D., et al., Nature Biotechnology (2012) 30, 631-637.
Non Patent Reference 15: Howard A., et al., J Clin Oncol 29: 398-405.
Non Patent Reference 16: Ogitani Y., et al., Clinical Cancer Research (2016) 22(20), 5097-5108.
Non Patent Reference 17: Ogitani Y., et al., Cancer Science (2016) 107, 1039-1046.
Non Patent Reference 18: Doi T., et al., Lancet Oncol 2017; 18: 1512-22.
Non Patent Reference 19: Takegawa N., et al., Int. J. Cancer: 141, 1682-1689 (2017)
Non Patent Reference 20: Bartsch R., et al., Clin. Exp. Metastasis (2015) 32:729-737.
Non Patent Reference 21: Askoxylakis V., et al., J. Natl. Cancer Inst. (2016) 108(2): djv313.
Non Patent Reference 22: Ricciardi G R R., et al., BMC Cancer (2018) 18:97.
Non Patent Reference 23: Okines A., et al., Breast J. 2018; 24:253-259.

SUMMARY OF INVENTION

Technical Problem

Low molecular weight compounds and antibodies are used as cancer therapeutic agents but it is usually difficult for these to pass through the blood-brain barrier (BBB). Particularly, since antibodies have extremely high molecular weight, they cannot be substantially expected to pass through the blood-brain barrier (Bendell J C., et al., Cancer 2003; 97(12):2972-7). On the other hand, there is a report that an antibody intravenously administered for the purpose of treating a metastatic brain tumor passed through the Blood-brain barrier (Tamura K., et al., J. Nucl. Med. 2013; 54(11):1869-75). The reason therefor is inferred to be that the blood-brain barrier had been destroyed by the tumor that had metastasized to the brain, and thus the ability of the antibody to migrate to the brain relatively increased.

However, there is also a report that even in the case where intracerebral concentrations of small molecule compound and antibody showed considerable values, an expected therapeutic effect was not obtained. The reason therefor is inferred to be that the tumor that had metastasized to the brain had acquired drug resistance (for example, a gene mutation affecting downstream signaling and drug elimination mechanisms, or the like, such as P glycoprotein) (Saunus J M., et al., J. Pathol. 2015; 237:363-78, Brastianos P K., et al., Cancer Discov. 2015; 5:1164-77).

Further, it is also known that a blood-tumor barrier (BTB) is formed between a tumor metastasized to the brain and normal tissues in the brain, whereby drug resistance appears (Quail D F. et al., Cancer Cell 2017; 31:326-41).

An object of the present invention is to verify whether or not a specific antibody-drug conjugate including a derivative of exatecan as a component passes through the blood-brain barrier and whether or not it exerts an intended antitumor effect on a metastatic brain tumor which has acquired drug resistance. Additionally, another object is to provide a therapeutic agent for a metastatic brain tumor comprising the antibody-drug conjugate, and/or a method of treatment for a metastatic brain tumor comprising administering the antibody-drug conjugate to a subject.

Solution to Problem

As a result of diligent studies in order to solve the above problems, the present inventors have found that a specific antibody-drug conjugate including a derivative of exatecan as a component exhibits an excellent antitumor effect on metastatic brain tumors, thereby accomplishing the present invention.

Thus, the present invention provides the following [1] to [272].

[1] A therapeutic agent for a metastatic brain tumor comprising, as an active component, an antibody-drug conjugate in which a drug-linker represented by the following formula:

[Formula 1]

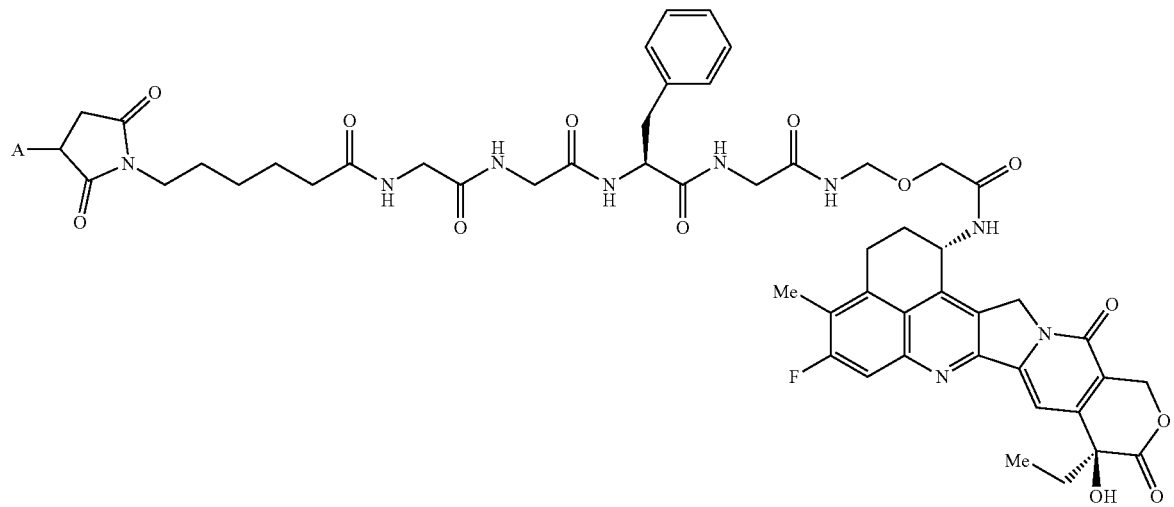

wherein A represents a connecting position to an antibody;
is conjugated to the antibody via a thioether bond.

[2] The therapeutic agent according to [1], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[3] The therapeutic agent according to [1], wherein the primary cancer for the metastatic brain tumor is at least one selected from the group consisting of breast cancer, lung cancer and melanoma.

[4] The therapeutic agent according to [1], wherein the primary cancer for the metastatic brain tumor is breast cancer.

[5] The therapeutic agent according to [1], wherein the primary cancer for the metastatic brain tumor is lung cancer.

[6] The therapeutic agent according to [1], wherein the primary cancer for the metastatic brain tumor is melanoma.

[7] The therapeutic agent according to any one of [1] to [6], wherein the antibody in the antibody-drug conjugate is an anti-HER2 antibody, an anti-HER3 antibody, an anti-TROP2 antibody, an anti-B7-H3 antibody, an anti-GPR20 antibody, or an anti-CDH6 antibody.

[8] The therapeutic agent according to [7], wherein the antibody in the antibody-drug conjugate is an anti-HER2 antibody.

[9] The therapeutic agent according to [8], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[10] The therapeutic agent according to [8], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[11] The therapeutic agent according to any one of [8] to [10], wherein the average number of units of the drug-linker conjugated per antibody molecule in the antibody-drug conjugate is in the range of from 7 to 8.

[12] The therapeutic agent according to [7], wherein the antibody in the antibody-drug conjugate is an anti-HER3 antibody.

[13] The therapeutic agent according to [12], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[14] The therapeutic agent according to [13], wherein the anti-HER3 antibody lacks a lysine residue at the carboxyl terminus of the heavy chain.

[15] The therapeutic agent according to any one of [12] to [14], wherein the average number of units of the drug-linker conjugated per antibody molecule in the antibody-drug conjugate is in the range of from 7 to 8.

[16] The therapeutic agent according to [7], wherein the antibody in the antibody-drug conjugate is an anti-TROP2 antibody.

[17] The therapeutic agent according to [16], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[18] The therapeutic agent according to [17], wherein the anti-TROP2 antibody lacks a lysine residue at the carboxyl terminus of the heavy chain.

[19] The therapeutic agent according to any one of [16] to [18], wherein the average number of units of the drug-linker conjugated per antibody molecule in the antibody-drug conjugate is in the range of from 3.5 to 4.5.

[20] The therapeutic agent according to [7], wherein the antibody in the antibody-drug conjugate is an anti-B7-H3 antibody.

[21] The therapeutic agent according to [20], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[22] The therapeutic agent according to [21], wherein the anti-B7-H3 antibody lacks a lysine residue at the carboxyl terminus of the heavy chain.

[23] The therapeutic agent according to any one of [20] to [22], wherein the average number of units of the drug-linker conjugated per antibody molecule in the antibody-drug conjugate is in the range of from 3.5 to 4.5.

[24] The therapeutic agent according to [7], wherein the antibody in the antibody-drug conjugate is an anti-GPR20 antibody.

[25] The therapeutic agent according to [24], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[26] The therapeutic agent according to [25], wherein the anti-GPR20 antibody lacks a lysine residue at the carboxyl terminus of the heavy chain.

[27] The therapeutic agent according to any one of [24] to [26], wherein the average number of units of the drug-linker conjugated per antibody molecule in the antibody-drug conjugate is in the range of from 7 to 8.

[28] The therapeutic agent according to [7], wherein the antibody in the antibody-drug conjugate is an anti-CDH6 antibody.

[29] The therapeutic agent according to [28], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[30] The therapeutic agent according to [29], wherein the anti-CDH6 antibody lacks a lysine residue at the carboxyl terminus of the heavy chain.

[31] The therapeutic agent according to any one of [28] to [30], wherein the average number of units of the drug-linker conjugated per antibody molecule in the antibody-drug conjugate is in the range of from 7 to 8.

[32] A therapeutic agent for a metastatic brain tumor comprising, as an active component, an antibody-drug conjugate represented by the following formula:

[Formula 2]

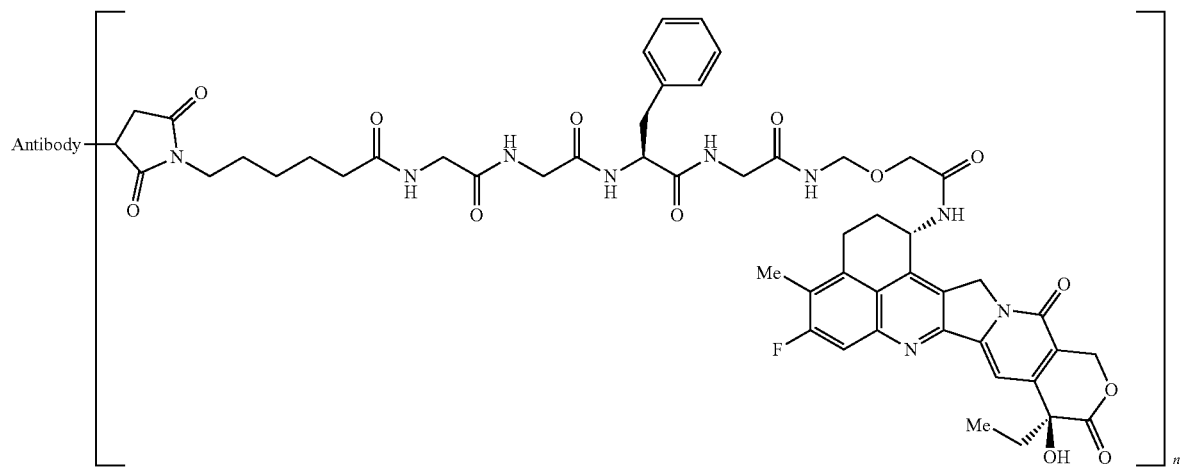

wherein the drug-linker is conjugated to the antibody via a thioether bond, and n is the average number of units of the drug-linker conjugated per antibody molecule.

[33] The therapeutic agent according to [32], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[34] The therapeutic agent according to [32], wherein the primary cancer for the metastatic brain tumor is at least one selected from the group consisting of breast cancer, lung cancer and melanoma.

[35] The therapeutic agent according to [32], wherein the primary cancer for the metastatic brain tumor is breast cancer.

[36] The therapeutic agent according to [32], wherein the primary cancer for the metastatic brain tumor is lung cancer.

[37] The therapeutic agent according to [32], wherein the primary cancer for the metastatic brain tumor is melanoma.

[38] The therapeutic agent according to any one of [32] to [37], wherein the antibody in the antibody-drug conjugate is an anti-HER2 antibody, an anti-HER3 antibody, an anti-TROP2 antibody, an anti-B7-H3 antibody, an anti-GPR20 antibody, or an anti-CDH6 antibody.

[39] The therapeutic agent according to [38], wherein the antibody in the antibody-drug conjugate is an anti-HER2 antibody.

[40] The therapeutic agent according to [39], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[41] The therapeutic agent according to [39], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[42] The therapeutic agent according to any one of [39] to [41], wherein the average number of units of the drug-linker conjugated per antibody molecule in the antibody-drug conjugate is in the range of from 7 to 8.

[43] The therapeutic agent according to [38], wherein the antibody in the antibody-drug conjugate is an anti-HER3 antibody.

[44] The therapeutic agent according to [43], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[45] The therapeutic agent according to [44], wherein the anti-HER3 antibody lacks a lysine residue at the carboxyl terminus of the heavy chain.

[46] The therapeutic agent according to any one of [43] to [45], wherein the average number of units of the drug-linker conjugated per antibody molecule in the antibody-drug conjugate is in the range of from 7 to 8.

[47] The therapeutic agent according to [38], wherein the antibody in the antibody-drug conjugate is an anti-TROP2 antibody.

[48] The therapeutic agent according to [47], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[49] The therapeutic agent according to [48], wherein the anti-TROP2 antibody lacks a lysine residue at the carboxyl terminus of the heavy chain.

[50] The therapeutic agent according to any one of 47 to 49, wherein the average number of units of the drug-linker conjugated per antibody molecule in the antibody-drug conjugate is in the range of from 3.5 to 4.5.

[51] The therapeutic agent according to [38], wherein the antibody in the antibody-drug conjugate is an anti-B7-H3 antibody.

[52] The therapeutic agent according to [51], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[53] The therapeutic agent according to [52], wherein the anti-B7-H3 antibody lacks a lysine residue at the carboxyl terminus of the heavy chain.

[54] The therapeutic agent according to any one of [51] to [53], wherein the average number of units of the drug-linker conjugated per antibody molecule in the antibody-drug conjugate is in the range of from 3.5 to 4.5.
[55] The therapeutic agent according to [38], wherein the antibody in the antibody-drug conjugate is an anti-GPR20 antibody.
[56] The therapeutic agent according to [55], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.
[57] The therapeutic agent according to [56], wherein the anti-GPR20 antibody lacks a lysine residue at the carboxyl terminus of the heavy chain.
[58] The therapeutic agent according to any one of [55] to [57], wherein the average number of units of the drug-linker conjugated per antibody molecule in the antibody-drug conjugate is in the range of from 7 to 8.
[59] The therapeutic agent according to [38], wherein the antibody in the antibody-drug conjugate is an anti-CDH6 antibody.
[60] The therapeutic agent according to [59], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.
[61] The therapeutic agent according to [60], wherein the anti-CDH6 antibody lacks a lysine residue at the carboxyl terminus of the heavy chain.
[62] The therapeutic agent according to any one of [59] to [61], wherein the average number of units of the drug-linker conjugated per antibody molecule in the antibody-drug conjugate is in the range of from 7 to 8.
[63] A method of treatment for a metastatic brain tumor, comprising administering an antibody-drug conjugate in which a drug-linker represented by the following formula:

wherein A represents a connecting position to an antibody, is conjugated to the antibody via a thioether bond; to a subject in need of the treatment for a metastatic brain tumor.
[64] The method of treatment according to [63], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.
[65] The method of treatment according to [63], wherein the primary cancer for the metastatic brain tumor is at least one selected from the group consisting of breast cancer, lung cancer and melanoma.
[66] The method of treatment according to [63], wherein the primary cancer for the metastatic brain tumor is breast cancer.
[67] The method of treatment according to [63], wherein the primary cancer for the metastatic brain tumor is lung cancer.
[68] The method of treatment according to [63], wherein the primary cancer for the metastatic brain tumor is melanoma.
[69] The method of treatment according to any one of [63] to [68], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.
[70] The method of treatment according to [69], wherein the antibody in the antibody-drug conjugate is an anti-HER2 antibody.
[71] The method of treatment according to [70], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.
[72] The method of treatment according to [70], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[Formula 3]

[73] The method of treatment according to any one of [70] to [72], wherein the average number of units of the drug-linker conjugated per antibody molecule in the antibody-drug conjugate is in the range of from 7 to 8.
[74] The method of treatment according to [69], wherein the antibody in the antibody-drug conjugate is an anti-HER3 antibody.
[75] The method of treatment according to [74], wherein the anti-HER3 antibody is an antibody comprising a heavy chain consisting of an amino acid sequence represented by SEQ ID NO: 3 and a light chain consisting of an amino acid sequence represented by SEQ ID NO: 4.
[76] The method of treatment according to [75], wherein the anti-HER3 antibody lacks a lysine residue at the carboxyl terminus of the heavy chain.
[77] The method of treatment according to any one of [74] to [76], wherein the average number of units of the drug-linker conjugated per antibody molecule in the antibody-drug conjugate is in the range of from 7 to 8.
[78] The method of treatment according to [69], wherein the antibody in the antibody-drug conjugate is an anti-TROP2 antibody.
[79] The method of treatment according to [78], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.
[80] The method of treatment according to [79], wherein the anti-TROP2 antibody lacks a lysine residue at the carboxyl terminus of the heavy chain.
[81] The method of treatment according to any one of [78] to [80], wherein the average number of units of the drug-linker conjugated per antibody molecule in the antibody-drug conjugate is in the range of from 3.5 to 4.5.
[82] The method of treatment according to [69], wherein the antibody in the antibody-drug conjugate is an anti-B7-H3 antibody.
[83] The method of treatment according to [82], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.
[84] The method of treatment according to [83], wherein the anti-B7-H3 antibody lacks a lysine residue at the carboxyl terminus of the heavy chain.
[85] The method of treatment according to any one of [82] to [84], wherein the average number of units of the drug-linker conjugated per antibody molecule in the antibody-drug conjugate is in the range of from 3.5 to 4.5.
[86] The method of treatment according to [69], wherein the antibody in the antibody-drug conjugate is an anti-GPR20 antibody.
[87] The method of treatment according to [86], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.
[88] The method of treatment according to [87], wherein the anti-GPR20 antibody lacks a lysine residue at the carboxyl terminus of the heavy chain.
[89] The method of treatment according to any one of [86] to [88], wherein the average number of units of the drug-linker conjugated per antibody molecule in the antibody-drug conjugate is in the range of from 7 to 8.
[90] The method of treatment according to [69], wherein the antibody in the antibody-drug conjugate is an anti-CDH6 antibody.
[91] The method of treatment according to [90], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.
[92] The method of treatment according to [91], wherein the anti-CDH6 antibody lacks a lysine residue at the carboxyl terminus of the heavy chain.
[93] The method of treatment according to any one of [90] to [92], wherein the average number of units of the drug-linker conjugated per antibody molecule in the antibody-drug conjugate is in the range of from 7 to 8.
[94] A method of treatment for a metastatic brain tumor, comprising administering an antibody-drug conjugate represented by the following formula:

[Formula 4]

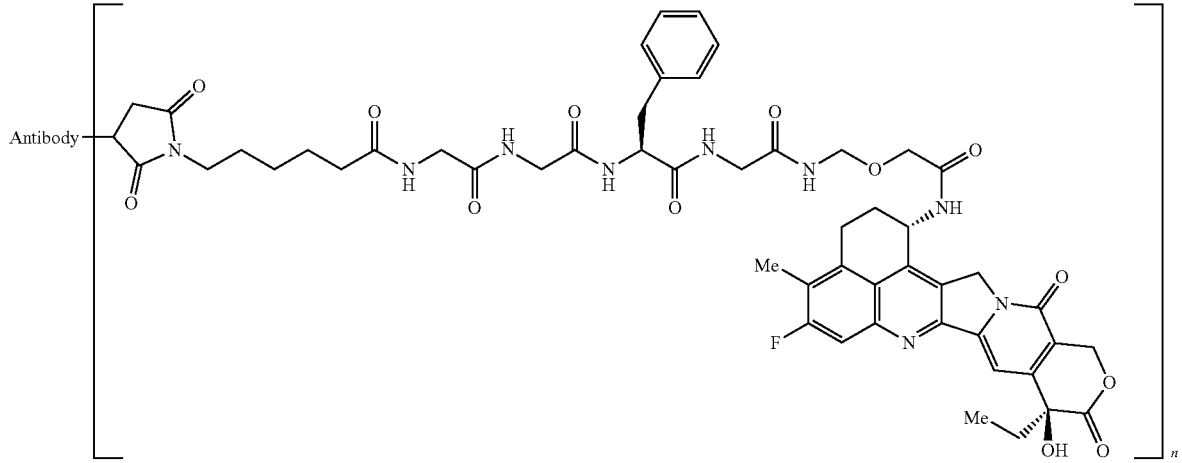

wherein the drug-linker is conjugated to the antibody via a thioether bond, and n is the average number of units of the drug-linker conjugated per antibody molecule; to a subject in need of the treatment for a metastatic brain tumor.

[95] The method of treatment according to [94], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[96] The method of treatment according to [94], wherein the primary cancer for the metastatic brain tumor is at least one selected from the group consisting of breast cancer, lung cancer and melanoma.

[97] The method of treatment according to [94], wherein the primary cancer for the metastatic brain tumor is breast cancer.

[98] The method of treatment according to [94], wherein the primary cancer for the metastatic brain tumor is lung cancer.

[99] The method of treatment according to [94], wherein the primary cancer for the metastatic brain tumor is melanoma.

[100] The method of treatment according to any one of [94] to [99], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[101] The method of treatment according to [100], wherein the antibody in the antibody-drug conjugate is an anti-HER2 antibody.

[102] The method of treatment according to [101], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[103] The method of treatment according to [101], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[104] The method of treatment according to any one of [101] to [103], wherein the average number of units of the drug-linker conjugated per antibody molecule in the antibody-drug conjugate is in the range of from 7 to 8.

[105] The method of treatment according to [100], wherein the antibody in the antibody-drug conjugate is an anti-HER3 antibody.

[106] The method of treatment according to [105], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[107] The method of treatment according to [106], wherein the anti-HER3 antibody lacks a lysine residue at the carboxyl terminus of the heavy chain.

[108] The method of treatment according to any one of [105] to [107], wherein the average number of units of the drug-linker conjugated per antibody molecule in the antibody-drug conjugate is in the range of from 7 to 8.

[109] The method of treatment according to [100], wherein the antibody in the antibody-drug conjugate is an anti-TROP2 antibody.

[110] The method of treatment according to [109], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[111] The method of treatment according to [110], wherein the anti-TROP2 antibody lacks a lysine residue at the carboxyl terminus of the heavy chain.

[112] The method of treatment according to any one of [109] to [111], wherein the average number of units of the drug-linker conjugated per antibody molecule in the antibody-drug conjugate is in the range of from 3.5 to 4.5.

[113] The method of treatment according to [100], wherein the antibody in the antibody-drug conjugate is an anti-B7-H3 antibody.

[114] The method of treatment according to [113], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[115] The method of treatment according to [114], wherein the anti-B7-H3 antibody lacks a lysine residue at the carboxyl terminus of the heavy chain.

[116] The method of treatment according to any one of [113] to [115], wherein the average number of units of the drug-linker conjugated per antibody molecule in the antibody-drug conjugate is in the range of from 3.5 to 4.5.

[117] The method of treatment according to [100], wherein the antibody in the antibody-drug conjugate is an anti-GPR20 antibody.

[118] The method of treatment according to [117], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[119] The method of treatment according to [118], wherein the anti-GPR20 antibody lacks a lysine residue at the carboxyl terminus of the heavy chain.

[120] The method of treatment according to any one of [117] to [119], wherein the average number of units of the drug-linker conjugated per antibody molecule in the antibody-drug conjugate is in the range of from 7 to 8.

[121] The method of treatment according to [100], wherein the antibody in the antibody-drug conjugate is an anti-CDH6 antibody.

[122] The method of treatment according to [121], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[123] The method of treatment according to [122], wherein the anti-CDH6 antibody lacks a lysine residue at the carboxyl terminus of the heavy chain.

[124] The method of treatment according to any one of [121] to [123], wherein the average number of units of the drug-linker conjugated per antibody molecule in the antibody-drug conjugate is in the range of from 7 to 8.

[125] An antibody-drug conjugate, for use in treating a metastatic brain tumor, in which a drug-linker represented by the following formula:

[Formula 5]

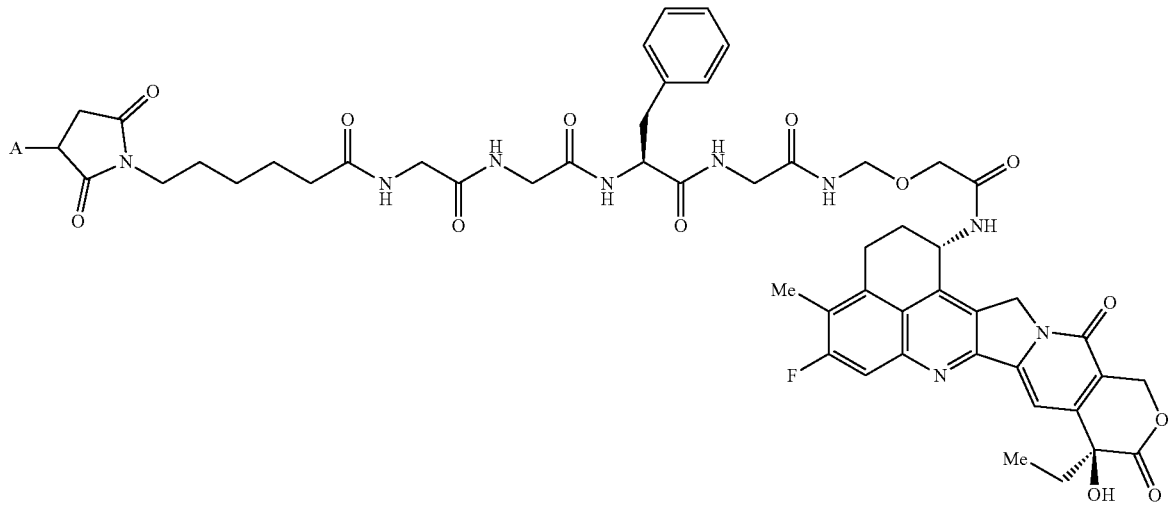

wherein A represents a connecting position to an antibody;
is conjugated to the antibody via a thioether bond.

[126] The antibody-drug conjugate according to [125], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[127] The antibody-drug conjugate according to [125], wherein the primary cancer for the metastatic brain tumor is at least one selected from the group consisting of breast cancer, lung cancer and melanoma.

[128] The antibody-drug conjugate according to [125], wherein the primary cancer for the metastatic brain tumor is breast cancer.

[129] The antibody-drug conjugate according to [125], wherein the primary cancer for the metastatic brain tumor is lung cancer.

[130] The antibody-drug conjugate according to [125], wherein the primary cancer for the metastatic brain tumor is melanoma.

[131] The antibody-drug conjugate according to any one of [125] to [130], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[132] The antibody-drug conjugate according to [131], wherein the antibody in the antibody-drug conjugate is an anti-HER2 antibody

[133] The antibody-drug conjugate according to [132], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[134] The antibody-drug conjugate according to [132], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[135] The antibody-drug conjugate according to any one of [132] to [134], wherein the average number of units of the drug-linker conjugated per antibody molecule in the antibody-drug conjugate is in the range of from 7 to 8.

[136] The antibody-drug conjugate according to [131], wherein the antibody in the antibody-drug conjugate is an anti-HER3 antibody.

[137] The antibody-drug conjugate according to [136], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[138] The antibody-drug conjugate according to [137], wherein the anti-HER3 antibody lacks a lysine residue at the carboxyl terminus of the heavy chain.

[139] The antibody-drug conjugate according to any one of [136] to [138], wherein the average number of units of the drug-linker conjugated per antibody molecule in the antibody-drug conjugate is in the range of from 7 to 8.

[140] The antibody-drug conjugate according to [131], wherein the antibody in the antibody-drug conjugate is an anti-TROP2 antibody.

[141] The antibody-drug conjugate according to [140], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[142] The antibody-drug conjugate according to [141], wherein the anti-TROP2 antibody lacks a lysine residue at the carboxyl terminus of the heavy chain.

[143] The antibody-drug conjugate according to any one of [140] to [142], wherein the average number of units of the drug-linker conjugated per antibody molecule in the antibody-drug conjugate is in the range of from 3.5 to 4.5.

[144] The antibody-drug conjugate according to [131], wherein the antibody in the antibody-drug conjugate is an anti-B7-H3 antibody.

[145] The antibody-drug conjugate according to [144], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[146] The antibody-drug conjugate according to [145], wherein the anti-B7-H3 antibody lacks a lysine residue at the carboxyl terminus of the heavy chain.

[147] The antibody-drug conjugate according to any one of [144] to [146], wherein the average number of units of the drug-linker conjugated per antibody molecule in the antibody-drug conjugate is in the range of from 3.5 to 4.5.

[148] The antibody-drug conjugate according to [131], wherein the antibody in the antibody-drug conjugate is an anti-GPR20 antibody.

[149] The antibody-drug conjugate according to [148], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[150] The antibody-drug conjugate according to [149], wherein the anti-GPR20 antibody lacks a lysine residue at the carboxyl terminus of the heavy chain.

[151] The antibody-drug conjugate according to any one of [148] to [150], wherein the average number of units of the drug-linker conjugated per antibody molecule in the antibody-drug conjugate is in the range of from 7 to 8.

[152] The antibody-drug conjugate according to [131], wherein the antibody in the antibody-drug conjugate is an anti-CDH6 antibody.

[153] The antibody-drug conjugate according to [152], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[154] The antibody-drug conjugate according to [153], wherein the anti-CDH6 antibody lacks a lysine residue at the carboxyl terminus of the heavy chain.

[155] The antibody-drug conjugate according to any one of [152] to [154], wherein the average number of units of the drug-linker conjugated per antibody molecule in the antibody-drug conjugate is in the range of from 7 to 8.

[156] An antibody-drug conjugate, for use in treating a metastatic brain tumor, represented by the following formula:

[Formula 6]

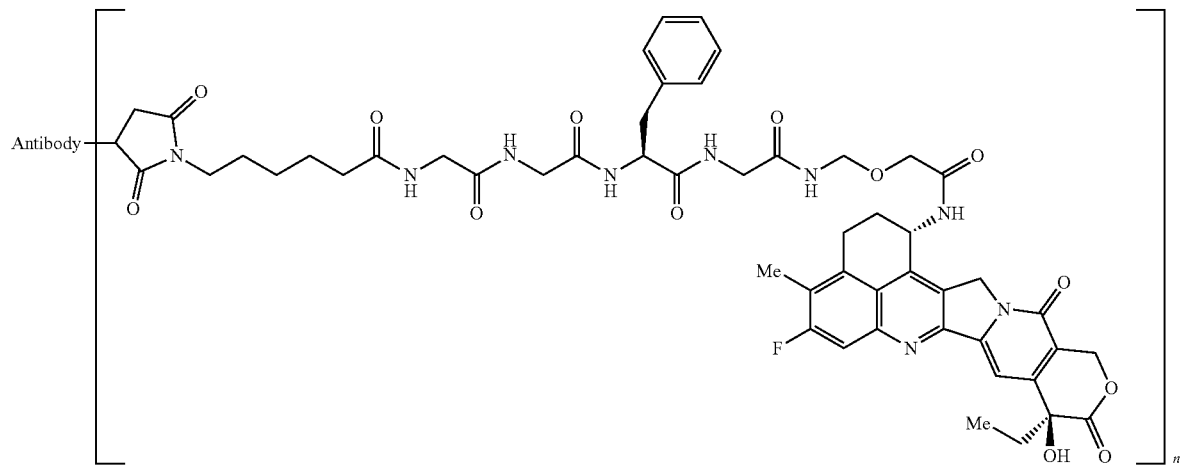

wherein the drug-linker is conjugated to the antibody via a thioether bond, and n is the average number of units of the drug-linker conjugated per antibody molecule.

[157] The antibody-drug conjugate according to [156], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[158] The antibody-drug conjugate according to [156], wherein the primary cancer for the metastatic brain tumor is at least one selected from the group consisting of breast cancer, lung cancer and melanoma.

[159] The antibody-drug conjugate according to [156], wherein the primary cancer for the metastatic brain tumor is breast cancer.

[160] The antibody-drug conjugate according to [156], wherein the primary cancer for the metastatic brain tumor is lung cancer.

[161] The antibody-drug conjugate according to [156], wherein the primary cancer for the metastatic brain tumor is melanoma.

[162] The antibody-drug conjugate according to any one of [156] to [161], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[163] The antibody-drug conjugate according to [162], wherein the antibody in the antibody-drug conjugate is an anti-HER2 antibody.

[164] The antibody-drug conjugate according to [163], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[165] The antibody-drug conjugate according to [163], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[166] The antibody-drug conjugate according to any one of [163] to [165], wherein the average number of units of the drug-linker conjugated per antibody molecule in the antibody-drug conjugate is in the range of from 7 to 8.

[167] The antibody-drug conjugate according to [162], wherein the antibody in the antibody-drug conjugate is an anti-HER3 antibody.

[168] The antibody-drug conjugate according to [167], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[169] The antibody-drug conjugate according to [168], wherein the anti-HER3 antibody lacks a lysine residue at the carboxyl terminus of the heavy chain.

[170] The antibody-drug conjugate according to any one of [167] to [169], wherein the average number of units of the drug-linker conjugated per antibody molecule in the antibody-drug conjugate is in the range of from 7 to 8.

[171] The antibody-drug conjugate according to [162], wherein the antibody in the antibody-drug conjugate is an anti-TROP2 antibody.

[172] The antibody-drug conjugate according to [171], wherein the anti-TROP2 antibody is an antibody comprising a heavy chain consisting of an amino acid sequence consisting of amino acid residues 20 to 470 of SEQ ID NO: and a light chain consisting of an amino acid sequence consisting of amino acid residues 21 to 234 of SEQ ID NO: 6.

[173] The antibody-drug conjugate according to [172], wherein the anti-TROP2 antibody lacks a lysine residue at the carboxyl terminus of the heavy chain.

[174] The antibody-drug conjugate according to any one of [171] to [173], wherein the average number of units of the drug-linker conjugated per antibody molecule in the antibody-drug conjugate is in the range of from 3.5 to 4.5.

[175] The antibody-drug conjugate according to [162], wherein the antibody in the antibody-drug conjugate is an anti-B7-H3 antibody.

[176] The antibody-drug conjugate according to [175], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[177] The antibody-drug conjugate according to [176], wherein the anti-B7-H3 antibody lacks a lysine residue at the carboxyl terminus of the heavy chain.

[178] The antibody-drug conjugate according to any one of [175] to [177], wherein the average number of units of the drug-linker conjugated per antibody molecule in the antibody-drug conjugate is in the range of from 3.5 to 4.5.

[179] The antibody-drug conjugate according to [162], wherein the antibody in the antibody-drug conjugate is an anti-GPR20 antibody.

[180] The antibody-drug conjugate according to [179], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[181] The antibody-drug conjugate according to [180], wherein the anti-GPR20 antibody lacks a lysine residue at the carboxyl terminus of the heavy chain.

[182] The antibody-drug conjugate according to any one of [179] to [181], wherein the average number of units of the drug-linker conjugated per antibody molecule in the antibody-drug conjugate is in the range of from 7 to 8.

[183] The antibody-drug conjugate according to [162], wherein the antibody in the antibody-drug conjugate is an anti-CDH6 antibody.

[184] The antibody-drug conjugate according to [183], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[185] The antibody-drug conjugate according to [184], wherein the anti-CDH6 antibody lacks a lysine residue at the carboxyl terminus of the heavy chain.

[186] The antibody-drug conjugate according to any one of [183] to [185], wherein the average number of units of the drug-linker conjugated per antibody molecule in the antibody-drug conjugate is in the range of from 7 to 8.

[187] Use of an antibody-drug conjugate for the manufacture of a medicament for treating a metastatic brain tumor, in which a drug-linker represented by the following formula:

[Formula 7]

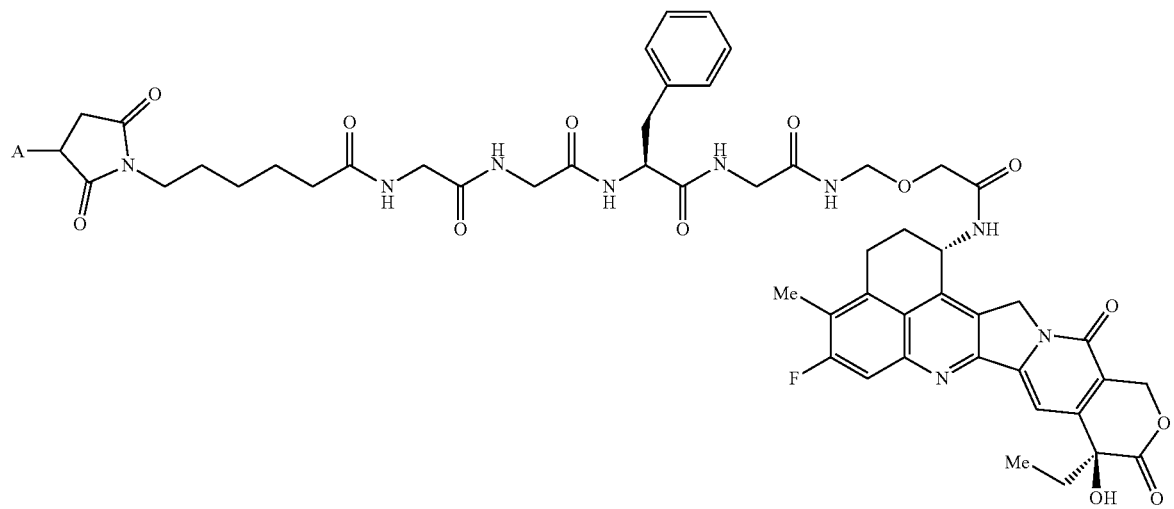

wherein A represents a connecting position to an antibody;
is conjugated to the antibody via a thioether bond.

[188] The use according to [187], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma.

[189] The use according to [187], wherein the primary cancer for the metastatic brain tumor is at least one selected from the group consisting of breast cancer, lung cancer and melanoma.

[190] The use according to [187], wherein the primary cancer for the metastatic brain tumor is breast cancer.

[191] The use according to [187], wherein the primary cancer for the metastatic brain tumor is lung cancer.

[192] The use according to [187], wherein the primary cancer for the metastatic brain tumor is melanoma.

[193] The use according to any one of [187] to [192], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[194] The use according to [193], wherein the antibody in the antibody-drug conjugate is an anti-HER2 antibody.

[195] The use according to [194], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[196] The use according to [194], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[197] The use according to any one of [194] to [196], wherein the average number of units of the drug-linker conjugated per antibody molecule in the antibody-drug conjugate is in the range of from 7 to 8.

[198] The use according to [193], wherein the antibody in the antibody-drug conjugate is an anti-HER3 antibody.

[199] The use according to [198], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[200] The use according to [199], wherein the anti-HER3 antibody lacks a lysine residue at the carboxyl terminus of the heavy chain.

[201] The use according to any one of [198] to [200], wherein the average number of units of the drug-linker conjugated per antibody molecule in the antibody-drug conjugate is in the range of from 7 to 8.

[202] The use according to [193], wherein the antibody in the antibody-drug conjugate is an anti-TROP2 antibody.

[203] The use according to [202], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[204] The use according to [203], wherein the anti-TROP2 antibody lacks a lysine residue at the carboxyl terminus of the heavy chain.

[205] The use according to any one of [202] to [204], wherein the average number of units of the drug-linker conjugated per antibody molecule in the antibody-drug conjugate is in the range of from 3.5 to 4.5.

[206] The use according to [193], wherein the antibody in the antibody-drug conjugate is an anti-B7-H3 antibody.

[207] The use according to [206], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[208] The use according to [207], wherein the anti-B7-H3 antibody lacks a lysine residue at the carboxyl terminus of the heavy chain.

[209] The use according to any one of [206] to [208], wherein the average number of units of the drug-linker conjugated per antibody molecule in the antibody-drug conjugate is in the range of from 3.5 to 4.5.

[210] The use according to [193], wherein the antibody in the antibody-drug conjugate is an anti-GPR20 antibody.

[211] The use according to [210], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[212] The use according to [211], wherein the anti-GPR20 antibody lacks a lysine residue at the carboxyl terminus of the heavy chain.

[213] The use according to any one of [210] to [212], wherein the average number of units of the drug-linker conjugated per antibody molecule in the antibody-drug conjugate is in the range of from 7 to 8.

[214] The use according to [193], wherein the antibody in the antibody-drug conjugate is an anti-CDH6 antibody.

[215] The use according to [214], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[216] The use according to [215], wherein the anti-CDH6 antibody lacks a lysine residue at the carboxyl terminus of the heavy chain.

[217] The use according to any one of [214] to [216], wherein the average number of units of the drug-linker conjugated per antibody molecule in the antibody-drug conjugate is in the range of from 7 to 8.

[218] Use of an antibody-drug conjugate for the manufacture of a medicament for treating a metastatic brain tumor, represented by the following formula:

cancer, pancreatic cancer, endometrial cancer, thyroid cancer, malignant lymphoma and sarcoma.

[220] The use according to [218], wherein the primary cancer for the metastatic brain tumor is at least one selected from the group consisting of breast cancer, lung cancer and melanoma.

[221] The use according to [218], wherein the primary cancer for the metastatic brain tumor is breast cancer.

[222] The use according to [218], wherein the primary cancer for the metastatic brain tumor is lung cancer.

[223] The use according to [218], wherein the primary cancer for the metastatic brain tumor is melanoma.

[224] The use according to any one of [218] to [223], wherein the antibody in the antibody-drug conjugate is an anti-HER2 antibody, an anti-HER3 antibody, an anti-TROP2 antibody, an anti-B7-H3 antibody, an anti-GPR20 antibody or an anti-CDH6 antibody.

[225] The use according to [224], wherein the antibody in the antibody-drug conjugate is an anti-HER2 antibody.

[226] The use according to [225], wherein the anti-HER2 antibody is an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.

[227] The use according to [225], wherein the anti-HER2 antibody is an antibody comprising a heavy chain consisting of an amino acid sequence represented by SEQ ID NO: 1 and a light chain consisting of an amino acid sequence represented by SEQ ID NO: 2.

[228] The use according to any one of [225] to [227], wherein the average number of units of the drug-linker conjugated per antibody molecule in the antibody-drug conjugate is in the range of from 7 to 8.

[Formula 8]

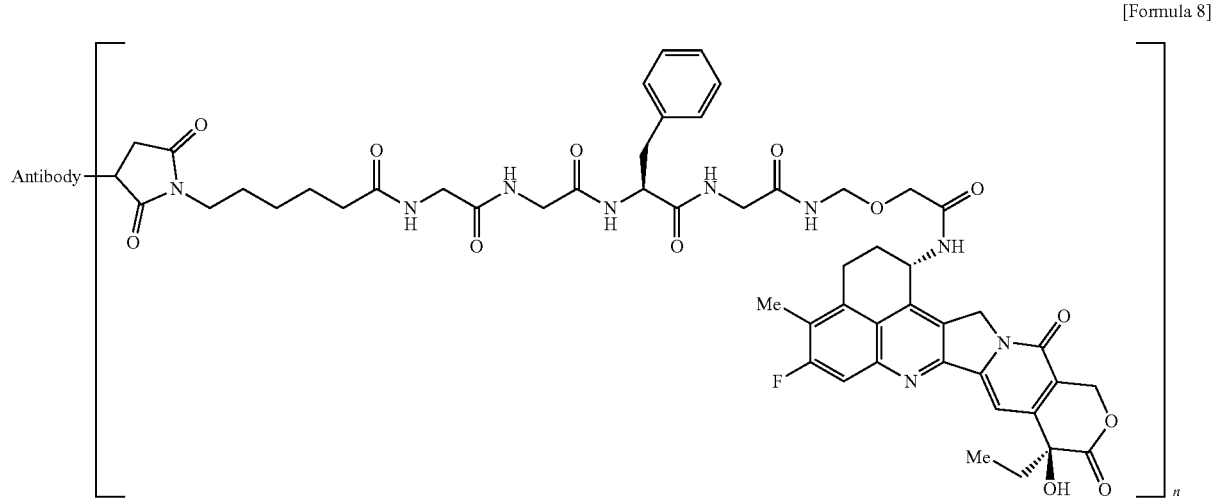

wherein the drug-linker is conjugated to the antibody via a thioether bond, and n is the average number of units of the drug-linker conjugated per antibody molecule.

[219] The use according to [218], wherein the primary cancer for the metastatic brain tumor is at least one selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder

[229] The use according to [224], wherein the antibody in the antibody-drug conjugate is an anti-HER3 antibody.

[230] The use according to [229], wherein the anti-HER3 antibody is an antibody comprising a heavy chain consisting of an amino acid sequence represented by SEQ ID NO: 3 and a light chain consisting of an amino acid sequence represented by SEQ ID NO: 4.

[231] The use according to [230], wherein the anti-HER3 antibody lacks a lysine residue at the carboxyl terminus of the heavy chain.

[232] The use according to any one of [229] to [231], wherein the average number of units of the drug-linker conjugated per antibody molecule in the antibody-drug conjugate is in the range of from 7 to 8.

[233] The use according to [224], wherein the antibody in the antibody-drug conjugate is an anti-TROP2 antibody.

[234] The use according to [233], wherein the anti-TROP2 antibody is an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6.

[235] The use according to [234], wherein the anti-TROP2 antibody lacks a lysine residue at the carboxyl terminus of the heavy chain.

[236] The use according to any one of [233] to [235], wherein the average number of units of the drug-linker conjugated per antibody molecule in the antibody-drug conjugate is in the range of from 3.5 to 4.5.

[237] The use according to [224], wherein the antibody in the antibody-drug conjugate is an anti-B7-H3 antibody.

[238] The use according to [237], wherein the anti-B7-H3 antibody is an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8.

[239] The use according to [238], wherein the anti-B7-H3 antibody lacks a lysine residue at the carboxyl terminus of the heavy chain.

[240] The use according to any one of [237] to [239], wherein the average number of units of the drug-linker conjugated per antibody molecule in the antibody-drug conjugate is in the range of from 3.5 to 4.5.

[241] The use according to [224], wherein the antibody in the antibody-drug conjugate is an anti-GPR20 antibody.

[242] The use according to [241], wherein the anti-GPR20 antibody is an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10.

[243] The use according to [242], wherein the anti-GPR20 antibody lacks a lysine residue at the carboxyl terminus of the heavy chain.

[244] The use according to any one of [241] to [243], wherein the average number of units of the drug-linker conjugated per antibody molecule in the antibody-drug conjugate is in the range of from 7 to 8.

[245] The use according to [244], wherein the antibody in the antibody-drug conjugate is an anti-CDH6 antibody.

[246] The use according to [245], wherein the anti-CDH6 antibody is an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12.

[247] The use according to [246], wherein the anti-CDH6 antibody lacks a lysine residue at the carboxyl terminus of the heavy chain.

[248] The use according to any one of [245] to [247], wherein the average number of units of the drug-linker conjugated per antibody molecule in the antibody-drug conjugate is in the range of from 7 to 8.

[249] A therapeutic agent for metastatic cancer comprising, as an active component, an antibody-drug conjugate in which a drug-linker represented by the following formula:

[Formula 9]

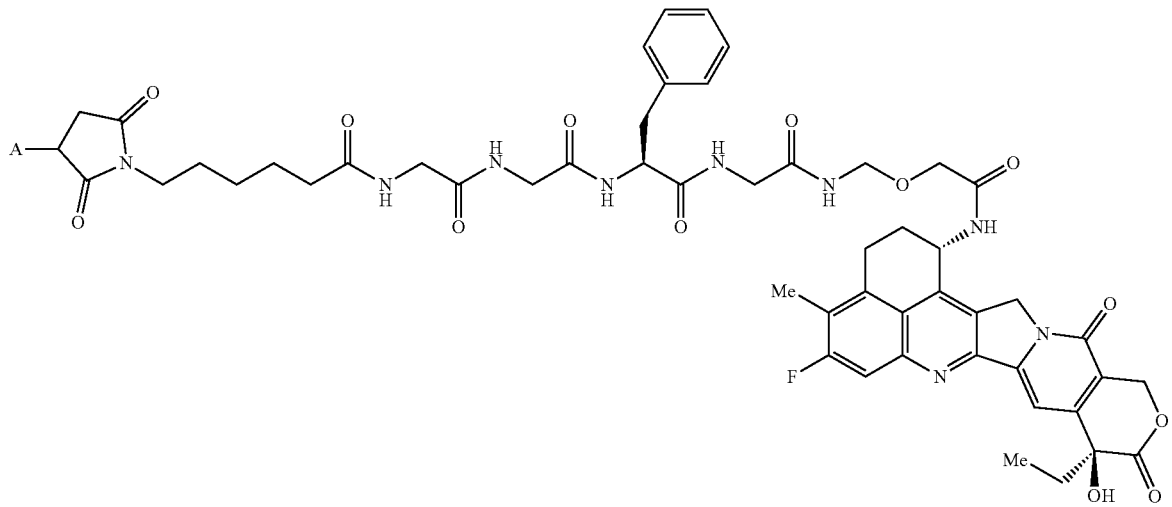

wherein A represents a connecting position to an antibody;

is conjugated to the antibody via a thioether bond.

[250] The therapeutic agent according to [249], wherein the metastatic cancer is at least one selected from the group consisting of a metastatic brain tumor, a metastatic bone tumor, a metastatic lung tumor and metastatic liver cancer.

[251] The therapeutic agent according to [250], wherein the metastatic cancer is a metastatic bone tumor.

[252] A therapeutic agent for metastatic cancer comprising, as an active component, an antibody-drug conjugate represented by the following formula:

[Formula 10]

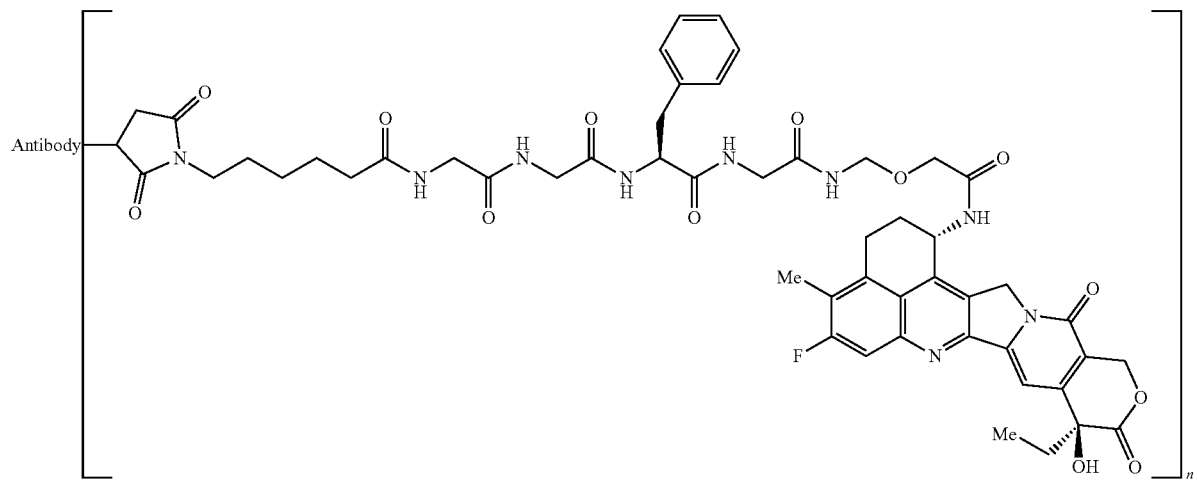

wherein the drug-linker is conjugated to the antibody via a thioether bond, and n is the average number of units of the drug-linker conjugated per antibody molecule.

[253] The therapeutic agent according to [252], wherein the metastatic cancer is at least one selected from the group consisting of a metastatic brain tumor, a metastatic bone tumor, a metastatic lung tumor and metastatic liver cancer.

[254] The therapeutic agent according to [253], wherein the metastatic cancer is a metastatic bone tumor.

[255] A method of treatment for metastatic cancer, comprising administering an antibody-drug conjugate in which a drug-linker represented by the following formula:

[Formula 11]

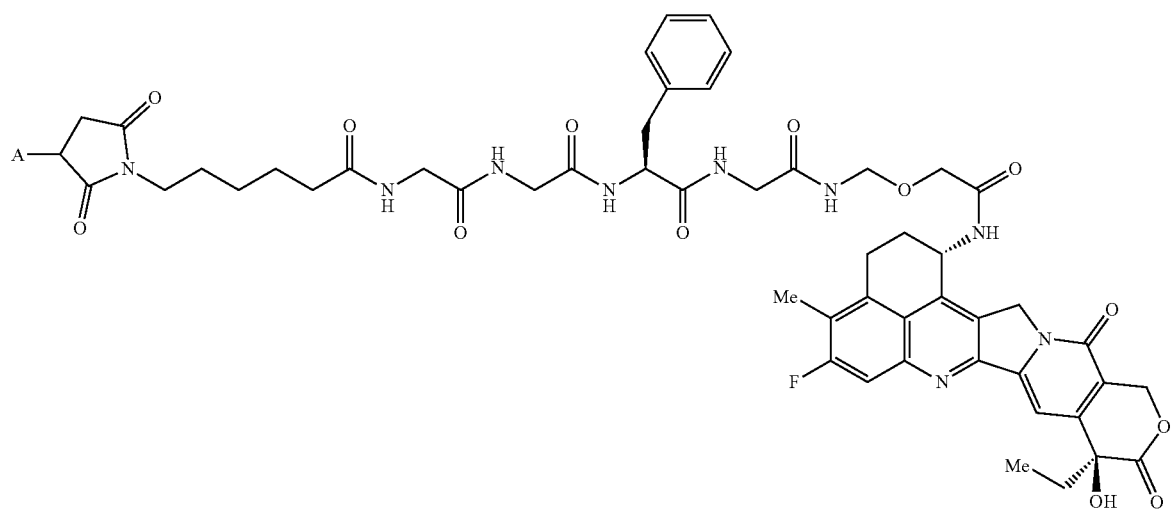

wherein A represents a connecting position to an antibody, is conjugated to the antibody via a thioether bond; to a subject in need of the treatment for metastatic cancer.

[256] The method of treatment according to [255], wherein the metastatic cancer is at least one selected from the group consisting of a metastatic brain tumor, a metastatic bone tumor, a metastatic lung tumor and metastatic liver cancer.

[257] The method of treatment according to [256], wherein the metastatic cancer is a metastatic bone tumor.

[258] A method of treatment for metastatic cancer, comprising administering an antibody-drug conjugate represented by the following formula:

[Formula 12]

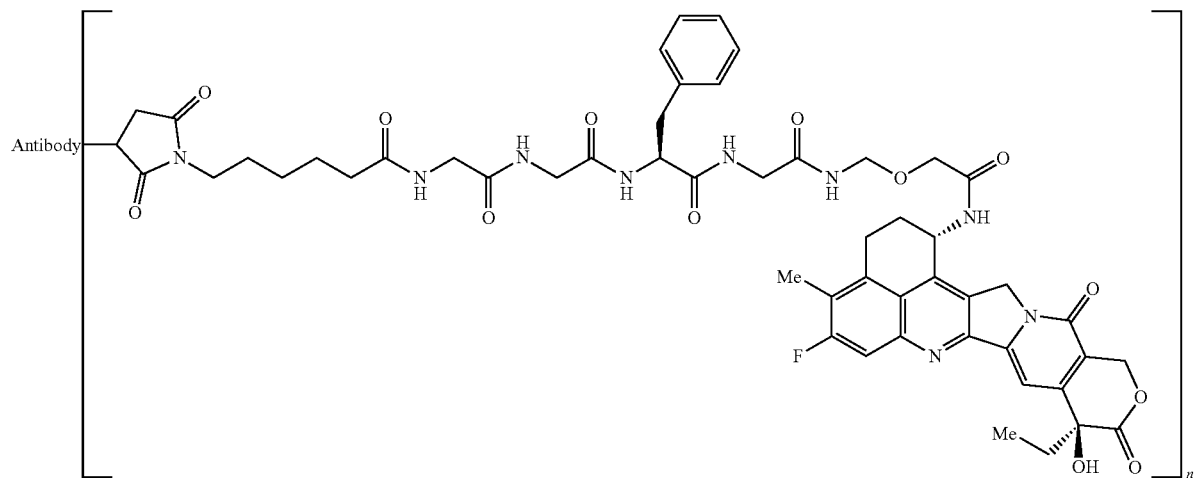

wherein the drug-linker is conjugated to the antibody via a thioether bond, and n is the average number of units of the drug-linker conjugated per antibody molecule; to a subject in need of the treatment for metastatic cancer.

[259] The method of treatment according to [258], wherein the metastatic cancer is at least one selected from the group consisting of a metastatic brain tumor, a metastatic bone tumor, a metastatic lung tumor and metastatic liver cancer.

[260] The method of treatment according to [259], wherein the metastatic cancer is a metastatic bone tumor.

[261] An antibody-drug conjugate for use in treating metastatic cancer, in which a drug-linker represented by the following formula:

[Formula 13]

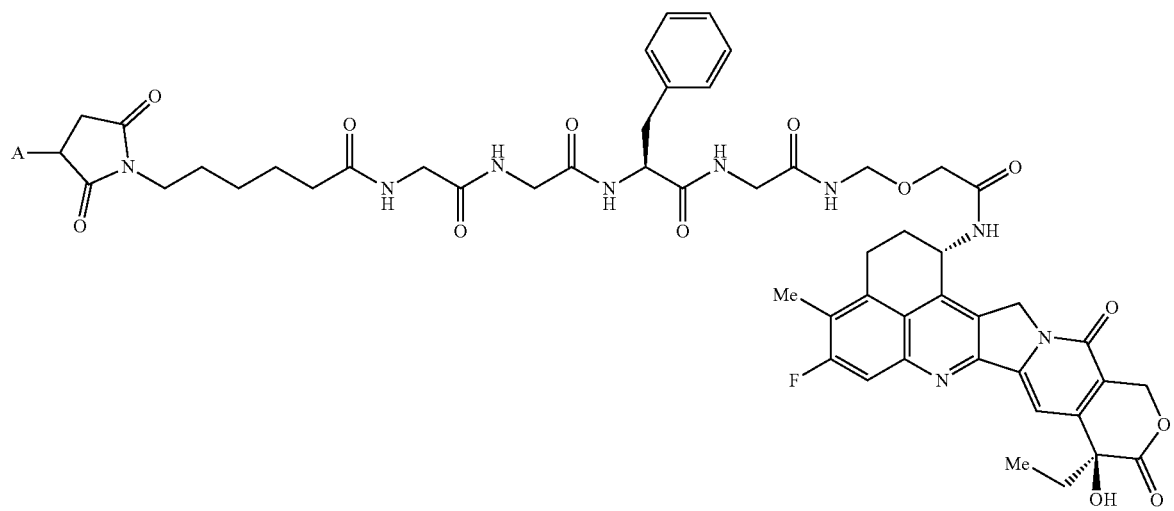

wherein A represents a connecting position to an antibody;
is conjugated to the antibody via a thioether bond.

[262] The antibody-drug conjugate according to [261], wherein the metastatic cancer is at least one selected from the group consisting of a metastatic brain tumor, a metastatic bone tumor, a metastatic lung tumor and metastatic liver cancer.

[263] The antibody-drug conjugate according to [262], wherein the metastatic cancer is a metastatic bone tumor.

[264] An antibody-drug conjugate for use in treating metastatic cancer, represented by the following formula:

[Formula 14]

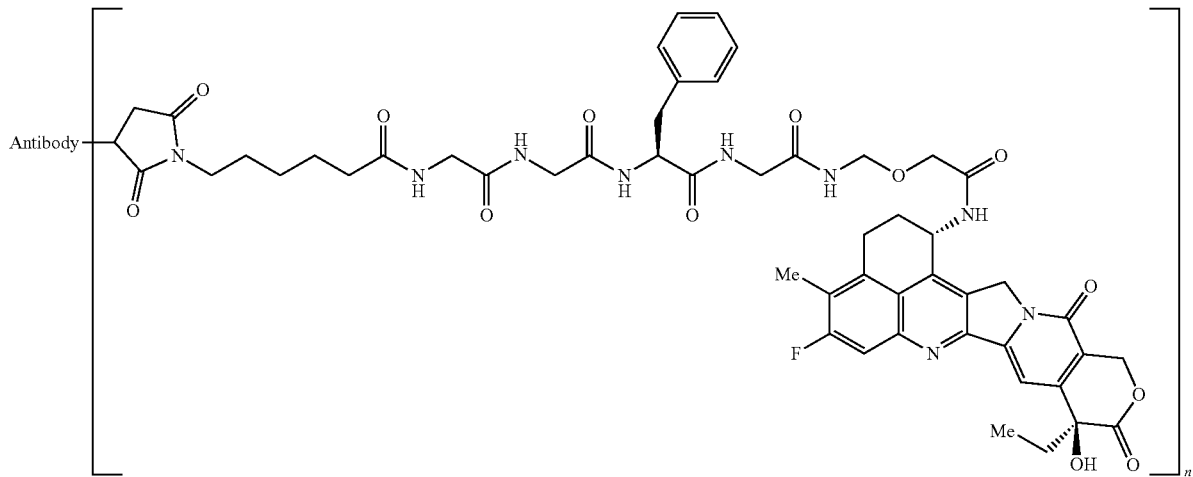

wherein the drug-linker is conjugated to the antibody via a thioether bond, and n is the average number of units of the drug-linker conjugated per antibody molecule.

[265] The antibody-drug conjugate according to [264], wherein the metastatic cancer is at least one selected from the group consisting of a metastatic brain tumor, a metastatic bone tumor, a metastatic lung tumor and metastatic liver cancer.

[266] The antibody-drug conjugate according to [265], wherein the metastatic cancer is a metastatic bone tumor.

[267] Use of an antibody-drug conjugate for the manufacture of a medicament for treating metastatic cancer, in which a drug-linker represented by the following formula:

[Formula 15]

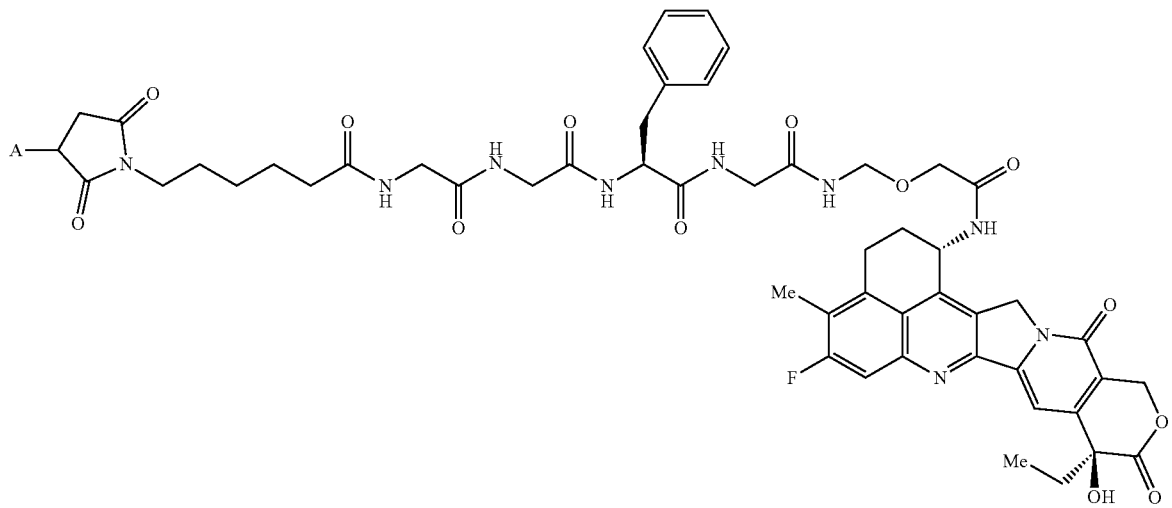

wherein A represents a connecting position to an antibody;

is conjugated to the antibody via a thioether bond.

[268] The use according to [267], wherein the metastatic cancer is at least one selected from the group consisting of a metastatic brain tumor, a metastatic bone tumor, a metastatic lung tumor and metastatic liver cancer.

[269] The use according to [268], wherein the metastatic cancer is a metastatic bone tumor.

[270] Use of an antibody-drug conjugate for the manufacture of a medicament for treating metastatic cancer, represented by the following formula:

[Formula 16]

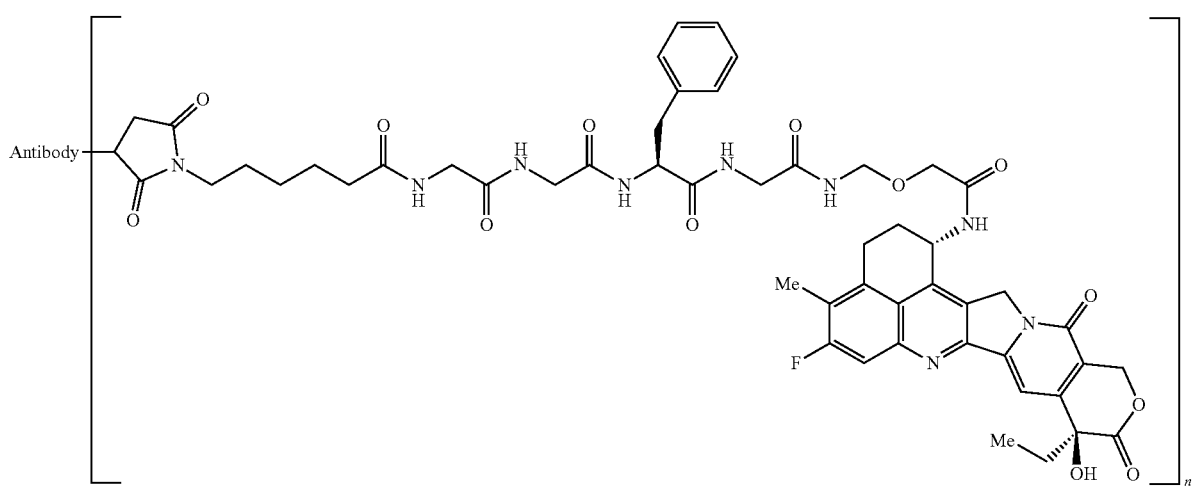

wherein the drug-linker is conjugated to the antibody via a thioether bond, and n is the average number of units of the drug-linker conjugated per antibody molecule.

[271] The use according to [270], wherein the metastatic cancer is at least one selected from the group consisting of a metastatic brain tumor, a metastatic bone tumor, a metastatic lung tumor and metastatic liver cancer.

[272] The use according to [271], wherein the metastatic cancer is a metastatic bone tumor.

Advantageous Effects of Invention

The present invention provides a therapeutic agent for a metastatic brain tumor comprising a specific antibody-drug conjugate, and/or a method of treatment for a metastatic brain tumor comprising administering a specific antibody-drug conjugate to a subject.

BRIEF DESCRIPTION OF DRAWINGS

FIG. 1 is a diagram showing the amino acid sequence of a heavy chain of an anti-HER2 antibody (SEQ ID NO: 1).

FIG. 2 is a diagram showing the amino acid sequence of a light chain of an anti-HER2 antibody (SEQ ID NO: 2).

FIG. 3 is a diagram showing the amino acid sequence of a heavy chain of an anti-HER3 antibody (SEQ ID NO: 3).

FIG. 4 is a diagram showing the amino acid sequence of a light chain of an anti-HER3 antibody (SEQ ID NO: 4).

FIG. 5 is a diagram showing the amino acid sequence of a heavy chain of an anti-TROP2 antibody (SEQ ID NO: 5).

FIG. 6 is a diagram showing the amino acid sequence of a light chain of an anti-TROP2 antibody (SEQ ID NO: 6).

FIG. 7 is a diagram showing the amino acid sequence of a heavy chain of an anti-B7-H3 antibody (SEQ ID NO: 7).

FIG. 8 is a diagram showing the amino acid sequence of a light chain of an anti-B7-H3 antibody (SEQ ID NO: 8).

FIG. 9 is a diagram showing the life-prolonging effects of an antibody-drug conjugate (1) on mice with intracranially transplanted KPL-4-Luc.

FIG. 10 is a diagram showing the antitumor effects of an antibody-drug conjugate (1) on mice with intracranially transplanted KPL-4-Luc. The amount of tumor is confirmed by the luminescence intensity of KPL-4-Luc.

FIG. 11 is diagrams showing brain pathological images by hematoxylin and eosin staining on mice (No. 1 and No. 2) of a solvent-administered group. The center images show overall pathological images, and the left and right images show enlarged pathological images. Tumor masses are found in the area surrounded by a dotted line or the area shown by arrows.

FIG. 12 is a diagram showing the amino acid sequence of a heavy chain of an anti-GPR20 antibody (SEQ ID NO: 9).

FIG. 13 is a diagram showing the amino acid sequence of a light chain of an anti-GPR20 antibody (SEQ ID NO: 10).

FIG. 14 is a diagram showing the amino acid sequence of a heavy chain of an anti-CDH6 antibody (SEQ ID NO: 11).

FIG. 15 is a diagram showing the amino acid sequence of a light chain of an anti-CDH6 antibody (SEQ ID NO: 12).

DESCRIPTION OF EMBODIMENTS

Hereinafter, preferred modes for carrying out the present invention are described. The embodiments described below are given merely for illustrating one example of a typical embodiment of the present invention and are not intended to limit the scope of the present invention.

1. Metastatic Brain Tumor

In the present invention, the term "metastatic brain tumor" means a tumor developed by metastasis of a primary cancer (a cancer developed in biological tissues other than the brain) to the brain. The metastatic brain tumor in the present invention includes not only tumors metastasized into the brain parenchyma, but also tumors invading the pia mater and the arachnoid membrane (meningeal carcinomatosis). The metastasis site may be one or several sites. Further, the metastatic brain tumor is mostly found after symptoms of a primary cancer appear, but may also be found before symptoms of a primary cancer appear.

As the symptoms of the metastatic brain tumor, for example, headache, vomiting, visual impairment, consciousness disorder, convulsive seizure, paralysis and language disorder can be exemplified. These symptoms are inferred to be caused by direct damage of brain tissues by a tumor and an increased intracranial pressure.

Examination of the metastatic brain tumor can be carried out by, for example, CT (Computed Tomography), PET (Positron Emission Tomography), MRI (Magnetic Resonance Imaging), or the like.

For the primary cancer for metastatic brain tumors, lung cancer, breast cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma and sarcoma can be exemplified. Among these, lung cancer, breast cancer and melanoma are particularly found as primary cancers for metastatic brain tumors at high percentages.

2. Antibody-Drug Conjugate

The antibody-drug conjugate used in the present invention is an antibody-drug conjugate in which a drug-linker represented by the following formula:

[Formula 17]

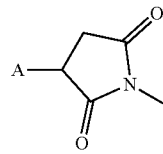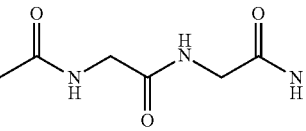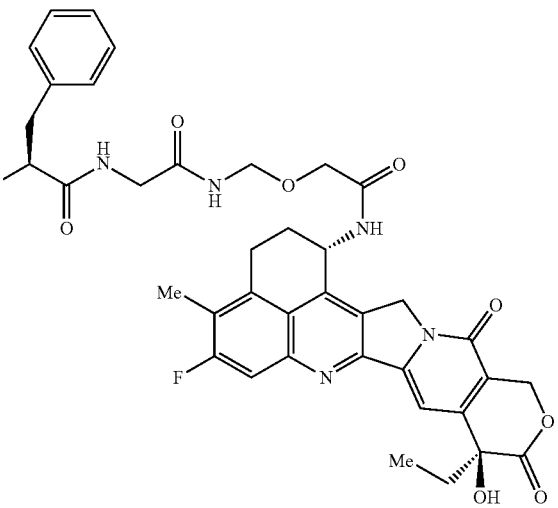

wherein A represents a connecting position to an antibody;
is conjugated to the antibody via a thioether bond.

In the present invention, the partial structure consisting of a linker and a drug in the antibody-drug conjugate is referred to as a "drug-linker". The drug-linker is connected to a thiol group (in other words, the sulfur atom of a cysteine residue) formed at an interchain disulfide bond site (two sites between heavy chains, and two sites between a heavy chain and a light chain) in the antibody.

The drug-linker of the present invention includes exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolizino[1,2-b]quinolin-10,13-dione, (also expressed as chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione)), which is a topoisomerase I inhibitor, as a component. Exatecan is a camptothecin derivative having an antitumor effect, represented by the following formula:

[Formula 18]

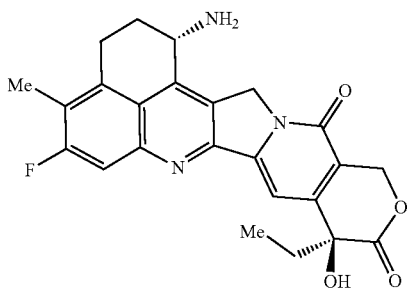

The antibody-drug conjugate used in the present invention can also be represented by the following formula:

[Formula 19]

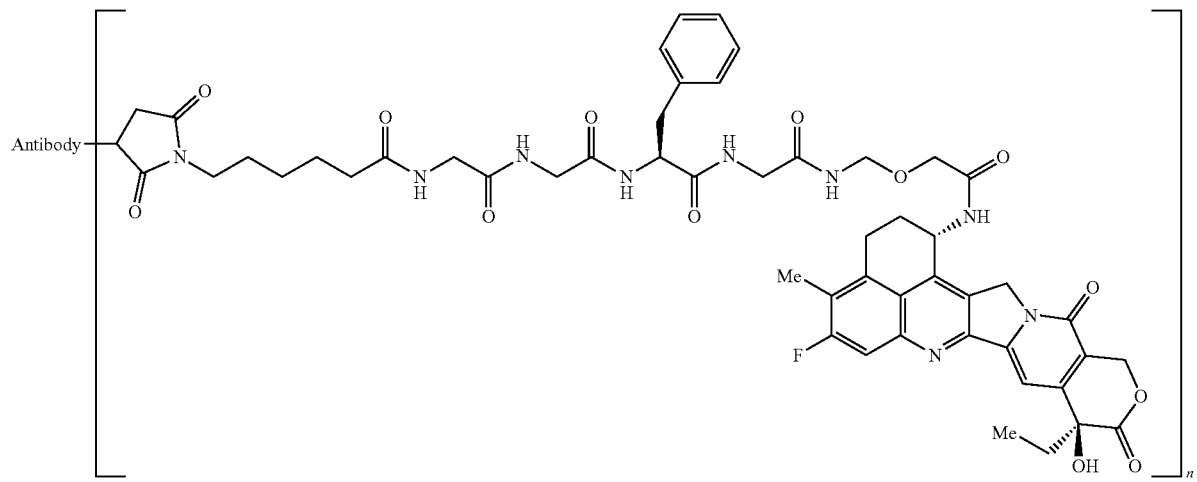

wherein, the drug-linker is conjugated to an antibody via a thioether bond. The meaning of n is the same as that of what is called the average number of conjugated drug molecules (DAR; Drug-to-Antibody Ratio), and indicates the average number of units of the drug-linker conjugated per antibody molecule.

After migrating into cancer cells, the antibody-drug conjugate used in the present invention releases the compound represented by the following formula:

[Formula 20]

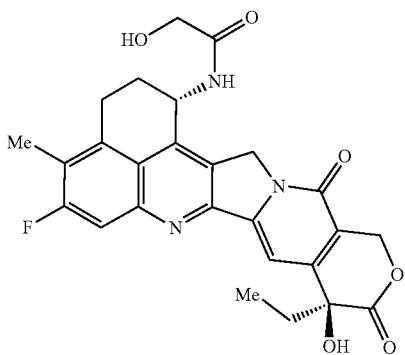

and thereby exerts an antitumor effect.

The aforementioned compound is inferred to be the original source of the antitumor activity of the antibody-drug conjugate used in the present invention, and has been confirmed to have a topoisomerase I inhibitory effect (Ogitani Y. et al., Clinical Cancer Research, 2016 Oct. 15; 22(20):5097-5108, Epub 2016 Mar. 29).

The antibody-drug conjugate used in the present invention is also known to have a bystander effect (Ogitani Y. et al., Cancer Science (2016) 107, 1039-1046).

The bystander effect is exerted through a process such that the antibody-drug conjugate used in the present invention is internalized in cancer cells expressing the target and the aforementioned compound is released and then exerts an antitumor effect also on cancer cells which are present therearound and not expressing the target.

3. Antibody in Antibody-Drug Conjugate

The antibody in the antibody-drug conjugate used in the present invention may be derived from any species, and is preferably an antibody derived from a human, a rat, a mouse, or a rabbit. In cases when the antibody is derived from species other than human species, it is preferably chimerized or humanized using a well-known technique. The antibody of the present invention may be a polyclonal antibody or a monoclonal antibody and is preferably a monoclonal antibody.

The antibody in the antibody-drug conjugate used in the present invention is an antibody preferably having the characteristic of being able to target cancer cells, and is preferably an antibody possessing the property of being able to recognize a cancer cell, the property of being able to bind to a cancer cell, the property of being incorporated and internalized in a cancer cell, and/or cytocidal activity against cancer cells.

The binding activity of the antibody against cancer cells can be confirmed using flow cytometry. The internalization of the antibody into cancer cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000). As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added at varying concentrations into the culture system to be able to determine inhibitory activity against focus formation, colony formation, and spheroid growth. The antitumor activity can be confirmed in vivo, for example, by administering the antibody to a nude mouse with a transplanted cancer cell line highly expressing the target protein, and determining changes in the cancer cells.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against cancer cells, it is important and also preferred that the antibody should have the property of being internalized to migrate into cancer cells.

The antibody in the antibody-drug conjugate used in the present invention can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen can be fused with myeloma cells according to a method known in the art (e.g., Kohler and Milstein, Nature (1975) 256, p. 495-497; Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The antibody in the antibody-drug conjugate used in the present invention is preferably a recombinant antibody obtained by artificial modification for the purpose of decreasing heterologous antigenicity to humans such as a chimeric antibody or a humanized antibody, or is preferably an antibody having only the gene sequence of an antibody derived from a human, that is, a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (Proc. Natl. Acad. Sci. USA, 81, 6851-6855, (1984)).

As the humanized antibody, an antibody obtained by integrating only the complementarity determining region (CDR) of a heterologous antibody into a human-derived antibody (Nature (1986) 321, pp. 522-525), an antibody obtained by grafting a part of the amino acid residues of the framework of a heterologous antibody as well as the CDR sequence of the heterologous antibody to a human antibody by a CDR-grafting method (WO 90/07861), and an antibody humanized using a gene conversion mutagenesis strategy (U.S. Pat. No. 5,821,337) can be exemplified.

As the human antibody, an antibody generated by using a human antibody-producing mouse having a human chromosome fragment including genes of a heavy chain and a light chain of a human antibody (see Tomizuka, K. et al., Nature Genetics (1997) 16, p. 133-143; Kuroiwa, Y. et. al., Nucl. Acids Res. (1998) 26, p. 3447-3448; Yoshida, H. et. al., Animal Cell Technology: Basic and Applied Aspects vol. 10, p. 69-73 (Kitagawa, Y., Matsuda, T. and Iijima, S. eds.), Kluwer Academic Publishers, 1999; Tomizuka, K. et. al., Proc. Natl. Acad. Sci. USA (2000) 97, p. 722-727, etc.) can be exemplified. As an alternative, an antibody obtained by phage display, the antibody being selected from a human antibody library (see Wormstone, I. M. et. al, Investigative Ophthalmology & Visual Science. (2002)43 (7), p. 2301-2308; Carmen, S. et. al., Briefings in Functional Genomics and Proteomics (2002), 1(2), p. 189-203; Siriwardena, D. et. al., Ophthalmology (2002) 109(3), p. 427-431, etc.) can be exemplified.

In the antibody in the antibody-drug conjugate used in present invention, modified variants of the antibody are also included. The modified variant refers to a variant obtained by subjecting the antibody according to the present invention to chemical or biological modification. Examples of the chemically modified variant include variants including a linkage of a chemical moiety to an amino acid skeleton, variants including a linkage of a chemical moiety to an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen according to the present invention, for example, an enzyme-labeled antibody, a fluorescence-labeled antibody, and an affinity-labeled antibody are also included in the meaning of the modified variant. Such a modified variant of the antibody according to the present invention is useful for improving the stability and blood retention of the antibody, reducing the antigenicity thereof, detecting or isolating an antibody or an antigen, and so on.

Further, by regulating the modification of a glycan which is linked to the antibody according to the present invention (glycosylation, defucosylation, etc.), it is possible to enhance antibody-dependent cellular cytotoxic activity. As the technique for regulating the modification of a glycan of antibodies, WO 99/54342, WO 00/61739, WO 02/31140, WO 2007/133855, WO 2013/120066, etc. are known. However, the technique is not limited thereto. In the antibody according to the present invention, antibodies in which the modification of a glycan is regulated are also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (complement activation, antibody-dependent cellular cytotoxicity, etc.) of the antibody. Therefore, in the antibody according to the present invention, antibodies subjected to such modification and functional fragments of the antibody are also included, and deletion variants in which one or two amino acids have been deleted at the carboxyl terminus of the heavy chain, variants obtained by amidation of the deletion variants (for example, a heavy chain in which the carboxyl terminal proline residue has been amidated), and the like are also included. The type of deletion variant having a deletion at the carboxyl terminus of the heavy chain of the antibody according to the present invention is not limited to the above variants as long as the antigen-binding affinity and the effector function are conserved. The two heavy chains constituting the antibody according to the present invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the present invention and the culture conditions; however, an antibody in which one amino acid residue at the carboxyl terminus has been deleted in both of the two heavy chains in the antibody according to the present invention can be preferably exemplified.

As isotypes of the antibody according to the present invention, for example, IgG (IgG1, IgG2, IgG3, IgG4) can be exemplified, and IgG1 or IgG2 can be exemplified preferably.

Examples of antibodies in the antibody-drug conjugate used in the present invention can include, but are not particularly limited to, an anti-HER2 antibody, an anti-HER3 antibody, an anti-TROP2 antibody, an anti-B7-H3 antibody, an anti-CD3 antibody, an anti-CD30 antibody, an anti-CD33 antibody, an anti-CD37 antibody, an anti-CD56 antibody, an anti-CD98 antibody, an anti-DR5 antibody, an anti-EGFR antibody, an anti-EPHA2 antibody, an anti-FGFR2 antibody, an anti-FGFR4 antibody, an anti-FOLR1 antibody, an anti-VEGF antibody, an anti-CD20 antibody, an anti-CD22 antibody, an anti-CD70 antibody, an anti-PSMA antibody, an anti-CEA antibody, an anti-Mesothelin antibody, an anti-A33 antibody, an anti-CanAg antibody, an anti-Cripto antibody, an anti-G250 antibody, an anti-MUC1 antibody, an anti-GPNMB antibody, an anti-Integrin antibody, an anti-Tenascin-C antibody, an anti-SLC44A4 antibody, an anti-GPR20 antibody, and an anti-CDH6 antibody. Further, an anti-HER2 antibody, an anti-HER3 antibody, an anti-TROP2 antibody, an anti-B7-H3 antibody, an anti-GPR20 antibody, and an anti-CDH6 antibody can be preferably exemplified, and an anti-HER2 antibody can be more preferably exemplified.

In the present invention, the term "anti-HER2 antibody" refers to an antibody which binds specifically to HER2 (Human Epidermal Growth Factor Receptor Type 2; ErbB-2), and preferably has an activity of internalization in HER2-expressing cells by binding to HER2.

Examples of the anti-HER2 antibody include trastuzumab (U.S. Pat. No. 5,821,337) and pertuzumab (International Publication No. WO 01/00245). Preferably, trastuzumab can be exemplified.

In the present invention, the term "anti-HER3 antibody" refers to an antibody which binds specifically to HER3 (Human Epidermal Growth Factor Receptor Type 3; ErbB-3), and preferably has an activity of internalization in HER3-expressing cells by binding to HER3.

Examples of the anti-HER3 antibody include patritumab (U3-1287), U1-59 (International Publication No. WO 2007/077028), MM-121 (seribantumab), an anti-ERBB3 antibody described in International Publication No. WO 2008/100624, RG-7116 (lumretuzumab), and LJM-716 (elgemtumab). Preferably, patritumab and U1-59 can be exemplified.

In the present invention, the term "anti-TROP2 antibody" refers to an antibody which binds specifically to TROP2 (TACSTD2: Tumor-associated calcium signal transducer 2; EGP-1), and preferably has an activity of internalization in TROP2-expressing cells by binding to TROP2.

Examples of the anti-TROP2 antibody include hTINA1-H1L1 (International Publication No. WO 2015/098099).

In the present invention, the term "anti-B7-H3 antibody" refers to an antibody which binds specifically to B7-H3 (B cell antigen #7 homolog 3; PD-L3; CD276), and preferably has an activity of internalization in B7-H3-expressing cells by binding to B7-H3.

Examples of the anti-B7-H3 antibody include M30-H1-L4 (International Publication No. WO 2014/057687).

In the present invention, the term "anti-GPR20 antibody" refers to an antibody which binds specifically to GPR20 (G Protein-coupled receptor 20), and preferably has an activity of internalization in GPR20-expressing cells by binding to GPR20.

Examples of the anti-GPR20 antibody include h046-H4e/L7 (International Publication No. WO 2018/135501).

In the present invention, the term "anti-CDH6 antibody" refers to an antibody which binds specifically to CDH6 (Cadherin-6), and preferably has an activity of internalization in CDH6-expressing cells by binding to CDH6.

Examples of the anti-CDH6 antibody include H01L02 (International Publication No. WO 2018/212136).

4. Production of Antibody-Drug Conjugate

A drug-linker intermediate for use in the production of the antibody-drug conjugate used in the present invention is represented by the following formula.

[Formula 21]

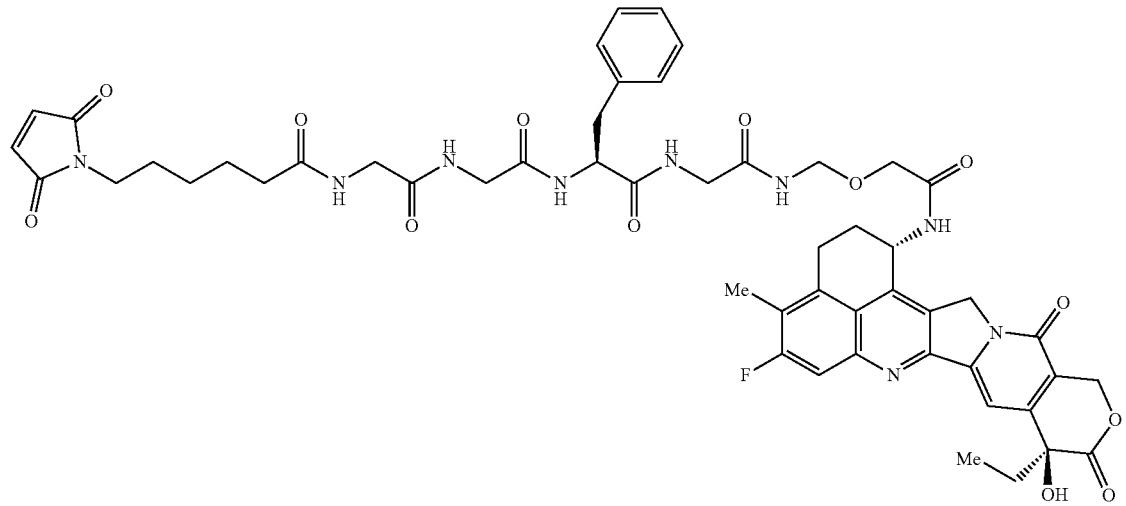

The drug-linker intermediate can be expressed as the chemical name N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide, and can be produced with reference to descriptions in International Publication No. WO 2014/057687, International Publication No. WO 2015/098099, International Publication No. WO 2015/115091, International Publication No. WO 2015/155998, International Publication No. WO 2019/044947, and so on.

The antibody-drug conjugate used in the present invention can be produced by reacting the above-described drug-linker intermediate and an antibody having a thiol group (alternatively referred to as a sulfhydryl group).

The antibody having a sulfhydryl group can be obtained by a method well known in the art (Hermanson, G. T, Bioconjugate Techniques, pp. 56-136, pp. 456-493, Academic Press (1996)). For example, by using 0.3 to 3 molar equivalents of a reducing agent such as tris(2-carboxyethyl) phosphine hydrochloride (TCEP) per interchain disulfide within the antibody and reacting with the antibody in a buffer solution containing a chelating agent such as ethylenediamine tetraacetic acid (EDTA), an antibody having a sulfhydryl group with partially or completely reduced interchain disulfides within the antibody can be obtained.

Further, by using 2 to 20 molar equivalents of the drug-linker intermediate per the antibody having a sulfhydryl group, an antibody-drug conjugate in which 2 to 8 drug molecules are conjugated per antibody molecule can be produced.

The average number of conjugated drug molecules per antibody molecule of the antibody-drug conjugate produced can be determined, for example, by a method of calculation based on measurement of UV absorbance for the anti-HER2 antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the antibody and the drug-linker intermediate and calculation of the average number of conjugated drug molecules per antibody molecule of the antibody-drug conjugate can be performed with reference to descriptions in International Publication No. WO 2014/057687, International Publication No. WO 2015/098099, International Publication No. WO 2015/115091, International Publication No. WO 2015/155998, International Publication No. WO 2018/135501, International Publication No. WO 2018/212136, and so on.

In the present invention, the term "anti-HER2 antibody-drug conjugate" refers to an antibody-drug conjugate such that the antibody in the antibody-drug conjugate according to the present invention is an anti-HER2 antibody.

The anti-HER2 antibody is preferably an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, or an antibody comprising a heavy chain consisting of an amino acid sequence represented by SEQ ID NO: 1 and a light chain consisting of an amino acid sequence represented by SEQ ID NO: 2.

The average number of units of the drug-linker conjugated per antibody molecule in the anti-HER2 antibody-drug conjugate is preferably 2 to 8, more preferably 3 to 8, even more preferably 7 to 8, even more preferably 7.5 to 8, and even more preferably about 8.

The anti-HER2 antibody-drug conjugate can be produced with reference to descriptions in International Publication No. WO 2015/115091 and so on.

In the present invention, the term "anti-HER3 antibody-drug conjugate" refers to an antibody-drug conjugate such that the antibody in the antibody-drug conjugate according to the present invention is an anti-HER3 antibody.

The anti-HER3 antibody is preferably an antibody comprising a heavy chain comprising CDRH1 consisting of an amino acid sequence consisting of amino acid residues 26 to 35 of SEQ ID NO: 3, CDRH2 consisting of an amino acid sequence consisting of amino acid residues 50 to 65 of SEQ ID NO: 3, and CDRH3 consisting of an amino acid sequence consisting of amino acid residues 98 to 106 of SEQ ID NO: 3 and a light chain comprising CDRL1 consisting of an amino acid sequence consisting of amino acid residues 24 to 39 of SEQ ID NO: 4, CDRL2 consisting of an amino acid sequence consisting of amino acid residues 56 to 62 of SEQ ID NO: 4, and CDRL3 consisting of an amino acid sequence consisting of amino acid residues 95 to 103 of SEQ ID NO: 4, more preferably an antibody comprising a heavy chain comprising a heavy chain variable region consisting of an amino acid sequence consisting of amino acid residues 1 to 117 of SEQ ID NO: 3 and a light chain comprising a light chain variable region consisting of an amino acid sequence consisting of amino acid residues 1 to 113 of SEQ ID NO: 4, and even more preferably an antibody comprising a heavy chain consisting of an amino acid sequence represented by SEQ ID NO: 3 and a light chain consisting of an amino acid sequence represented by SEQ ID NO: 4, or a variant of the antibody in which a lysine residue at the carboxyl terminus of the heavy chain is deleted.

The average number of units of the drug-linker conjugated per antibody molecule in the anti-HER3 antibody-drug conjugate is preferably 2 to 8, more preferably 3 to 8, even more preferably 7 to 8, even more preferably 7.5 to 8, and even more preferably about 8.

The anti-HER3 antibody-drug conjugate can be produced with reference to descriptions in International Publication No. WO 2015/155998 and so on.

In the present invention, the term "anti-TROP2 antibody-drug conjugate" refers to an antibody-drug conjugate such that the antibody in the antibody-drug conjugate according to the present invention is an anti-TROP2 antibody.

The anti-TROP2 antibody is preferably an antibody comprising a heavy chain comprising CDRH1 consisting of an amino acid sequence consisting of amino acid residues 50 to 54 of SEQ ID NO: 5, CDRH2 consisting of an amino acid sequence consisting of amino acid residues 69 to 85 of SEQ ID NO: 5, and CDRH3 consisting of an amino acid sequence consisting of amino acid residues 118 to 129 of SEQ ID NO: 5 and a light chain comprising CDRL1 consisting of an amino acid sequence consisting of amino acid residues 44 to 54 of SEQ ID NO: 6, CDRL2 consisting of an amino acid sequence consisting of amino acid residues 70 to 76 of SEQ ID NO: 6, and CDRL3 consisting of an amino acid sequence consisting of amino acid residues 109 to 117 of SEQ ID NO: 6, more preferably an antibody comprising a heavy chain comprising a heavy chain variable region consisting of an amino acid sequence consisting of amino acid residues 20 to 140 of SEQ ID NO: 5 and a light chain comprising a light chain variable region consisting of an amino acid sequence consisting of amino acid residues 21 to 129 of SEQ ID NO: 6, and even more preferably an antibody comprising a heavy chain consisting of an amino acid sequence consisting of amino acid residues 20 to 470 of SEQ ID NO: 5 and a light chain consisting of an amino acid sequence consisting of amino acid residues 21 to 234 of SEQ ID NO: 6, or a variant of the antibody in which a lysine residue at the carboxyl terminus of the heavy chain is deleted.

The average number of units of the drug-linker conjugated per antibody molecule in the anti-TROP2 antibody-drug conjugate is preferably 2 to 8, more preferably 3 to 5, even more preferably 3.5 to 4.5, and even more preferably about 4.

The anti-TROP2 antibody-drug conjugate can be produced with reference to descriptions in International Publication No. WO 2015/098099 and so on.

In the present invention, the term "anti-B7-H3 antibody-drug conjugate" refers to an antibody-drug conjugate such that the antibody in the antibody-drug conjugate according to the present invention is an anti-B7-H3 antibody.

The anti-B7-H3 antibody is preferably an antibody comprising a heavy chain comprising CDRH1 consisting of an amino acid sequence consisting of amino acid residues 50 to 54 of SEQ ID NO: 7, CDRH2 consisting of an amino acid sequence consisting of amino acid residues 69 to 85 of SEQ ID NO: 7, and CDRH3 consisting of an amino acid sequence consisting of amino acid residues 118 to 130 of SEQ ID NO: 7 and a light chain comprising CDRL1 consisting of an amino acid sequence consisting of amino acid residues 44 to 53 of SEQ ID NO: 8, CDRL2 consisting of an amino acid sequence consisting of amino acid residues 69 to 75 of SEQ ID NO: 8, and CDRL3 consisting of an amino acid sequence consisting of amino acid residues 108 to 116 of SEQ ID NO: 8, more preferably an antibody comprising a heavy chain comprising a heavy chain variable region consisting of an amino acid sequence consisting of amino acid residues 20 to 141 of SEQ ID NO: 7 and a light chain comprising a light chain variable region consisting of an amino acid sequence consisting of amino acid residues 21 to 128 of SEQ ID NO: 8, and even more preferably an antibody comprising a heavy chain consisting of an amino acid sequence consisting of amino acid residues 20 to 471 of SEQ ID NO: 7 and a light chain consisting of an amino acid sequence consisting of amino acid residues 21 to 233 of SEQ ID NO: 8, or a variant of the antibody in which a lysine residue at the carboxyl terminus of the heavy chain is deleted.

The average number of units of the drug-linker conjugated per antibody molecule in the anti-B7-H3 antibody-drug conjugate is preferably 2 to 8, more preferably 3 to 5, even more preferably 3.5 to 4.5, and even more preferably about 4.

The anti-B7-H3 antibody-drug conjugate used in the present invention can be produced with reference to descriptions in International Publication No. WO 2014/057687 and so on.

In the present invention, the term "anti-GPR20 antibody-drug conjugate" refers to an antibody-drug conjugate wherein the antibody in the antibody-drug conjugate according to the present invention is an anti-GPR20 antibody.

The anti-GPR20 antibody is preferably an antibody comprising a heavy chain comprising CDRH1 consisting of an amino acid sequence consisting of amino acid residues 45 to 54 of SEQ ID NO: 9, CDRH2 consisting of an amino acid sequence consisting of amino acid residues 69 to 78 of SEQ ID NO: 9, and CDRH3 consisting of an amino acid sequence consisting of amino acid residues 118 to 131 of SEQ ID NO: 9 and a light chain comprising CDRL1 consisting of an amino acid sequence consisting of amino acid residues 44 to 54 of SEQ ID NO: 10, CDRL2 consisting of an amino acid sequence consisting of amino acid residues 70 to 76 of SEQ ID NO: 10, and CDRL3 consisting of an amino acid sequence consisting of amino acid residues 109 to 117 of SEQ ID NO: 10, more preferably an antibody comprising a heavy chain comprising a heavy chain variable region consisting of an amino acid sequence consisting of amino acid residues 20 to 142 of SEQ ID NO: 9 and a light chain comprising a light chain variable region consisting of an amino acid sequence consisting of amino acid residues 21 to 129 of SEQ ID NO: 10, and even more preferably an antibody comprising a heavy chain consisting of an amino acid sequence consisting of amino acid residues 20 to 472 of SEQ ID NO: 9 and a light chain consisting of an amino acid sequence consisting of amino acid residues 21 to 234 of SEQ ID NO: 10, or a variant of the antibody in which a lysine residue at the carboxyl terminus of the heavy chain is deleted.

The average number of units of the drug-linker conjugated per antibody molecule in the anti-GPR20 antibody-drug conjugate is preferably 2 to 8, more preferably 3 to 8, even more preferably 7 to 8, even more preferably 7.5 to 8, and even more preferably about 8.

The anti-GPR20 antibody-drug conjugate can be produced with reference to descriptions in International Publication No. WO 2018/135501 and so on.

In the present invention, the term "anti-CDH6 antibody-drug conjugate" refers to an antibody-drug conjugate wherein the antibody in the antibody-drug conjugate according to the present invention is an anti-CDH6 antibody.

The anti-CDH6 antibody is preferably an antibody comprising a heavy chain comprising CDRH1 consisting of an amino acid sequence consisting of amino acid residues 45 to 54 of SEQ ID NO: 11, CDRH2 consisting of an amino acid sequence consisting of amino acid residues 69 to 78 of SEQ ID NO: 11, and CDRH3 consisting of an amino acid sequence consisting of amino acid residues 118 to 130 of SEQ ID NO: 11, and a light chain comprising CDRL1 consisting of an amino acid sequence consisting of amino acid residues 44 to 54 of SEQ ID NO: 12, CDRL2 consisting of an amino acid sequence consisting of amino acid residues 70 to 76 of SEQ ID NO: 12, and CDRL3 consisting of an amino acid sequence consisting of amino acid residues 109 to 116 of SEQ ID NO: 12, more preferably an antibody comprising a heavy chain comprising a heavy chain variable region consisting of an amino acid sequence consisting of amino acid residues 20 to 141 of SEQ ID NO: 11 and a light chain comprising a light chain variable region consisting of an amino acid sequence consisting of amino acid residues 21 to 128 of SEQ ID NO: 12, and even more preferably an antibody comprising a heavy chain consisting of an amino acid sequence consisting of amino acid residues 20 to 471 of SEQ ID NO: 11 and a light chain consisting of an amino acid sequence consisting of amino acid residues 21 to 233 of SEQ ID NO: 12, or a variant of the antibody in which the lysine residue at the carboxyl terminus of the heavy chain is deleted.

The average number of units of the drug-linker conjugated per antibody molecule in the anti-CDH6 antibody-drug conjugate is preferably 2 to 8, more preferably 3 to 8, even more preferably 7 to 8, even more preferably 7.5 to 8, and even more preferably about 8.

The anti-CDH6 antibody-drug conjugate can be produced with reference to descriptions in International Publication No. WO 2018/212136 and so on.

5. Therapeutic Agent and/or Method of Treatment

The therapeutic agent of the present invention comprises the antibody-drug conjugate used in the present invention. Further, the method of treatment of the present invention comprises administering the antibody-drug conjugate used in the present invention. The therapeutic agent and the method of treatment can be used for treatment of a metastatic brain tumor.

Primary cancers for the metastatic brain tumor for which the therapeutic agent and/or method of treatment of the present invention can be used are not particularly limited as long as they have a potential to metastasize to the brain, and breast cancer, lung cancer (including small cell lung cancer and non-small cell lung cancer), melanoma, renal cell cancer, kidney cancer, colorectal cancer (also called colon and rectal cancer, and including colon cancer and rectal cancer), gastric cancer (also called gastric adenocarcinoma), head and neck cancer, hepatocellular cancer, liver cancer, ovarian cancer, prostate cancer, bladder cancer, pancreatic cancer, endometrial cancer, thyroid cancer, malignant lymphoma and sarcoma can be exemplified, and breast cancer, lung cancer and melanoma can be preferably exemplified, breast cancer and lung cancer can be more preferably exemplified, and breast cancer can be even more preferably exemplified.

Among the antibody-drug conjugates used in the present invention, a preferable antibody-drug conjugate, particularly having a specific antibody, can be determined by examining the characteristics of the primary cancer and tumor markers. For example, in the case that the primary cancer is breast cancer or lung cancer and the expression of HER2 is found, an anti-HER2 antibody-drug conjugate can be preferably used; in the case that the expression of HER3 is found, an anti-HER3 antibody-drug conjugate can be preferably used; in the case that the expression of TROP2 is found, an anti-TROP2 antibody-drug conjugate can be preferably used; and in the case that the expression of B7-H3 is found, an anti-B7-H3 antibody-drug conjugate can be preferably used. Further, in the case that the primary cancer is melanoma and the expression of HER3 is found, an anti-HER3 antibody-drug conjugate can be preferably used; in the case that the expression of TROP2 is found, an anti-TROP2 antibody-drug conjugate can be preferably used; and in the case that the expression of B7-H3 is found, an anti-B7-H3 antibody-drug conjugate can be preferably used. Further, in the case that the primary cancer is kidney cancer and the expression of CDH6 is found, an anti-CDH6 antibody-drug conjugate can be preferably used.

The presence or absence of HER2, HER3, TROP2, B7-H3, GPR20 and CDH6, and other tumor markers, can be checked by, for example, collecting tumor tissues from a cancer patient and subjecting the formalin fixed paraffin embedded specimen (FFPE) to an examination at a gene product (protein) level, such as an immunohistochemistry (IHC) method, a flow cytometry, a western blot method, or an examination at a gene transcription level, such as an in situ hybridization method (ISH), a quantitative PCR method (q-PCR), or a microarray analysis; alternatively, it can also be checked by collecting cell-free blood circulating tumor DNA (ctDNA) from a cancer patient and subjecting to an examination which uses a method such as next-generation sequencing (NGS).

The therapeutic agent and method of treatment of the present invention can be preferably used for mammals, and can be more preferably used for humans.

The antitumor effect of the therapeutic agent and method of treatment of the present invention can be confirmed by, for example, generating a model in which cancer cells derived from a primary cancer into which a marker gene (for example, luciferase gene) has been transfected are transplanted into the brain of a test animal, and measuring, using any imaging technique, the life-prolonging effects and the transition of luminescence intensity of the marker when the therapeutic agent or method of treatment of the present invention is applied. For example, in the case of transplanting cells into which a luciferase gene has been transfected, luciferin is administered to investigate the luminescence intensity, and in the case that the luminescence intensity is diminished as compared with a control group when the therapeutic agent or method of treatment of the present invention is applied, an antitumor effect is recognized.

Alternatively, the antitumor effect of the therapeutic agent and method of treatment of the present invention can also be confirmed by generating a model in which a test animal is transplanted with a biopsy derived from a patient with a metastatic brain tumor (for example, a PDX brain transplant model) and applying the therapeutic agent or method of treatment of the present invention, and further can also be confirmed by administering the therapeutic agent or applying the method of treatment of the present invention to a patient with a metastatic brain tumor. The measurement of the antitumor effect can be carried out, for example, using CT, PET, and/or MRI, by confirming change in tumor volumes before and after applying the therapeutic agent or method of treatment of the present invention.

In addition, the antitumor effect of the therapeutic agent and method of treatment of the present invention can be confirmed, in a clinical study, with the Response Evaluation Criteria in Solid Tumors (RECIST) evaluation method, WHO's evaluation method, Macdonald's evaluation method, measurement of body weight, and other methods; and can be determined by indicators such as Complete response (CR), Partial response (PR), Progressive disease (PD), Objective response rate (ORR), Duration of response (DoR), Progression-free survival (PFS), and Overall survival (OS).

The foregoing methods can provide confirmation of superiority in terms of the antitumor effect of the therapeutic agent and method of treatment of the present invention against metastatic brain tumors compared to existing anticancer agents.

The therapeutic agent and method of treatment of the present invention can show not only an antitumor effect against metastatic brain tumors, but also an antitumor effect against metastatic cancers other than metastatic brain tumors. Examples of the metastatic cancers other than metastatic brain tumors can include metastatic bone tumors, metastatic lung tumors and metastatic liver cancer, and metastatic bone tumors can be preferably exemplified. Metastatic cancers other than metastatic brain tumors may occur intercurrently with a metastatic brain tumor or may occur separately from a metastatic brain tumor, and the therapeutic agent and method of treatment of the present invention can exert an antitumor effect in both cases.

The therapeutic agent and method of treatment of the present invention can retard growth of cancer cells, suppress their proliferation, and further can kill cancer cells. These effects can allow cancer patients to be free from symptoms caused by cancer or can achieve an improvement in the QOL of cancer patients and attain a therapeutic effect by sustaining the lives of the cancer patients. Even if the therapeutic agent and method of treatment do not accomplish the killing of cancer cells, they can achieve higher QOL of cancer patients while achieving longer-term survival, by inhibiting or controlling the growth of cancer cells.

The therapeutic agent of the present invention can be expected to exert a therapeutic effect by application as systemic therapy to patients, and additionally, by local application to cancer tissues.

The therapeutic agent of the present invention can be administered as a pharmaceutical composition containing at least one pharmaceutically suitable ingredient. The pharmaceutically suitable ingredients can be appropriately selected and applied from formulation additives or the like that are generally used in the art, in view of the dosage, the administration concentration or the like of the antibody-drug conjugate used in the present invention. For example, the therapeutic agent of the present invention can be administered as a pharmaceutical composition (hereinafter, referred to as "the pharmaceutical composition of the present invention") containing a buffer such as a histidine buffer, an excipient such as sucrose or trehalose, and a surfactant such as polysorbate 80 or 20. The pharmaceutical composition of the present invention can be preferably used as an injection, can be more preferably used as an aqueous injection or a lyophilized injection, and can be even more preferably used as a lyophilized injection.

In the case that the pharmaceutical composition of the present invention is an aqueous injection, it can be preferably diluted with a suitable diluent and then given as an intravenous infusion. For the diluent, a dextrose solution, physiological saline, and the like, can be exemplified, and a dextrose solution can be preferably exemplified, and a 5% dextrose solution can be more preferably exemplified.

In the case that the pharmaceutical composition of the present invention is a lyophilized injection, it can be preferably dissolved in water for injection, subsequently a required amount can be diluted with a suitable diluent and then given as an intravenous infusion. For the diluent, a dextrose solution, physiological saline, and the like, can be exemplified, and a dextrose solution can be preferably exemplified, and a 5% dextrose solution can be more preferably exemplified.

Examples of the administration route which may be used to administer the pharmaceutical composition of the present invention include intravenous, intradermal, subcutaneous, intramuscular and intraperitoneal routes, and preferably include an intravenous route. Further, the pharmaceutical composition of the present invention can also be administered by direct injection to the brain parenchyma, the pia mater or the arachnoid membrane.

The antibody-drug conjugate used in the present invention can be administered to a human once at intervals of 1 to 180 days, and can be preferably administered once a week, once every 2 weeks, once every 3 weeks or once every 4 weeks, and can be even more preferably administered once every 3 weeks. Also, the antibody-drug conjugate used in the present invention can be administered at a dose of about 0.001 to 100 mg/kg, and can be preferably administered at a dose of 0.8 to 12.4 mg/kg. In the case that the antibody-drug conjugate used in the present invention is an anti-HER2 antibody-drug conjugate, it can be preferably administered once every 3 weeks at a dose of 0.8 mg/kg, 1.6 mg/kg, 3.2 mg/kg, 5.4 mg/kg, 6.4 mg/kg, 7.4 mg/kg or 8 mg/kg, can be more preferably administered once every 3 weeks at a dose of 5.4, 6.4, or 7.4 mg/kg, and can be even more preferably administered once every 3 weeks at a dose of 5.4 mg/kg or 6.4 mg/kg. In the case that the antibody-drug conjugate used in the present invention is an anti-HER3 antibody-drug conjugate, it can be preferably administered once every 3 weeks at a dose of 1.6 mg/kg, 3.2 mg/kg, 4.8 mg/kg, 5.6 mg/kg, 6.4 mg/kg, 8.0 mg/kg, 9.6 mg/kg or 12.8 mg/kg, and can be more preferably administered once every 3 weeks at a dose of 4.8 mg/kg, 5.6 mg/kg or 6.4 mg/kg. In the case that the antibody-drug conjugate used in the present invention is an anti-TROP2 antibody-drug conjugate, it can be preferably administered once every 3 weeks at a dose of 0.27 mg/kg, 0.5 mg/kg, 1.0 mg/kg, 2.0 mg/kg, 4.0 mg/kg, 6.0 mg/kg or 8.0 mg/kg, and can be more preferably administered once every 3 weeks at a dose of 4.0 mg/kg, 6.0 mg/kg or 8.0 mg/kg.

The therapeutic agent of the present invention can also be administered in combination with a cancer therapeutic agent other than the antibody-drug conjugate used in the present invention, thereby enhancing the antitumor effect. Other cancer therapeutic agents used for such purpose may be administered to a subject simultaneously with, separately from, or subsequently to the therapeutic agent of the present invention, and may be administered while varying the administration interval for each. Such cancer therapeutic agents are not limited as long as they are agents having antitumor activity, and can be exemplified by at least one selected from the group consisting of irinotecan (CPT-11), cisplatin, carboplatin, oxaliplatin, fluorouracil (5-FU), gemcitabine, capecitabine, paclitaxel, docetaxel, doxorubicin, epirubicin, cyclophosphamide, mitomycin C, tegafur-gimeracil-oteracil combination, cetuximab, panitumumab, bevacizumab, ramucirumab, regorafenib, trifluridine-tipiracil combination, gefitinib, erlotinib, afatinib, methotrexate, pemetrexed, tamoxifen, toremifene, fulvestrant, leuprorelin, goserelin, letrozole, anastrozole, progesterone formulation, trastuzumab emtansine, trastuzumab, pertuzumab and lapatinib.

The therapeutic agent of the present invention can also be used in combination with radiotherapy. For example, a cancer patient may receive radiotherapy before and/or after receiving, or simultaneously with, the treatment by the therapeutic agent of the present invention. Examples of the radiotherapy method can include Whole brain radiation therapy (WBRT), Stereotactic irradiation (STI) and Stereotactic radiosurgery (SRS).

The therapeutic agent of the present invention can also be used as an adjuvant chemotherapy in combination with a surgical procedure. Surgical procedures are carried out by, for example, removing the whole or a part of a brain tumor. The therapeutic agent of the present invention may be administered for the purpose of diminishing the size of a brain tumor before a surgical procedure (referred to as pre-operative adjuvant chemotherapy, or neoadjuvant therapy), or may be administered after a surgical procedure for the purpose of preventing the recurrence of a brain tumor (referred to as post-operative adjuvant chemotherapy, or adjuvant therapy).

EXAMPLES

The present invention is specifically described in view of the examples shown below. However, the present invention is not limited to these. Further, it is by no means to be interpreted in a limited way.

Example 1: Production of Antibody-Drug Conjugate

In accordance with a production method described in International Publication No. WO 2015/115091 with use of a humanized anti-HER2 antibody (an antibody comprising a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2), an antibody-drug conjugate in which a drug-linker represented by the following formula:

[Formula 22]

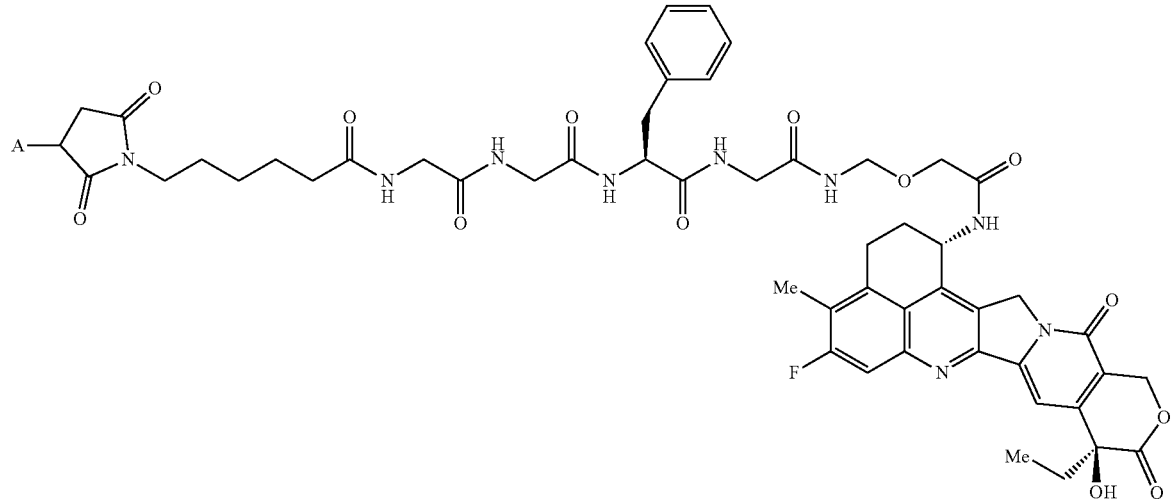

wherein A represents a connecting position to an antibody, is conjugated to the anti-HER2 antibody via a thioether bond (hereinafter, referred to as the "antibody-drug conjugate (1)") was produced. DAR of the antibody-drug conjugate (1) is 7.8.

Example 2: Life Prolongation Test

Mouse: 5 to 6-week-old female BALB/c nude mice (Charles River Laboratories Japan, Inc.) were subjected to the experiment.

The antibody-drug conjugate (1) was diluted with ABS buffer (10 mM acetate buffer (pH 5.5), 5% sorbitol) and intravenously administered into the tail vein at a solution volume of 10 mL/kg.

KPL-4-Luc was used, in which a luciferase gene was transfected into KPL-4 cells, a human breast cancer line obtained from Dr. Junichi Kurebayashi, Kawasaki Medical School (British Journal of Cancer, (1999) 79 (5/6). 707-717). KPL-4-Luc was suspended in physiological saline, $1 \times 10^4$ cells were intracranially transplanted to female nude mice, and the mice were randomly grouped 7 days after the transplantation (Day 0). The antibody-drug conjugate (1) was intravenously administered at a dose of 10 mg/kg to the tail vein on Days 0 and 21. A solvent was administered to the control groups. The number of mice in each group was five and the presence or absence of survival was observed up to Day 28. From the viewpoint of animal ethics, in the case that a weight loss of 30% or more and abnormal behavior (circling movements, eating/drinking disorders, and the like) were found, euthanization was carried out. Further, luciferin was intraperitoneally administered to each mouse on Days 14, 21 and 28 to confirm tumor localization and amount of tumor with the luciferase activity of KPL-4-Luc as an indicator, and luminescence of the head was measured using In Vivo Imaging System (IVIS). A solvent-administered group (2 mice) was established as satellite, the formalin fixed paraffin embedded section of the mouse head was produced on Day 14, and hematoxylin and eosin staining was carried out.

The results are shown in FIGS. 9 to 11. For the control groups, death was found from Day 14, and all of the mice died by Day 26. In contrast, for the antibody-drug conjugate (1)-administered groups, all the mice survived until Day 28 (FIG. 9). For the luminescence by KPL-4-Luc, the tumor growth was found in the mice of the antibody-drug conjugate (1)-administered groups by Day 21, but luminescence diminishment was found on Day 28, which was 1 week after the second administration, suggesting that the antibody-drug conjugate (1) exerts efficacy to tumors in the brain (FIG. 10). In the pathological images of the brain on Day 14, tumor masses were found around the olfactory bulb, in the nasal concha, the cerebral parenchyma, at the base of the brain, in the cerebral ventricle and around the cerebellum in 2/2 cases (FIG. 11).

These results suggested that the antibody-drug conjugate (1) exerts efficacy to metastatic brain tumors and exerts life-prolonging effects.

Free Text of Sequence Listing
    SEQ ID NO: 1—Amino acid sequence of a heavy chain of the anti-HER2 antibody
    SEQ ID NO: 2—Amino acid sequence of a light chain of the anti-HER2 antibody
    SEQ ID NO: 3—Amino acid sequence of a heavy chain of the anti-HER3 antibody SEQ ID NO: 4—Amino acid sequence of a light chain of the anti-HER3 antibody
SEQ ID NO: 5—Amino acid sequence of a heavy chain of the anti-TROP2 antibody
SEQ ID NO: 6—Amino acid sequence of a light chain of the anti-TROP2 antibody
SEQ ID NO: 7—Amino acid sequence of a heavy chain of the anti-B7-H3 antibody
SEQ ID NO: 8—Amino acid sequence of a light chain of the anti-B7-H3 antibody
SEQ ID NO: 9—Amino acid sequence of a heavy chain of the anti-GPR20 antibody
SEQ ID NO: 10—Amino acid sequence of a light chain of the anti-GPR20 antibody
SEQ ID NO: 11—Amino acid sequence of a heavy chain of the anti-CDH6 antibody
SEQ ID NO: 12—Amino acid sequence of a light chain of the anti-CDH6 antibody

The invention claimed is:

1. A method of treating a metastatic brain tumor comprising, administering to a subject with a metastatic brain tumor an antibody-drug conjugate comprising a drug-linker conjugated to an antibody via a thioether bond, wherein the drug-linker comprises the following formula:

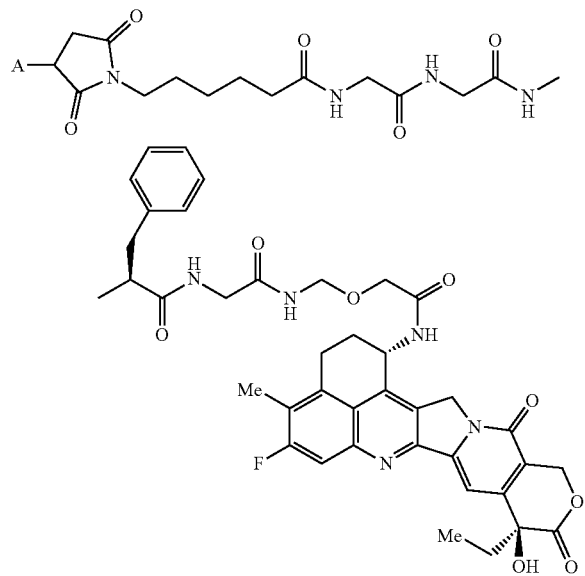

wherein A represents a connecting position to an antibody.

2. The method according to claim 1, wherein the metastatic brain tumor is metastasized from at least one primary cancer selected from the group consisting of breast cancer, lung cancer, melanoma, renal cell cancer, kidney cancer, colorectal cancer, gastric cancer, head and neck cancer, hepatocellular cancer, liver cancer, ovarian cancer, prostate cancer, bladder cancer, pancreatic cancer, endometrial cancer, thyroid cancer, malignant lymphoma, and sarcoma.

3. The method according to claim 1, wherein the metastatic brain tumor is metastasized from at least one primary cancer selected from the group consisting of breast cancer, lung cancer, and melanoma.

4. The method according to claim 1, wherein the metastatic brain tumor is metastasized from breast cancer.

5. The method according to claim 1, wherein the metastatic brain tumor is metastasized from lung cancer.

6. The method according to claim 1, wherein the metastatic brain tumor is metastasized from melanoma.

7. The method according to claim 1, wherein the antibody is an anti-HER2 antibody, an anti-HER3 antibody, an anti-TROP2 antibody, an anti-B7-H3 antibody, an anti-GPR20 antibody, or an anti-CDH6 antibody.

8. The method according to claim 7, wherein the antibody is an anti-HER2 antibody.

9. The method according to claim 8, wherein the anti-HER2 antibody comprises a heavy chain consisting of amino acid residues 1 to 449 of SEQ ID NO: 1 and a light chain consisting of amino acid residues 1 to 214 of SEQ ID NO: 2.

10. The method according to claim 8, wherein the anti-HER2 antibody comprises a heavy chain consisting of the amino acid sequence of SEQ ID NO: 1 and a light chain consisting of the amino acid sequence of SEQ ID NO: 2.

11. The method according to claim 9, wherein the average number of units of the drug-linker conjugated per antibody molecule in the antibody-drug conjugate is in the range of from 7 to 8.

12. The method according to claim 7, wherein the antibody is an anti-HER3 antibody.

13. The method according to claim 12, wherein the anti-HER3 antibody comprises a heavy chain consisting of the amino acid sequence of SEQ ID NO: 3 and a light chain consisting of the amino acid sequence of SEQ ID NO: 4.

14. The method according to claim 12, wherein the anti-HER3 antibody comprises a heavy chain consisting of the amino acid sequence of SEQ ID NO: 3 in which a lysine residue at the carboxyl terminus of the heavy chain has been removed, and a light chain consisting of the amino acid sequence of SEQ ID NO: 4.

15. The method according to claim 13, wherein the average number of units of the drug-linker conjugated per antibody molecule in the antibody-drug conjugate is in the range of from 7 to 8.

16. The method according to claim 7, wherein the antibody is an anti-TROP2 antibody.

17. The method according to claim 16, wherein the anti-TROP2 antibody comprises a heavy chain consisting of amino acid residues 20 to 470 of SEQ ID NO: 5 and a light chain consisting of amino acid residues 21 to 234 of SEQ ID NO: 6.

18. The method according to claim 16, wherein the anti-TROP2 antibody comprises a heavy chain consisting of amino acid residues 20 to 469 of SEQ ID NO: 5 and a light chain consisting of amino acid residues 21 to 234 of SEQ ID NO: 6.

19. The method according to claim 17, wherein the average number of units of the drug-linker conjugated per antibody molecule in the antibody-drug conjugate is in the range of from 3.5 to 4.5.

20. The method according to claim 7, wherein the antibody is an anti-B7-H3 antibody.

21. The method according to claim 20, wherein the anti-B7-H3 antibody comprises a heavy chain consisting of amino acid residues 20 to 471 of SEQ ID NO: 7 and a light chain consisting of amino acid residues 21 to 233 of SEQ ID NO: 8.

22. The method according to claim 20, wherein the anti-B7-H3 antibody comprises a heavy chain consisting of amino acid residues 20 to 470 of SEQ ID NO: 7 and a light chain consisting of amino acid residues 21 to 233 of SEQ ID NO: 8.

23. The method according to claim 21, wherein the average number of units of the drug-linker conjugated per antibody molecule in the antibody-drug conjugate is in the range of from 3.5 to 4.5.

24. The method according to claim 7, wherein the antibody is an anti-GPR20 antibody.

25. The method according to claim 24, wherein the anti-GPR20 antibody comprises a heavy chain consisting of amino acid residues 20 to 472 of SEQ ID NO: 9 and a light chain consisting of amino acid residues 21 to 234 of SEQ ID NO: 10.

26. The method according to claim 24, wherein the anti-GPR20 antibody comprises a heavy chain consisting of amino acid residues 20 to 471 of SEQ ID NO: 9 and a light chain consisting of amino acid residues 21 to 234 of SEQ ID NO: 10.

27. The method according to claim 25, wherein the average number of units of the drug-linker conjugated per antibody molecule in the antibody-drug conjugate is in the range of from 7 to 8.

28. The method according to claim 7, wherein the antibody is an anti-CDH6 antibody.

29. The method according to claim 28, wherein the anti-CDH6 antibody comprises a heavy chain consisting of amino acid residues 20 to 471 of SEQ ID NO: 11 and a light chain consisting of amino acid residues 21 to 233 of SEQ ID NO: 12.

30. The method according to claim 29, wherein the anti-CDH6 antibody comprises a heavy chain consisting of amino acid residues 20 to 470 of SEQ ID NO: 11 and a light chain consisting of amino acid residues 21 to 233 of SEQ ID NO: 12.

31. The method according to claim 29, wherein the average number of units of the drug-linker conjugated per antibody molecule in the antibody-drug conjugate is in the range of from 7 to 8.

32. The method according to claim 10, wherein the metastatic brain tumor is metastasized from at least one primary cancer selected from the group consisting of breast cancer, lung cancer, melanoma, gastric cancer, colorectal cancer, bladder cancer and sarcoma.

33. The method according to claim 11, wherein the metastatic brain tumor is metastasized from at least one primary cancer selected from the group consisting of breast cancer, lung cancer, melanoma, gastric cancer, colorectal cancer, bladder cancer and sarcoma.

34. The method according to claim 14, wherein the metastatic brain tumor is metastasized from at least one primary cancer selected from the group consisting of breast cancer, lung cancer, melanoma, gastric cancer, colorectal cancer, bladder cancer and sarcoma.

35. The method according to claim 15, wherein the metastatic brain tumor is metastasized from at least one primary cancer selected from the group consisting of breast cancer, lung cancer, melanoma, gastric cancer, colorectal cancer, bladder cancer and sarcoma.

36. The method according to claim 18, wherein the metastatic brain tumor is metastasized from at least one primary cancer selected from the group consisting of breast cancer, lung cancer, melanoma, gastric cancer, colorectal cancer, bladder cancer and sarcoma.

37. The method according to claim 19, wherein the metastatic brain tumor is metastasized from at least one primary cancer selected from the group consisting of breast cancer, lung cancer, melanoma, gastric cancer, colorectal cancer, bladder cancer and sarcoma.

38. The method according to claim 30, wherein the metastatic brain tumor is metastasized from at least one primary cancer selected from the group consisting of lung cancer, renal cell cancer, kidney cancer, colorectal cancer, gastric cancer, head and neck cancer, ovarian cancer and endometrial cancer.

39. The method according to claim 31, wherein the metastatic brain tumor is metastasized from at least one primary cancer selected from the group consisting of lung cancer, renal cell cancer, kidney cancer, colorectal cancer, gastric cancer, head and neck cancer, ovarian cancer and endometrial cancer.

40. The method according to claim 22, wherein the metastatic brain tumor is metastasized from at least one primary cancer selected from the group consisting of breast cancer, lung cancer, head and neck cancer, gastric cancer, colorectal cancer, bladder cancer, sarcoma, prostate cancer and endometrial cancer.

41. The method according to claim 23, wherein the metastatic brain tumor is metastasized from at least one primary cancer selected from the group consisting of breast cancer, lung cancer, head and neck cancer, gastric cancer, colorectal cancer, bladder cancer, sarcoma, prostate cancer and endometrial cancer.

42. The method according to claim 1, wherein the metastatic brain tumor is metastasized from gastric cancer.

43. The method according to claim 1, wherein the metastatic brain tumor is metastasized from colorectal cancer.

44. The method according to claim 1, wherein the metastatic brain tumor is metastasized from bladder cancer.

45. The method according to claim 1, wherein the metastatic brain tumor is metastasized from sarcoma.

46. The method according to claim 1, wherein the metastatic brain tumor is metastasized from renal cell cancer.

47. The method according to claim 1, wherein the metastatic brain tumor is metastasized from kidney cancer.

48. The method according to claim 1, wherein the metastatic brain tumor is metastasized from head and neck cancer.

49. The method according to claim 1, wherein the metastatic brain tumor is metastasized from ovarian cancer.

50. The method according to claim 1, wherein the metastatic brain tumor is metastasized from endometrial cancer.

51. The method according to claim 1, wherein the metastatic brain tumor is metastasized from prostate cancer.

52. The method according to claim 1, wherein the metastatic brain tumor is metastasized from non-small cell lung cancer.

53. The method according to claim 32, wherein the average number of units of the drug-linker conjugated per antibody molecule in the antibody-drug conjugate is in the range of from 7 to 8.

54. The method according to claim 34, wherein the average number of units of the drug-linker conjugated per antibody molecule in the antibody-drug conjugate is in the range of from 7 to 8.

55. The method according to claim 36, wherein the average number of units of the drug-linker conjugated per antibody molecule in the antibody-drug conjugate is in the range of from 3.5 to 4.5.

56. The method according to claim 40, wherein the average number of units of the drug-linker conjugated per antibody molecule in the antibody-drug conjugate is in the range of from 3.5 to 4.5.

57. The method according to claim 38, wherein the average number of units of the drug-linker conjugated per antibody molecule in the antibody-drug conjugate is in the range of from 7 to 8.

* * * * *

UNITED STATES PATENT AND TRADEMARK OFFICE
CERTIFICATE OF CORRECTION

| | | |
|---|---|---|
| PATENT NO. | : 12,220,604 B2 | Page 1 of 1 |
| APPLICATION NO. | : 17/264250 | |
| DATED | : February 11, 2025 | |
| INVENTOR(S) | : Sugihara et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1019 days.

Signed and Sealed this
Sixteenth Day of September, 2025

Coke Morgan Stewart
*Acting Director of the United States Patent and Trademark Office*

SEQUENCE LISTING

```
<160> NUMBER OF SEQ ID NOS: 12

<210> SEQ ID NO 1
<211> LENGTH: 450
<212> TYPE: PRT
<213> ORGANISM: Artificial Sequence
<220> FEATURE:
<223> OTHER INFORMATION: Heavy chain of anti-HER2 antibody

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Light chain of anti-HER2 antibody

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190
```

Ala Cys Glu Val Thr His Gln Gly Leu Ser Ser Pro Val Thr Lys Ser
            195                 200                 205

Phe Asn Arg Gly Glu Cys
            210

<210> SEQ ID NO 3
<211> LENGTH: 447
<212> TYPE: PRT
<213> ORGANISM: Artificial Sequence
<220> FEATURE:
<223> OTHER INFORMATION: Heavy chain of anti-HER3 antibody

<400> SEQUENCE: 3

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys
            435                 440                 445

<210> SEQ ID NO 4
<211> LENGTH: 220
<212> TYPE: PRT
<213> ORGANISM: Artificial Sequence
<220> FEATURE:
<223> OTHER INFORMATION: Light chain of anti-HER3 antibody

<400> SEQUENCE: 4

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 5
<211> LENGTH: 470
<212> TYPE: PRT
<213> ORGANISM: Artificial Sequence
<220> FEATURE:

<223> OTHER INFORMATION: Heavy chain of anti-TROP2 antibody

<400> SEQUENCE: 5

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Thr Ala Gly Met Gln Trp Val Arg Gln Ala Pro Gly Gln Gly Leu
    50                  55                  60

Glu Trp Met Gly Trp Ile Asn Thr His Ser Gly Val Pro Lys Tyr Ala
65                  70                  75                  80

Glu Asp Phe Lys Gly Arg Val Thr Ile Ser Ala Asp Thr Ser Thr Ser
                85                  90                  95

Thr Ala Tyr Leu Gln Leu Ser Ser Leu Lys Ser Glu Asp Thr Ala Val
            100                 105                 110

Tyr Tyr Cys Ala Arg Ser Gly Phe Gly Ser Ser Tyr Trp Tyr Phe Asp
        115                 120                 125

Val Trp Gly Gln Gly Thr Leu Val Thr Val Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400
```

```
Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
            450                 455                 460

Ser Leu Ser Pro Gly Lys
465                 470

<210> SEQ ID NO 6
<211> LENGTH: 234
<212> TYPE: PRT
<213> ORGANISM: Artificial Sequence
<220> FEATURE:
<223> OTHER INFORMATION: Light chain of anti-TROP2 antibody

<400> SEQUENCE: 6

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Val Ser Thr Ala Val Ala Trp Tyr Gln Gln Lys Pro Gly Lys Ala Pro
    50                  55                  60

Lys Leu Leu Ile Tyr Ser Ala Ser Tyr Arg Tyr Thr Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Val Tyr Tyr Cys Gln Gln His Tyr
            100                 105                 110

Ile Thr Pro Leu Thr Phe Gly Gln Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 7
<211> LENGTH: 471
<212> TYPE: PRT
<213> ORGANISM: Artificial Sequence
<220> FEATURE:
<223> OTHER INFORMATION: Heavy chain of anti-B7-H3 antibody

<400> SEQUENCE: 7
```

-continued

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
            35                  40                  45

Thr Asn Tyr Val Met His Trp Val Arg Gln Ala Pro Gly Gln Gly Leu
        50                  55                  60

Glu Trp Met Gly Tyr Ile Asn Pro Tyr Asn Asp Asp Val Lys Tyr Asn
65                  70                  75                  80

Glu Lys Phe Lys Gly Arg Val Thr Ile Thr Ala Asp Glu Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Trp Gly Tyr Tyr Gly Ser Pro Leu Tyr Tyr Phe
            115                 120                 125

Asp Tyr Trp Gly Gln Gly Thr Leu Val Thr Val Ser Ser Ala Ser Thr
        130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
            210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
        290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
        370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415
```

```
Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
450                 455                 460

Leu Ser Leu Ser Pro Gly Lys
465             470

<210> SEQ ID NO 8
<211> LENGTH: 233
<212> TYPE: PRT
<213> ORGANISM: Artificial Sequence
<220> FEATURE:
<223> OTHER INFORMATION: Light chain of anti-B7-H3 antibody

<400> SEQUENCE: 8

Met Val Leu Gln Thr Gln Val Phe Ile Ser Leu Leu Leu Trp Ile Ser
1               5                   10                  15

Gly Ala Tyr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Ser Arg
        35                  40                  45

Leu Ile Tyr Met His Trp Tyr Gln Gln Lys Pro Gly Gln Ala Pro Arg
    50                  55                  60

Pro Leu Ile Tyr Ala Thr Ser Asn Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Asn Ser
            100                 105                 110

Asn Pro Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 9
<211> LENGTH: 472
<212> TYPE: PRT
<213> ORGANISM: Artificial Sequence
<220> FEATURE:
<223> OTHER INFORMATION: Heavy chain of anti-GPR20 antibody

<400> SEQUENCE: 9

Met Lys His Leu Trp Phe Phe Leu Leu Leu Val Ala Ala Pro Arg Trp
1               5                   10                  15
```

```
Val Leu Ser Glu Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Tyr Tyr Ile Ser Trp Ile Arg Gln Ala Pro Gly Gln Gly Leu
     50                  55                  60

Lys Tyr Met Gly Phe Ile Asn Pro Gly Ser Gly His Thr Asn Tyr Asn
 65                  70                  75                  80

Glu Lys Phe Lys Gly Arg Val Thr Ile Thr Ala Asp Lys Ser Ser Ser
                 85                  90                  95

Thr Ala Thr Met Glu Leu Ser Ser Leu Arg Ser Glu Asp Thr Ala Val
             100                 105                 110

Tyr Tyr Cys Ala Arg Gly Ala Gly Phe Leu Arg Ile Ile Thr Lys
         115                 120                 125

Phe Asp Tyr Trp Gly Gln Gly Thr Leu Val Thr Val Ser Ser Ala Ser
 130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                 165                 170                 175

Glu Pro Val Thr Val Ser Trp Asn Ser Gly Ala Leu Thr Ser Gly Val
             180                 185                 190

His Thr Phe Pro Ala Val Leu Gln Ser Ser Gly Leu Tyr Ser Leu Ser
         195                 200                 205

Ser Val Val Thr Val Pro Ser Ser Leu Gly Thr Gln Thr Tyr Ile
     210                 215                 220

Cys Asn Val Asn His Lys Pro Ser Asn Thr Lys Val Asp Lys Arg Val
225                 230                 235                 240

Glu Pro Lys Ser Cys Asp Lys Thr His Thr Cys Pro Pro Cys Pro Ala
                 245                 250                 255

Pro Glu Leu Leu Gly Gly Pro Ser Val Phe Leu Phe Pro Pro Lys Pro
             260                 265                 270

Lys Asp Thr Leu Met Ile Ser Arg Thr Pro Glu Val Thr Cys Val Val
         275                 280                 285

Val Asp Val Ser His Glu Asp Pro Glu Val Lys Phe Asn Trp Tyr Val
 290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                 325                 330                 335

Asp Trp Leu Asn Gly Lys Glu Tyr Lys Cys Lys Val Ser Asn Lys Ala
             340                 345                 350

Leu Pro Ala Pro Ile Glu Lys Thr Ile Ser Lys Ala Lys Gly Gln Pro
         355                 360                 365

Arg Glu Pro Gln Val Tyr Thr Leu Pro Pro Ser Arg Glu Glu Met Thr
 370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                 405                 410                 415

Lys Thr Thr Pro Pro Val Leu Asp Ser Asp Gly Ser Phe Phe Leu Tyr
             420                 425                 430
```

```
Ser Lys Leu Thr Val Asp Lys Ser Arg Trp Gln Gln Gly Asn Val Phe
            435                 440                 445

Ser Cys Ser Val Met His Glu Ala Leu His Asn His Tyr Thr Gln Lys
        450                 455                 460

Ser Leu Ser Leu Ser Pro Gly Lys
465                 470

<210> SEQ ID NO 10
<211> LENGTH: 234
<212> TYPE: PRT
<213> ORGANISM: Artificial Sequence
<220> FEATURE:
<223> OTHER INFORMATION: Light chain of anti-GPR20 antibody

<400> SEQUENCE: 10

Met Val Leu Gln Thr Gln Val Phe Ile Ser Leu Leu Trp Ile Ser
1               5                   10                  15

Gly Ala Tyr Gly Asp Thr Gln Leu Thr Gln Ser Pro Ser Ser Leu Ser
            20                  25                  30

Ala Ser Val Gly Asp Arg Val Thr Ile Thr Cys Arg Ala Ser Lys Ser
        35                  40                  45

Val Ser Thr Tyr Ile His Trp Tyr Gln Gln Lys Pro Gly Lys Gln Pro
    50                  55                  60

Lys Leu Leu Ile Tyr Ser Ala Gly Asn Leu Glu Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Asn Tyr Tyr Cys Gln Gln Ile Asn
            100                 105                 110

Glu Leu Pro Tyr Thr Phe Gly Gln Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 11
<211> LENGTH: 471
<212> TYPE: PRT
<213> ORGANISM: Artificial Sequence
<220> FEATURE:
<223> OTHER INFORMATION: Heavy chain of anti-CDH6 antibody

<400> SEQUENCE: 11

Met Lys His Leu Trp Phe Phe Leu Leu Leu Val Ala Ala Pro Arg Trp
1               5                   10                  15

Val Leu Ser Glu Val Gln Leu Val Gln Ser Gly Ala Glu Val Lys Lys
            20                  25                  30
```

-continued

```
Pro Gly Ala Ser Val Lys Val Ser Cys Lys Ala Ser Gly Tyr Thr Phe
            35                  40                  45
Thr Arg Asn Phe Met His Trp Val Arg Gln Ala Pro Gly Gln Gly Leu
 50                  55                  60
Glu Trp Met Gly Trp Ile Tyr Pro Gly Asp Gly Glu Thr Glu Tyr Ala
 65                  70                  75                  80
Gln Lys Phe Gln Gly Arg Val Thr Ile Thr Ala Asp Thr Ser Thr Ser
            85                  90                  95
Thr Ala Tyr Met Glu Leu Ser Ser Leu Arg Ser Glu Asp Thr Ala Val
            100                 105                 110
Tyr Tyr Cys Ala Arg Gly Val Tyr Gly Gly Phe Ala Gly Gly Tyr Phe
            115                 120                 125
Asp Phe Trp Gly Gln Gly Thr Leu Val Thr Val Ser Ser Ala Ser Thr
 130                 135                 140
Lys Gly Pro Ser Val Phe Pro Leu Ala Pro Ser Ser Lys Ser Thr Ser
145                 150                 155                 160
Gly Gly Thr Ala Ala Leu Gly Cys Leu Val Lys Asp Tyr Phe Pro Glu
            165                 170                 175
Pro Val Thr Val Ser Trp Asn Ser Gly Ala Leu Thr Ser Gly Val His
            180                 185                 190
Thr Phe Pro Ala Val Leu Gln Ser Ser Gly Leu Tyr Ser Leu Ser Ser
            195                 200                 205
Val Val Thr Val Pro Ser Ser Ser Leu Gly Thr Gln Thr Tyr Ile Cys
            210                 215                 220
Asn Val Asn His Lys Pro Ser Asn Thr Lys Val Asp Lys Arg Val Glu
225                 230                 235                 240
Pro Lys Ser Cys Asp Lys Thr His Thr Cys Pro Pro Cys Pro Ala Pro
            245                 250                 255
Glu Leu Leu Gly Gly Pro Ser Val Phe Leu Phe Pro Pro Lys Pro Lys
            260                 265                 270
Asp Thr Leu Met Ile Ser Arg Thr Pro Glu Val Thr Cys Val Val Val
            275                 280                 285
Asp Val Ser His Glu Asp Pro Glu Val Lys Phe Asn Trp Tyr Val Asp
            290                 295                 300
Gly Val Glu Val His Asn Ala Lys Thr Lys Pro Arg Glu Glu Gln Tyr
305                 310                 315                 320
Asn Ser Thr Tyr Arg Val Val Ser Val Leu Thr Val Leu His Gln Asp
            325                 330                 335
Trp Leu Asn Gly Lys Glu Tyr Lys Cys Lys Val Ser Asn Lys Ala Leu
            340                 345                 350
Pro Ala Pro Ile Glu Lys Thr Ile Ser Lys Ala Lys Gly Gln Pro Arg
            355                 360                 365
Glu Pro Gln Val Tyr Thr Leu Pro Pro Ser Arg Glu Glu Met Thr Lys
            370                 375                 380
```

```
Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
                435                 440                 445

Cys Ser Val Met His Glu Ala Leu His Asn His Tyr Thr Gln Lys Ser
450                 455                 460

Leu Ser Leu Ser Pro Gly Lys
465                 470

<210> SEQ ID NO 12
<211> LENGTH: 233
<212> TYPE: PRT
<213> ORGANISM: Artificial Sequence
<220> FEATURE:
<223> OTHER INFORMATION: Light chain of anti-CDH6 antibody

<400> SEQUENCE: 12

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
                20                  25                  30

Ala Ser Val Gly Asp Arg Val Thr Ile Thr Cys Lys Ala Ser Gln Asn
            35                  40                  45

Ile Tyr Lys Asn Leu Ala Trp Tyr Gln Gln Lys Pro Gly Lys Ala Pro
        50                  55                  60

Lys Leu Leu Ile Tyr Asp Ala Asn Thr Leu Gln Thr Gly Val Pro Ser
65                  70                  75                  80

Arg Phe Ser Gly Ser Gly Ser Gly Ser Asp Phe Thr Leu Thr Ile Ser
                85                  90                  95

Ser Leu Gln Pro Glu Asp Phe Ala Thr Tyr Phe Cys Gln Gln Tyr Tyr
                100                 105                 110

Ser Gly Trp Ala Phe Gly Gln Gly Thr Lys Val Glu Ile Lys Arg Thr
            115                 120                 125

Val Ala Ala Pro Ser Val Phe Ile Phe Pro Pro Ser Asp Glu Gln Leu
        130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```